US007776538B2

(12) United States Patent
Nitta et al.

(10) Patent No.: US 7,776,538 B2

(45) Date of Patent: Aug. 17, 2010

(54) METHOD FOR DIAGNOSING METHAMPHETAMINE DEPENDENCE

(75) Inventors: Atsumi Nitta, Nagoya (JP); Minae Niwa, Nagoya (JP); Toshitaka Nabeshima, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 0 days.

(21) Appl. No.: 11/885,597

(22) PCT Filed: Feb. 24, 2006

(86) PCT No.: PCT/JP2006/003376

§ 371 (c)(1), (2), (4) Date: May 30, 2008

(87) PCT Pub. No.: WO2006/093034

PCT Pub. Date: Sep. 8, 2006

(65) Prior Publication Data

US 2009/0155778 A1 Jun. 18, 2009

(30) Foreign Application Priority Data

Mar. 3, 2005 (JP) ............................ 2005-059518

(51) Int. Cl.

| | |
|---|---|
| ***C12Q 1/68*** | (2006.01) |
| ***G01N 33/566*** | (2006.01) |
| ***G01N 33/567*** | (2006.01) |

(52) U.S. Cl. .......................... 435/6; 436/501; 436/503; 436/504

(58) Field of Classification Search ...................... None
See application file for complete search history.

(56) References Cited

U.S. PATENT DOCUMENTS 7,193,069 B2 * 3/2007 Isogai et al. ............... 536/23.1

OTHER PUBLICATIONS

Funada et al., 2004, Ann. N.Y. Acad. Sci., 1025, pp. 76-83.*
Asunama et al., 2004, Ann. N.Y. Acad. Sci., 1025, pp. 69-75.*
Zeng et al., 2004, Ann. N.Y. Acad. Sci., 1025, pp. 236-241.*

* cited by examiner

*Primary Examiner*—Olga N Chernyshev
(74) *Attorney, Agent, or Firm*—Edwards Angell Palmer & Dodge LLP

(57) ABSTRACT

Disclosed is useful means for the therapy or diagnosis of a mental disorder. A method for screening for a compound which is effective for a mental disorder, comprising the steps of (1) providing a cell capable of expressing a gene (target gene) selected from the group consisting of a gene having the nucleotide sequence depicted in SEQ ID NO:1, a gene having the nucleotide sequence depicted in SEQ ID NO:2, a gene having the nucleotide sequence depicted in SEQ ID NO:3 and genes homologous to these genes; (2) exposing the cell to a compound to be tested; (3) determining the amount of a product of the target gene expressed in the cell after the exposure to the compound; and (4) determining the change in amount of the product of the target gene under the influence of exposure to the compound.

1 Claim, 36 Drawing Sheets genes in which expression is increased

| | ( ) strength ratio |
|---|---|
| CREB 3 | (30.00) |
| Gene 1 | (23.38) |
| Gene 2 | (22.46) |
| Odz4 | (21.70) |
| Gene 3 | (20.98) |

CREB: cAMP responsive element binding protein 3
Odz4 : odd Oz/ten-m homolog 4

FIG. 2

Gene1

Gene1 fragment BLAST research

It is completely in agreement with 3' end.

(1) gi|38079652|ref|XM_194205.2| Mus musculus cDNA sequence BC034068 (BC034068), mRNA.

(2) gi|21706576|gb|BC034068.1| Mus musculus cDNA sequence BC034068, mRNA (cDNA clone IMAGE:4216367), and partial cds.

atggtctgcg agacgaagat cgtggctacg gaggaccatg aggcactgcc gggggccaag aaggacgcgc tgctcgtcgc cgccggagcc atgtggcccc cgctgcccgc cgcgcccggg
ccggccgccg cacccccacc cgcggcaggt ccccagcccc acggaggcac cgggggcgcg gggccgccgg aggggcgcgg cgtgtgcatc cgcgagttcc gcgcagccga
gcaggaggcg gcgcgccgca tcttctacga cggcatcttg gagcgcatcc ccaacacggc tttccgcggc ctgcggcagc acccgcgcac ccaactgctc tacgccctgc tggccgccct
ctgttttgct gtgacccgct cactgctgct gacatgcctg gtgccggccg ggctcctggc cctgcgctac tactacagcc gcaaggtgat tctggcctac ctggagtgtg cgctgcacac
ggacatggct gacattgagc agtactacat gaagccacct ggttcctgtt tctgggtggc tgtgctggac ggcaacgttg tgggcatcgt ggccgcacgg gcccatgagg aggacaacac
agtggagctg ctccgcatgt ccgtggactc gcgtttccgc ggaaaaggca tcgccaaggc tctgggcagg agggtgttgg agtttgccat gctgcacaac tactctgcag tggtactggg
caccacagcc gttaaggtgg ccgcccacaa gctctatgag tcactgggct tcagacacat gggcgcgagt gatcactacg tgctgcctgg catgaccctc tcgctggccg agcgcctctt
cttccaggtc cgctaccacc gctaccgcct gcagctgcgc gaggagtgac caccaccacc tgcccaccac cctgtctgcc cccgtccacc tctgccctct tgctcactgc ctagtgcggc
cctgctttcc aatgctcacc ttggcatttg tttgggtttt cctttttcag catcatgctg gttcatcacc tggctggttc tggggccaca gggtcccagt ccagagtgct catctgcaac actctggtgg
ggtggattgt ctgcagccat ggcccttgcc tccccagccc atcagagtgg ctcatcatgc cttgaagagc agcattgtgg accatctgaa ctatccacaa agctgcccag cctgcctcca
tcagggaagg actagccttg cccatcaagc acagaacctc tacaacaacc cccccccccc caaggagcag aaccctggcc cccagccagg ctaaggctca actattggcc tctggaagag
tggtctgctg ggctggccag ccactgcccc atgggaggct gagctggtcc caggccctgc tttgccctgt gcatgctaag gacatggcct ggctgcagca tgccgcatgc cacagccccc
tgccccacta tcctgcccag cctggacctc aggcctgagc tggtgagctc ccttgtcctg tcctgagctg gcctctggag ggcctacctg cctgaccctg tctactctct ggtgaggcct ggcctggcct
aacctggctc tatccactcc tgctttgctt cgaaatcatc ttacctcttt cccttttttgg tccccgtgcc tccttgctct ggctgacttg gctggtcacc cgggtttggt tcctgtagca atccactgca
cagcatggtg gggatttcat gggggtgggg ggggacacct cccccaacac ctgttagacc aggtggccac ctcccagctg cctgaggtcc tgtggcctca tgctgtttgt ggggtctgcc
ctgtgaatgt aactagccca ggctgttgtt ggcaatgcct gccacagctt ctcccagcct gaaacaaccc attctctaat aagttacgta gacagaatag cactctgcat gactttaatt actgggacaa
aatggtagtt tgagcctcca gacacacatc tgtgtggtgc tagcatacgc atggtctctg gccccatttg atgggggtgg gtggccgggt aggtggaaga tttcagtttg aagtatggaa ggagactcta
atttagtgta aacaccccta aagtgccctc acaacacagt ctgtgaggct caggttgccc cttgattcct tgtatgcagg attgagggga ctggagggtc ctaaagcctc ataggaaggg ctgggcactg
cctcggggga agaagctggt ggttggggtg ggtccaggta tcacccacta cagactactc tgctaggtca actgttcctg gcctctcctt tttgaggttc tacttcagat ccagcctaga tgggggtggg
tatggcctag gacagggaaa ggcagtagct ggcagtggtc atgaggccag ctgaaacttg gacttagctt tagtccaggg ggtgcataaa ggcccgtcca cattcctctg tgtggggctt
ggggtgagga gtggcaggct aggtagacca tagagctggg cccctggcac caaggctaca ttattagaaa ggctctttag agttaatgag ttggtggaac aagcccagct tcctgagggg
cctttgtcc tgttagcaat tgaggcattt gcagaacact gtacagaccc cgctctcccc tgtacattcc tccctggtgg tgcccggtcc ccgcttgggg atgggagttt tgtagactgt acagaaattg
gcaccctatt ttcttgcagc tctcagattt tgttaatctg gattatacag acagatgtaa agtgttttag caaaatgg (SEQ ID NO:21)

primer design

| | region | oligo | length | tm | gc% | sequence | expected size of product |
|---|---|---|---|---|---|---|---|
| gene1-L1 | upstream of fragment | left primer | 20 | 69.96 | 65.00 | cttgcctccccagcccatca (SEQ ID NO:22) | 181 |
| gene1-R1 | | right primer | 20 | 70.06 | 70.00 | ctgggggccagggttctgct (SEQ ID NO:23) | |
| gene1-L2 | inside of fragment | left primer | 20 | 70.44 | 70.00 | gggtggccgggtaggtggaa (SEQ ID NO:24) | 184 |
| gene1-R2 | | right primer | 20 | 70.20 | 70.00 | ggcagtgcccagcccttcct (SEQ ID NO:25) | |
| gene1-L3 | inside of fragment + downstream of fragment | left primer | 22 | 64.27 | 54.55 | tgtacattcctccctggtggtg (SEQ ID NO:26) | 100 |
| gene1-R3 | | right primer | 27 | 65.06 | 40.74 | aaatctgagagctgcaagaaaataggg (SEQ ID NO:27) | |

*FIG. 3*

Gene2

Gene2 fragment BLAST research

It is completely in agreement with 3' end.

gi|31542031|ref|NM_028990.2| Mus musculus RIKEN cDNA 8430437G11 gene (8430437G11Rik) mRNA.

GAGTCTCAAA TTAGCTTCAG AGCAGTTTAT TATTCTGTCA TTTTTGTAAG AGTCCACTGC CTTAGTTTCA TAATTTATAA AATACAAATT TCTATGTTAA ATTATTAAGA GCATTTGGGA AGGTGTAATA AAATCAATCA
CAGAAAAATA CTTAGAATAA TTAGATCATA GACAATACCC ATGGCTGTGT ATAGAGTTGT TTCATATGGA AAGGAAGAAA GGAATTGTAG GATTAGAGCT AGAGAGAGCA ATGCCTTTCC ACTTAGGTAG
GGGAGCCTAG CTCCTGATAC ACAGATATGT GCACAGCAAG GTAACATCTC AACGCTAGTT TCCTTATTTA ATTGTGGACC TGAAGAACCT AAAAATTATA CAAAACTGAT GTGAAATGGC ACCCATCTGA
AATTCAAGAT GCACACAAAT GAATGATTTA TTCAGTGAAA TTTACTATCT GTATTTCTAG TTGTAAAACA AGATTCATTT TTTAAAAAAA ATATTGTATA TAGGATGCCA CTAACTTTCA ATATTGTATC AATTCTTCAG
TATTCTGGAA TAAGGAAATA TTTTCAAATC AACATGCCAC CAAACATAAA CTCTAAAAGC AAAGGCATTT TGTATAACTT CCACTTTTAA TACAGTAAAA TATTCAGGAA CTCTTAATTT CACATTAAAT GAAAAATTAA
TTTTTTACAA AATATTATTC AAAGTATTAA GAGTACAATA TTCAAAACAT AGAAATAGGC TGTAGCAATG CTGCATAGAT AACAGTATAC AAGTTCCCTG ATGGTGTGAC TTCTTTCTAA ATAAAATGTC AGTTTTCAAG
TCATTGGTAG AAAATGGTAG ATGCATCCGT TACCTTCCCT CTCTGGGCAT GGAAAAATGG CTTCAACGGT GAGAAGTCAC CATGGTAAGA AAGTCTAATC TCCACTTTAA TTATACCTCC CTCTTTCAAA
GATGAAAATC TAGAATGTAA GGATAATTGG AAGGGGACAG GAAGTGACTT ACCTCTTAAG GAGATATCCT GATCAGCGCC TACTTTACTC CAACAAAACA CTGAATTAAA GTTTACAAAT TACAACCATA
GCATTATGCT TACCTAAAAC TGCCAAAATG AATACTTTTT TACATAATAC AATACAGGTA TATAACAACA ACAACAACAA AATGATCTGT TCCCATCCTT GACCTTCAGC AGAAAAAAGT TATTACAATA GGACTGAAAA
GCAACTTTCA TGGCAGAGTA CTAACTCCTC ATAAATACGT AAGACAGGAA GAATCGGTCA ATGAGAAACT GATACATTTA TTTTTGTAAG TGTGTACTTT TTGAAAAGAA TGGCAATTTA CTTGAAAGGA
ATTTGTAGCT GGAAATACTA CTCATTAAGA AAACAAAATT ACCCTGAGAA GGACTCTTAA ATTTACCAGT ATTTTCAAAG TCCCTCACTA ACCATGAAGG AACACTTTGT AGCATGTAAG CTCTTATTGT TACCTACATT
AACAATGCTT TCATCTCAAA GGCAGTTGGG GCTTTTCTGC TGTACTGTAA AGGTCATAGC CAAGACATCT GGGTGTGGTG GTAAAAGGGC ATTTTGCAGT CATTATGAGC AGGTCTCTTC CTGCTCCAAG
TATTTATACT TCTGCAAACA GTCCTGGGGC CAAACCTATA TGAATCACAC ACATGAAAGA ATCTCCTACT AAGTAAACTG GTAGTTCTCT TAAAACACAC TTGTCTGGTC TACATTCTCT AACGGGTGCC
TAGAAAATAA GGCATTAGGA ATTGTCCATT GGCCACTCCA GAGCACAGAC AACTGTGTTT CTTTTCATTG GAGACAAATG GAAAGTTATT TGAAAGTGCA CTGTTACTTT TAACATCTCT TACACATTTA CATTCAGCAT
TTTCATGACC CTCCATATAC TTTTAGTATA AAATCATGCA TATTCCCAAT ATCTTCCACA TCCCATAATT ACTTAAGAAA AGACAAAGTG AGAACAGCTA CAAATGTAGC AAGATACTTT CCACAAATAA AAATACAGCA
TACAAAAAAT GGCAAGTTAC TGATAAATGG TAACATGAAC TCTCAATAAT AGCCTTCCTT GATGTCCACA TTAAGATTTG ACAAGTTTAA AGCCTTGTCC TGTGTCCAGC ACTGTAGGAA GAAACCAACT
CATTTTTAAC CTTTTCAAGC ACCTAAAACA AGCTTTGCAG ACCCAAAAGA GGTTCAGGCC ACATAACCAG TTGGCCAAGT GCACTAACGG ATACGTAACC CGAGGGAAGT GTAACATCCA GTGCTTGGCC
ACATCGCTTC CTGTCGGCAG GTGCAGCGTG TAGTCGCTCC AGCGCTTTGA CACGCCATAC ACGGCCCTCA CTGTGCGCCC CTTCTCAGTC CAGCAGATGT TGTTTGTGGAGTTACAGTTG TATTCTACCC
AGTCTCTAGT AAAGTCACCC AGCTGTGGCG GGTCAGCTTC TTCAATATCT ACTGTCTTCG CCAGCTCAGC TCCCTGAACT GCAACATACT GGTCATTAAT CTTTCTCACT TCTTTCACCC ATGGGGTTGA ATTCTCGCTG
TCTAAGATGA TGATAAGCCG GGAACAGAAG GAACCGTTCT TCTCTCTCCA CCATTCTAAA AGCGTATCAA GGCGAAGTAT GTCTCCACCT GCGAGGGCCC ACTCTCCTGA GCCATGGGTG TGTCCACTGT
AATATAAAAC ATATGTATCA TGTCTAGGTC CATCCACTGT CCGAAGTTCA AGGAAAGCTT TCAGTTTGGA ATGCAGAGTA TCAAAAGACA GCCCACTTGT GGAATAGTCA CATCCATAGG TCTCAATCAT
ATGATATGCA AAAAATCTTT GGATGGCATT GAGCATGCCA GTAGACCTCA AATTTAACTC CTGTACATGT TCTGGCGGAA GCAGTGTTGG CTGGCCATCA GGGCTGCAGA AGTTGGTAGG GATCACAATA
GCGTATCCAA CAGAGGTTCC CCCTAAGCAG TTGCCAAGTT CATGGAAGAG CCCATGAGCC ATGGACTCCA GCGGCAAGAC AATGAGAAAC ATGCTCAAGA AGATTCCATT GGTTGGCTGC CAGGAGACTG
CTCCCAAAAT TGCCGTTGCA AGAAGACTAA AAAAAACTAA CTGCTCTGAA ATTAAGCAAA AATGACGCAT CCCTTTGGAT GCCATGATTC TGTCAAGGCT ATTGTTATCT GCCCTGTGGT TGATATACAC
TTTATGGCAG TCATTCAACT TAGTATGAAA TCCCCAAAGA GTTAAAAGAA AAATAATATG GCAAATCATC CAGAAAAATC CGAAAATGGA AAAACCTGGT ATCACAAAAT ACCAGAGATG AGTGTCTCTA
AGTTTAAATG CTGAAAGGAT GAAGAATGTA AGCTCAATCA TTGCAGTGAA AAGCACAGAA AGTCTCCTGC AAATTCTCCC ACGATGCAGA AAAGGTTTCC ACCTCTCAGT TACTGAAAGT CCACTAAAAT
AAATGTCAAG AAAAGGATCA GTTACCAGGC AAATAAAAAA ACATGCAAAA GCAATTGGAT TTTGGGGAGT TTCCAATGAA GAGAAAAATA ACAATACTGA AAAAATGATT AAGTTTGGAA TAGCTAGAAA
AGACTTCATT CTCAGGTCGA TAATGAGCAT GGCCAAAGCC ATAACCAGCA AAATAACACT CAGAGACTTC TCCACCAACA TAGTTGTGCT GGCGATGGCA AACCCAACAA GTTCCAGAAA CTCCACTGTG
GTTAGTAAAG TAGGCCGATG GCGGACATAT CCAGAAATTC TCTCCACCAA AGCACACAAT ATCCTTAAAA CTATAGATGT CAGAAGCAAA TATTTGGTTG TTTCTTCTTT CACATCACTT TTAAAGGATG
AATTATCAAG AAAACACAGA AGGCCAAGCA GAAATCCAAA CCAGAGATTG GAGAGACTTA AACTGGCTGC TTCCATTGAA AAGTAATAGT AGAGTATGCT GGCGATCCCA AGAACAAAGA GGCCGAGGAT
AAAAATCACC AAAATTAAGG AATTTGCTGT TTTTTCCCAT CTTACATAAA GGCCTAAACA TATGGCCACA AGTAAGTTGA TCCTGGCTAG ATAGCCGAGG TACCGCACGG AGGAATGCAT GTTCACTTCT
CTATTTACTT CTTCCAGCCT AGTCATTGCT AGATAGAGAC AATGACTAAC ACAGTATCGC AGTGATCTGC ACATGTAATC TGGCACTGGA GGGTCCCAAG AGGCACAAAA ATTAACTTCC TGTATTTCAT
TCAATAAAGC CAAGGTGTTG GTAATGCCTA CTCCAACATT CTCTCAGAAG TTTTCTTTGT AATGACCCGA GTCAGCGGTC GCCAGCGAGC CTCGCTCTTT CCGCTGCGAA GCTCGCAGAG CCAAAGGGCG
CGGAGCCTCC GAGCCAGAAC GCGGAGGTGA TGTGGGGACG TGAGCCCGAG GCCTCCCGCA CTAGCACCGC AAGGCCTCGG TAGAAACTTT CGCTAGGACC GACACGACCG CCATGTTTCC GCCGCTGACT
CCCAGCGCTA CGGATCGCCG TCAGGGACAA GGCGCGCCGC C (SEQ ID NO:28)

primer design

| | region | oligo | length | tm | gc% | sequence | expected size of product |
|---|---|---|---|---|---|---|---|
| gene2-L1 | upstream of fragment | left primer | 27 | 68.48 | 51.85 | GAGCAATGCCTTTCCACTTAGGTAG (SEQ ID NO:29) | 155 |
| gene2-R1 | | right primer | 24 | 68.79 | 45.83 | TCAGATGGGTGCCATTTCACATCA (SEQ ID NO:30) | |
| gene2-L2 | inside of fragment | left primer | 21 | 68.01 | 61.90 | CCTTCCCTCTCTGGGCATGGA (SEQ ID NO:31) | 151 |
| gene2-R2 | | right primer | 27 | 69.08 | 51.85 | GGTAAGTCACTTCCTGTCCCCTTCCAA (SEQ ID NO:32) | |
| gene2-L3 | downstream of fragment | left primer | 20 | 70.24 | 70.00 | ACCCAGCTGTGGCGGGTCAG (SEQ ID NO:33) | 223 |
| gene2-R3 | | right primer | 20 | 70.40 | 70.00 | GGCCCTCGCAGGTGGAGACA (SEQ ID NO:34) | |

FIG. 4

Forward primer : gagcaatgcctttccacttaggtag (SEQ ID NO:35)
Reverse primer : tcagatgggtgccatttcacatca (SEQ ID NO:36)
PCR conditions : 95°C × 5 min
→94°C × 30 s
→68°C × 40 s
→72°C × 1 min
→72°C × 5 min
→4°C × ∞
(35 cycles)

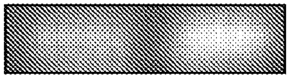

Forward primer : ccttccctctctgggcatgga (SEQ ID NO:37)
Reverse primer : ggtaagtcacttcctgtccccttccaa (SEQ ID NO:38)
PCR conditions : 95°C × 5 min
→94°C × 30 s
→68°C × 40 s
→72°C × 1 min
→72°C × 5 min
→4°C × ∞
(35 cycles)

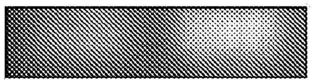

Forward primer : acccagctgtggcgggtcag (SEQ ID NO:39)
Reverse primer : ggccctcgcaggtggagaca (SEQ ID NO:40)
PCR conditions : 95°C × 5 min
→94°C × 30 s
→70°C × 40 s
→72°C × 1 min
→72°C × 5 min
→4°C × ∞
(35 cycles)

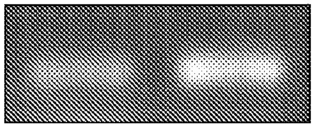

FIG. 7

METHOD FOR DIAGNOSING METHAMPHETAMINE DEPENDENCE

TECHNICAL FIELD

The present invention relates to use of a novel mental disorder-related gene in the medical field and the field or research. In detail, the present invention provides a screening method, an antipsychotic drug, and the like, using the novel mental disorder-related gene.

BACKGROUND ART

At present, aging is progressing, and it is thought that the number of patients with a mental disorder will securely increase in the future. Furthermore, at present, the social structure has been changed and it is said that we live in "times of stress." People including children and adults are exposed to various stresses every day. Abnormality in the mental condition due to stress is a problem for people of all ages. Meanwhile, dependence on psychostimulant drugs and the like, that is to say, drug dependence has been a serious social problem.

DISCLOSURE OF THE INVENTION

Problems to be Solved by the Invention

Under such circumstances, development of treatment methods for mental disorders such as schizophrenic disorder, drug dependence, and the like, is a very urgent problem. However, no radical treatment method has been established. By the way, in order to carry out an appropriate treatment, it is important to determine and understand the presence of morbidity, pathological conditions, and the like, accurately and objectively. However, under present circumstances, a diagnosis of mental disorders is much dependent upon the statement of a patient himself/herself. Therefore, correct and appropriate diagnosis may not be carried out in not a few cases. Furthermore, empirical facts show that appropriate treatment sometimes cannot be selected because there are various pathological conditions. On the other hand, if the morbidity risk is assessed in advance, preventive measures can be taken, so that the number of patients can be significantly reduced. It would bring measureless contribution to the medical field. Furthermore, many of onset and progression mechanisms of mental disorders have not been clarified, and study results are expected to be accumulated in the future.

The present invention addresses the problems discussed above, and aims to provide useful means for treatment or diagnosis of mental disorders. As to the treatment application, in particular, it is an object to provide a method of selecting drug candidates for mental disorders so as to contribute the establishment of the treatment method. As to diagnostic application, it is an object to provide a means capable of determining the presence of morbidity, understanding of pathological conditions, furthermore, assessment of morbidity risk, and the like. Furthermore, another object of the present invention is to provide a means that is directly effective in treating mental disorders. Furthermore, a further object of the present invention is to provide research tool effective for the purpose of study, for example, investigation of the causes of mental disorders.

Means to Solve the Problems

In order to achieve the above-mentioned objects, the present inventors have attempted to identify a gene that is related to mental disorders. Firstly, the present inventors have prepared a mouse with a mental disorder accompanying drug dependence so as to select a gene that is related to the expression of the mental disorder. Herein, when methamphetamine is administered to a mouse, the mouse shows hyperactivity, and when methamphetamine is administered to the mouse every day, the degree of hyperactivity is increased. This can be thought to be a mental disorder accompanying drug dependence. The present inventors have searched a gene in which the expression is extremely increased in the nucleus accumbens of this mouse. As a result, the present inventors have found three novel candidate genes. As a result of a further study, the present inventors have found the clear correlation between the expression amount of the gene and symptoms peculiar to drug dependence. It has been confirmed that the three genes are genes relating to a mental disorder. In other words, the present inventors have succeeded in identifying novel genes related to a mental disorder. This makes it possible to develop a drug for a mental disorder whose target molecule is this gene. On the other hand, this makes it possible to study for investigating the onset and progression mechanism of the mental disorder.

The present inventors further carried out homology search by using a public database under the prediction that there would be human homologous genes. As a result, the presence of a homologous gene with respect to each gene has been confirmed. That is to say, the present inventors have succeeded in identifying human genes related to a mental disorder. These genes are intended to be used in the treatment or diagnosis (including onset risk diagnosis) of a mental disorder or development of drugs for a mental disorder and in the investigation of the onset or progression mechanism of a mental disorder. Thus, these genes are very useful.

The present invention is mainly based on the above-mentioned results and findings, and has the following configuration. The first aspect of the present invention relates to a method for screening a compound that is effective for a mental disorder. The method includes: (1) preparing a cell capable of expressing a gene (target gene) selected from the group consisting of a gene having a base sequence of SEQ ID NO.: 1, a gene having a base sequence of SEQ ID NO.: 2, a gene having a base sequence of SEQ ID NO.: 3 and genes homologous to these genes; (2) exposing the cell to a test compound; (3) determining the expression level of the target gene in the cell after the exposure to the test compound; and (4) determining the change in expression level of the target gene due to exposure to the test compound.

According to one embodiment of the present invention, a screening method using an animal individual is provided. This screening method includes the steps of: (i) preparing a non-human animal; (ii) administering a test compound to the non-human animal; (iii) after administering the test compound, in the central nervous system tissue of the non-human animal, determining the expression level of the gene (target gene) selected from the group consisting of a gene having a base sequence of SEQ ID NO.: 1, a gene having a base sequence of SEQ ID NO.: 2, a gene having a base sequence of SEQ ID NO.: 3, and homologous genes thereof; and (iv) determining the change in expression level of the target cell due to the administration of the test compound.

In accordance with one embodiment of the present invention, as the non-human animal, a non-human animal with pathological condition of a mental disorder is used.

In the screening method of the present invention, as the non-human animal, for example, a mouse is used. In this case, a gene having a base sequence of SEQ ID NO.: 1, a gene having a base sequence of SEQ ID NO.: 2, or a gene having a base sequence of SEQ ID NO.: 3 are to be the target genes.

In the preferable embodiment, the screening method of the present invention has an object to select and identify a compound that is effective for drug dependence.

Another aspect of the present invention relates to use of a mental disorder-related gene to the medial application. In this aspect, a method for obtaining information for diagnosing a mental disorder is provided. The method includes the steps of a) preparing a biological sample collected from a subject; and b) determining the expression level in the biological sample of a gene selected from the group consisting of a gene having a base sequence of SEQ ID NO.: 4, a gene having a base sequence of SEQ ID NO.: 5, a gene having a base sequence of SEQ ID NO.: 6 and natural mutants of these genes.

A further aspect of the present invention relates to use of mental disorder-related gene for treatment application. In this aspect, an antipsychotic drug including a compound for increasing the expression level in the target tissue of a gene selected from the group consisting of a gene having a base sequence of SEQ ID NO.: 4, a gene having a base sequence of SEQ ID NO.: 5, a gene having a base sequence of SEQ ID NO.: 6 and natural mutants of these genes is provided.

In one embodiment of the present invention, an active ingredient of the antipsychotic drug includes a compound selected from the group consisting of an isolated protein having an amino acid sequence of SEQ ID NO.: 10, an isolated protein having an amino acid sequence of SEQ ID NO.: 11, an isolated protein having an amino acid sequence of SEQ ID NO.: 12, natural mutants of these proteins, an isolated nucleic acid encoding the amino acid sequence of SEQ ID NO.: 10, an isolated nucleic acid encoding the amino acid sequence of SEQ ID NO.: 11, an isolated nucleic acid encoding the amino acid sequence of SEQ ID NO.: 12, and isolated nucleic acids encoding the mutants.

A further aspect of the present invention relates to use of mental disorder-related gene for research purposes. This aspect provides a reagent for studying a mental disorder, including an isolated nucleic acid having any one of the base sequences of SEQ ID NOs.: 1 to 6, or a kit including thereof.

The present invention further provides an expression vector for treating or studying a mental disorder, which holds nucleic acid encoding any one of the amino acid sequences of SEQ ID NOs.: 7 to 12. The present invention further provides an antibody to protein including any one of the amino acid sequences of SEQ ID NOs.: 7 to 12 for treating, diagnosing or studying mental disorders. In one preferable embodiment, the antibody of the present invention shows a specific binding property to peptide including an amino acid sequence of SEQ ID NO.: 19 or 20.

BRIEF DESCRIPTION OF THE DRAWINGS

FIG. 2 is a list of genes in which the expression is largely increased in the mouse nucleus accumbens as a result of the screening.

FIG. 3 shows a result of the BLAST search based on the base sequence of Gene 1. In the lower column, primers for specifically amplifying only a partial region are shown.

FIG. 4 shows a result of the BLAST search based on the base sequence of Gene 2. In the lower column, primers for specifically amplifying only a partial region are shown.

FIG. 7 shows the change of expression of Gene 2 mRNA after continuous administration of methamphetamine. After the final administration, the mice were subjected to decapitation (n=4-5).

was administered to mice for five days. Locomotor activity was measured for two hours. In the right cerebral ventricle (AP-0.5 mm, ML +1.0 mm from bregma, DV-2.0 mm from the skull), Gene 1 antisense oligonucleotide (Gene 1-AS, 1.8 nmol/6 μl/day), scramble control oligonucleotide (Gene 1-SC) and artificial cerebrospinal fluid (CSF) were infused continuously by using an osmotic pump. The results are shown in a mean value±standard error (n=5-7). In a repetitive two-way layout analysis of variance, a significant difference was observed. * P<0.05 compared with the physiological saline solution+CSF-treated group. # P<0.05 compared with the physiological saline solution+Gene 1-SC-treated group.

Figure 15:
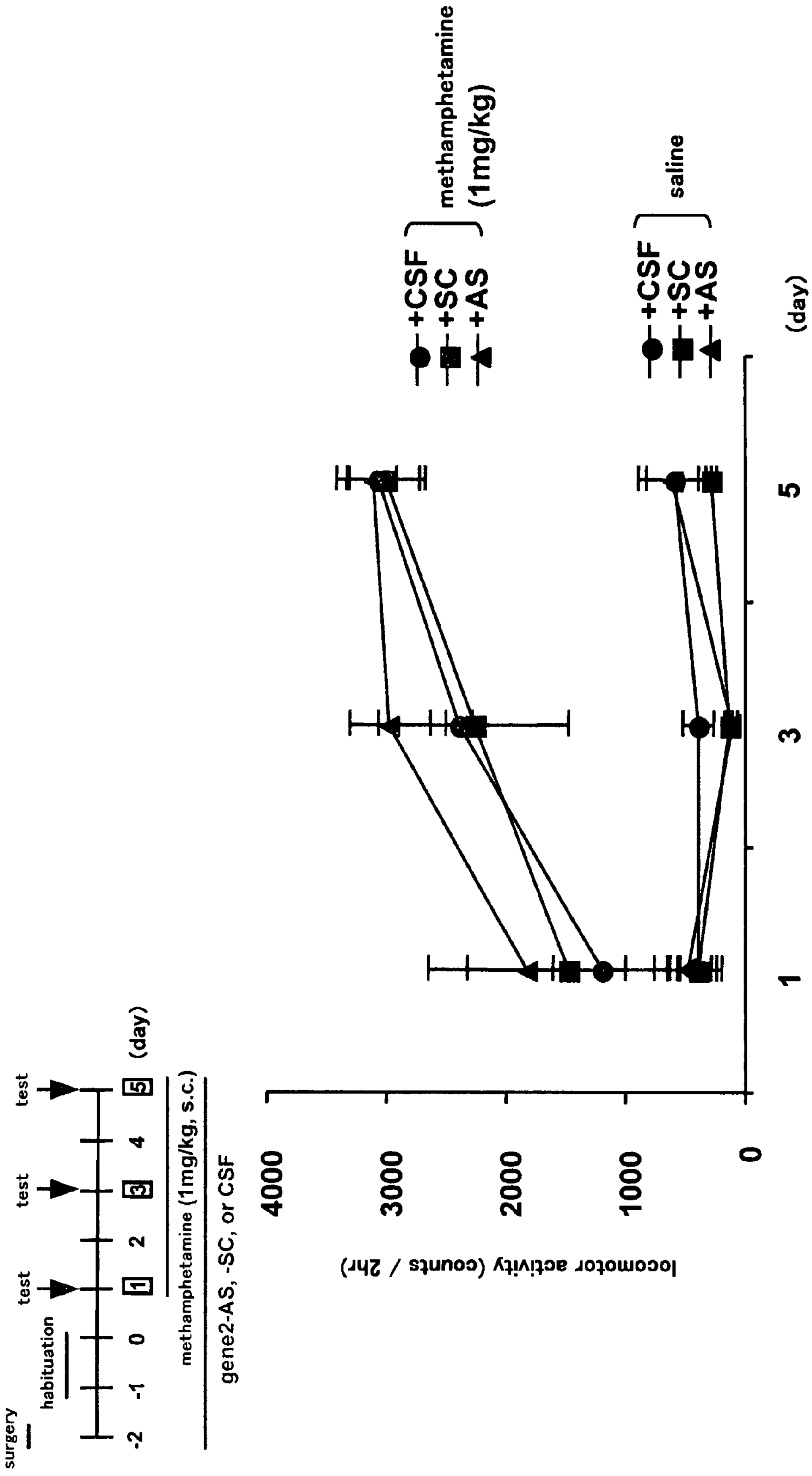

FIG. 15 is a view showing an effect of Gene 2 antisense oligonucleotide in the methamphetamine-induced enhancement of locomotor activity. Methamphetamine (1 mg/kg, s.c.) was administered to mice for five days. Locomotor activity was measured for two hours. In the right cerebral ventricle (AP-0.5 mm, ML +1.0 mm from bregma, DV-2.0 mm from the skull), Gene 2 antisense oligonucleotide (Gene 2-AS, 1.8 nmol/6 μl/day), scramble control oligonucleotide (Gene 2-SC) and artificial cerebrospinal fluid (CSF) were infused continuously by using an osmotic pump. The results are shown in a mean value±standard error (n=3-5).

Figure 16:
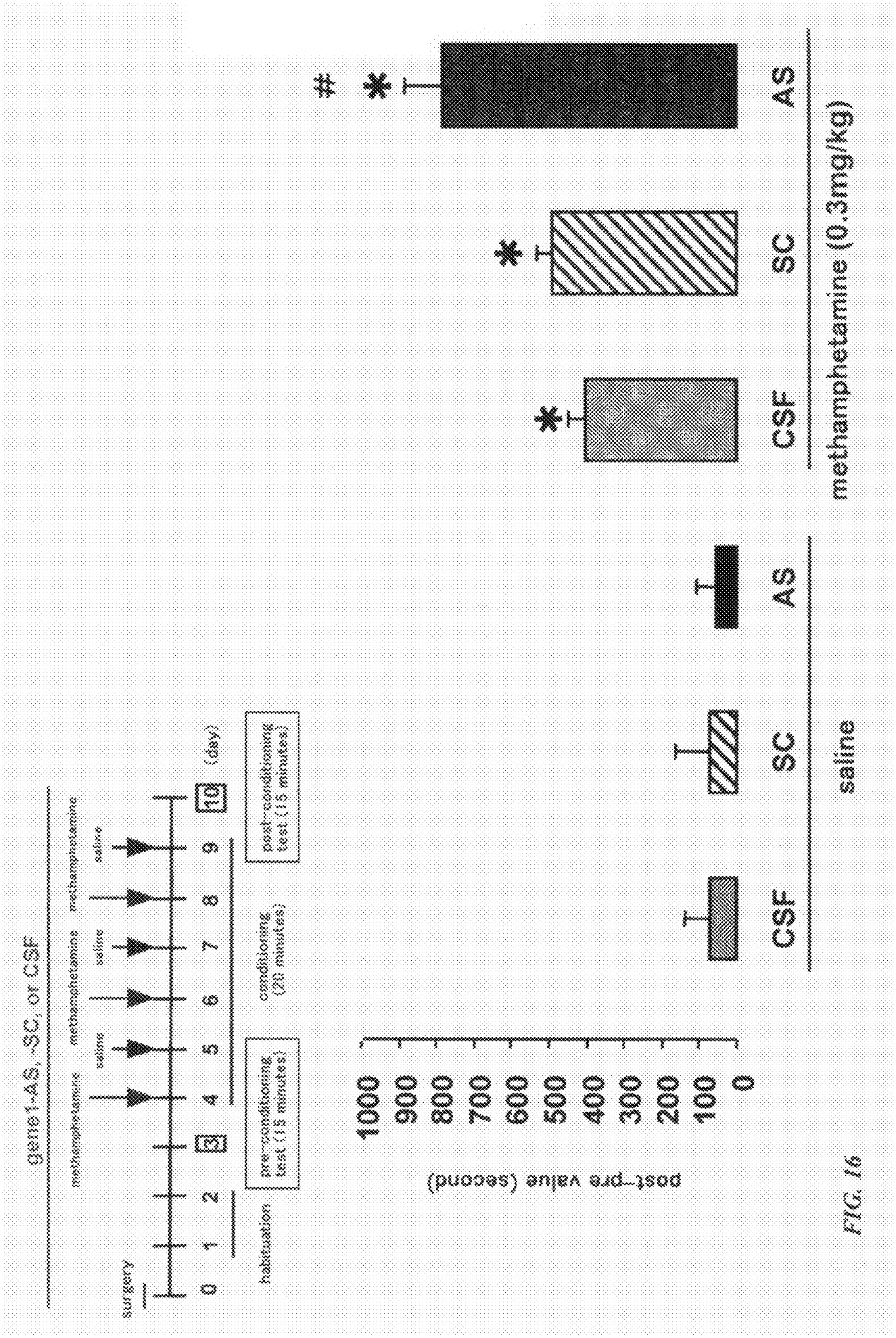

FIG. 16 is a view showing an effect of Gene 1 antisense oligonucleotide in the formation of the place preference by methamphetamine. During conditioning, methamphetamine (0.3 mg/kg, s.c.) or a physiological saline solution was administered to mice. In the right cerebral ventricle (AP-0.5 mm, ML +1.0 mm from bregma, DV-2.0 mm from the skull), Gene 1 antisense oligonucleotide (Gene 1-AS, 1.8 nmol/6 μl/day), scramble control oligonucleotide (Gene 1-SC) and artificial cerebrospinal fluid (CSF) are infused continuously by using an osmotic pump. The results are shown in a mean value±standard error (n=5-12). * P<0.05 compared with the physiological saline solution-treated group. # P<0.05 compared with the methamphetamine+CSF-treated group and a methamphetamine+Gene 1-SC-treated group.

Figure 17:
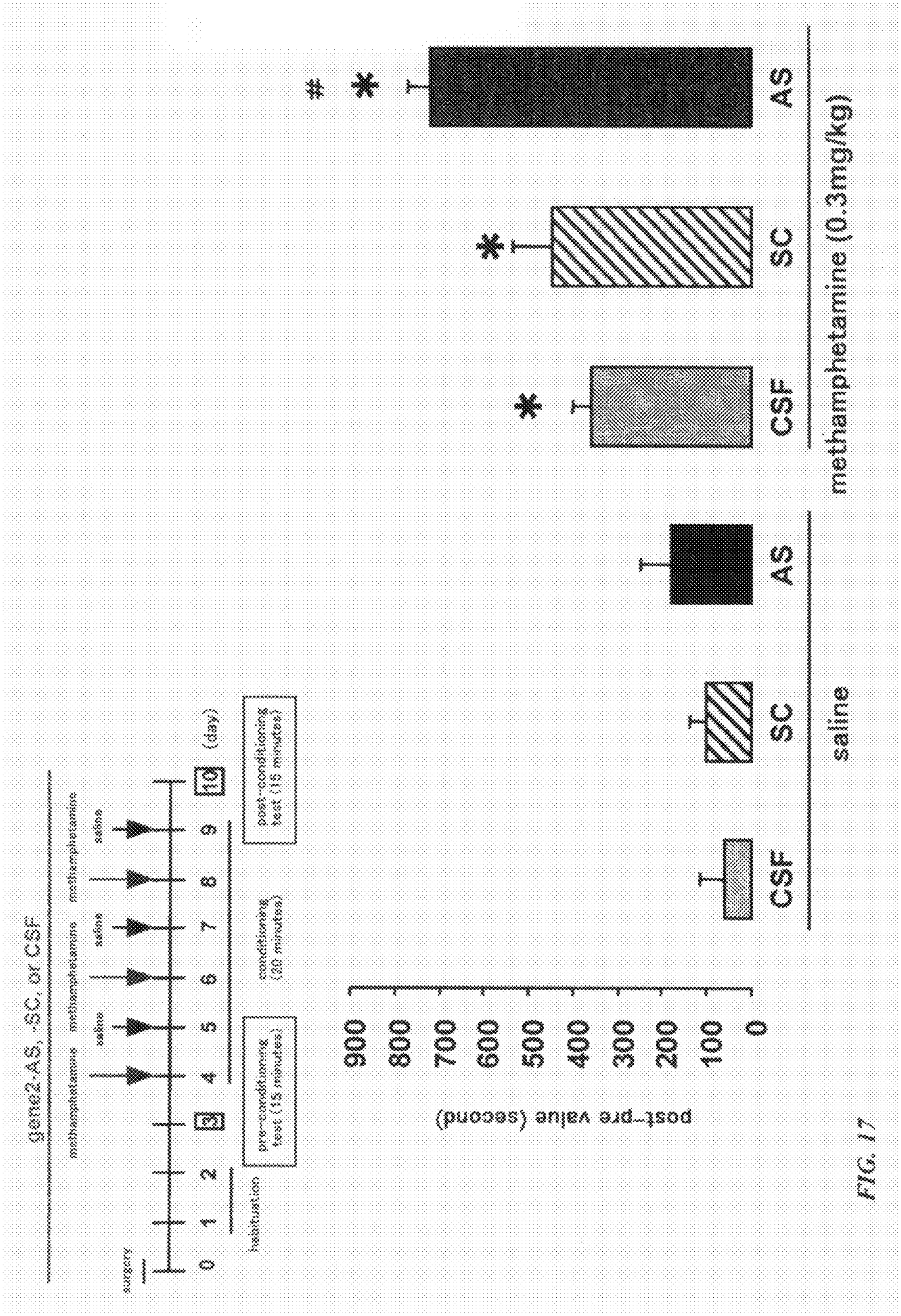

FIG. 17 is a view showing an effect of Gene 2 antisense oligonucleotide in the formation of the place preference by methamphetamine. During conditioning, methamphetamine (0.3 mg/kg, s.c.) or a physiological saline solution was administered to mice. In the right cerebral ventricle (AP-0.5 mm, ML +1.0 mm from bregma, DV-2.0 mm from the skull), Gene 2 antisense oligonucleotide (Gene 1-AS, 1.8 nmol/6 μl/day), scramble control oligonucleotide (Gene 2-SC) and artificial cerebrospinal fluid (CSF) are infused continuously by using an osmotic pump. The results are shown in a mean value±standard error (n=4-8). * P<0.05 compared with the physiological saline solution-treated group. # P<0.05 compared with the methamphetamine+CSF-treated group.

Figure 18:
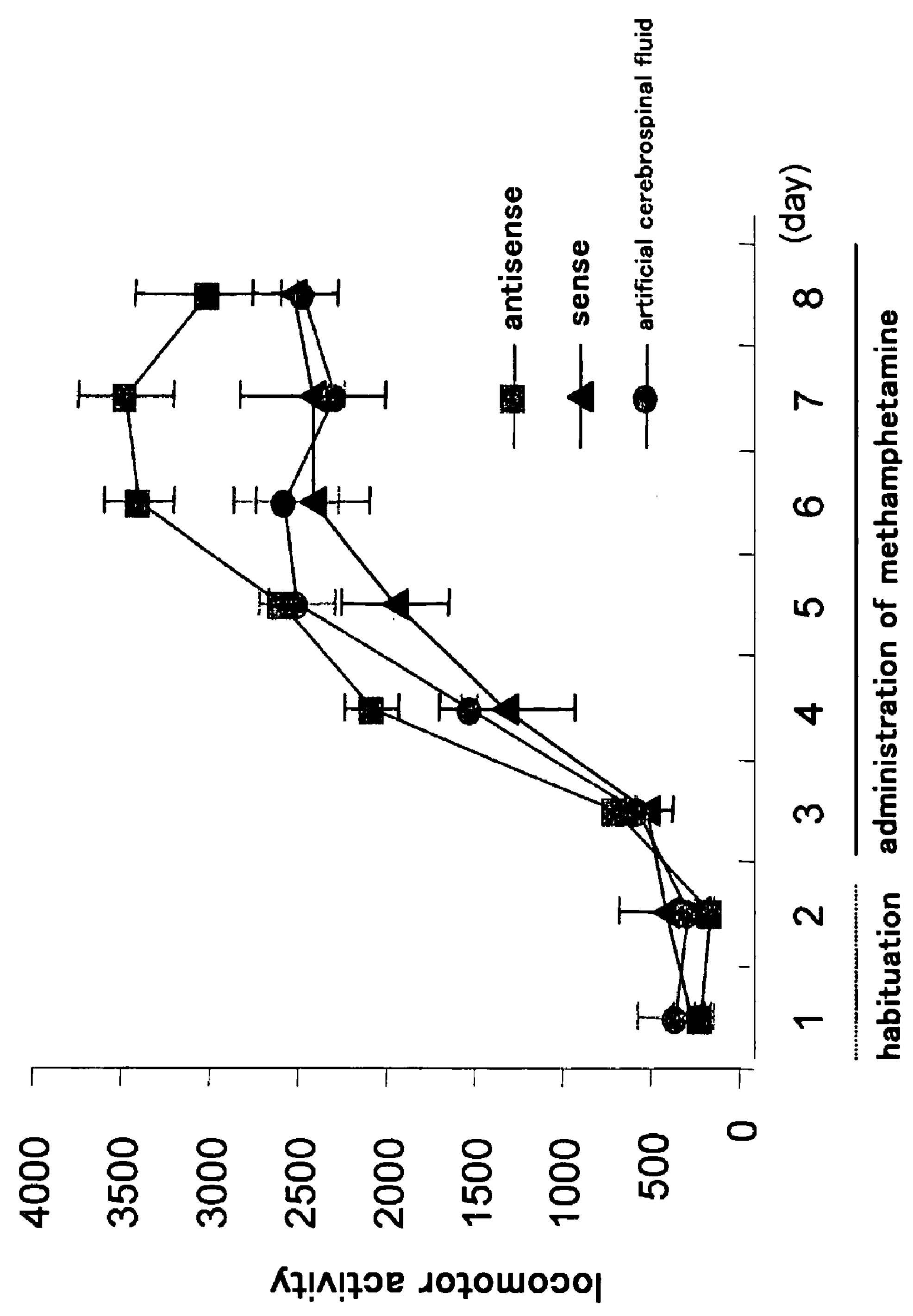

FIG. 18 shows an influence of endogenous Piccolo (Gene 3) on the reverse tolerance of methamphetamine inducing property. Piccolo antisense oligonucleotide (antisense concentration: 0.6 nmol/6 μl/day), sense oligonucleotide (antisense concentration: 0.6 nmol/6 μl/day) and artificial cerebrospinal fluid were continuously infused in the cerebral ventricle by using an osmotic mini-pump. The site to be administered is a site that is 0.5 mm posterior and 1 mm left from the bregma, depth was made to be 2 mm. Methamphetamine was administered for six days. The number of individuals was 4 to 5.

Figure 19:
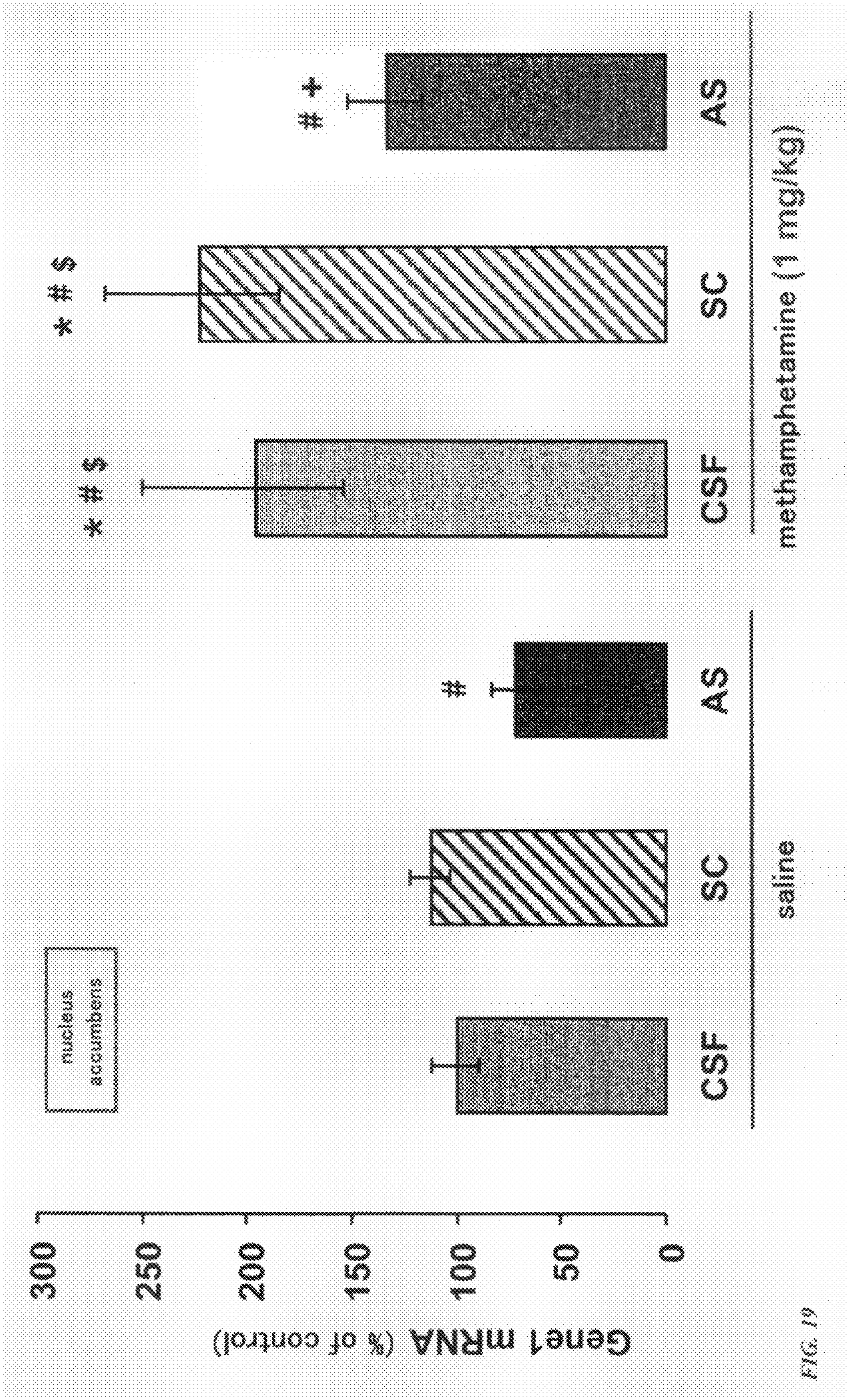

FIG. 19 shows the change in the expression of Gene 1 mRNA by the continuous administration of methamphetamine in a mouse to which Gene 1 antisense oligonucleotide was infused. * P<0.05 compared with the physiological saline solution+CSF-treated group. # P<0.05 compared with the physiological saline solution+Gene 1-SC-treated group. $ P<0.05 compared with the physiological saline solution+Gene 1-AC-treated group. + P<0.05 compared with the methamphetamine+Gene 1-SC-treated group.

Figure 20:
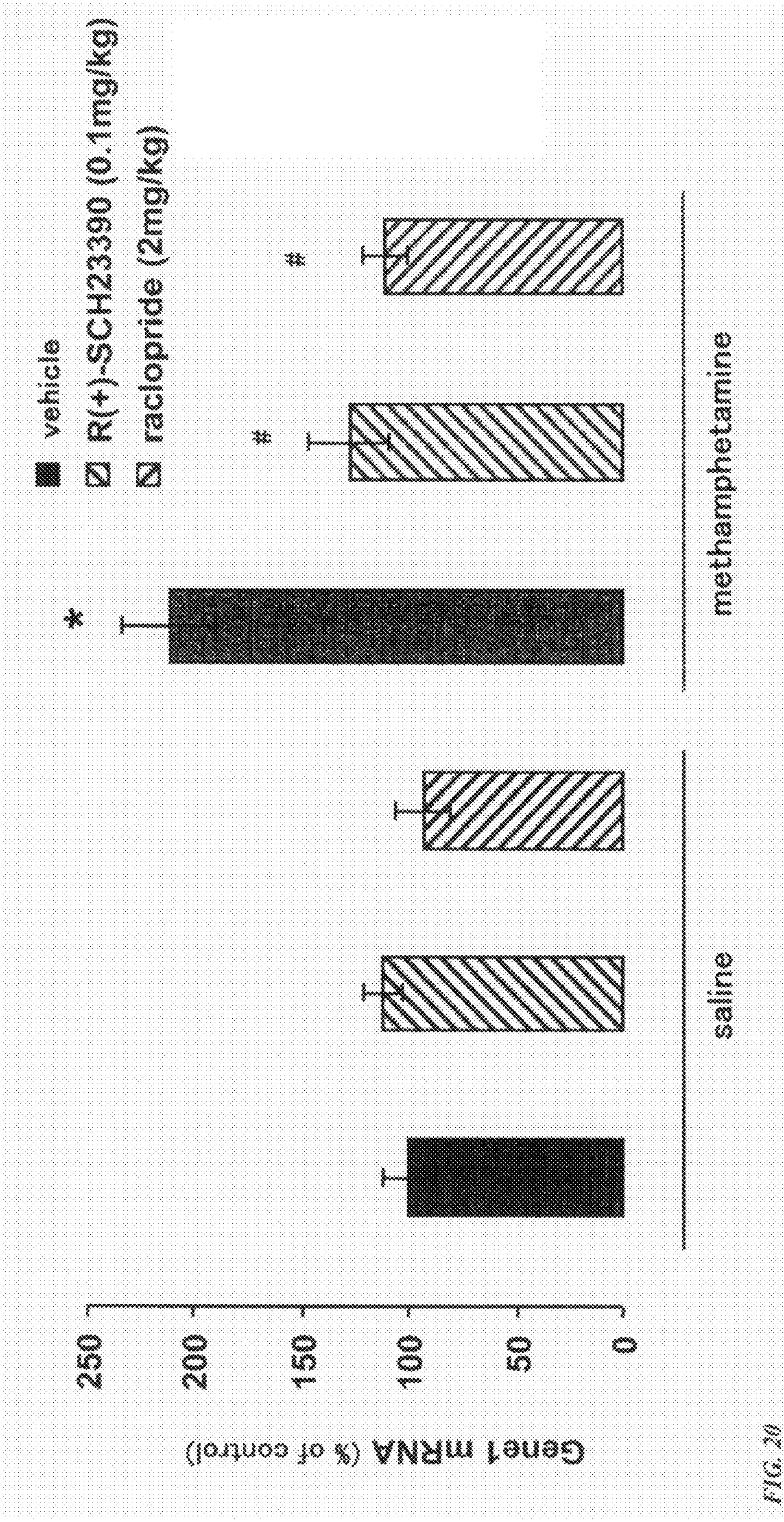

FIG. 20 shows an effect of dopamine D1 receptor antagonist R(+)-$SCH_{23390}$ and dopamine D2 receptor antagonist raclopride in the increase in the expression of Gene 1 mRNA in the nucleus accumbens induced by methamphetamine. * P<0.05 compared with the vehicle/physiological saline solution-administered group. # P<0.05 compared with the vehicle/methamphetamine-administered group.

Figure 21:
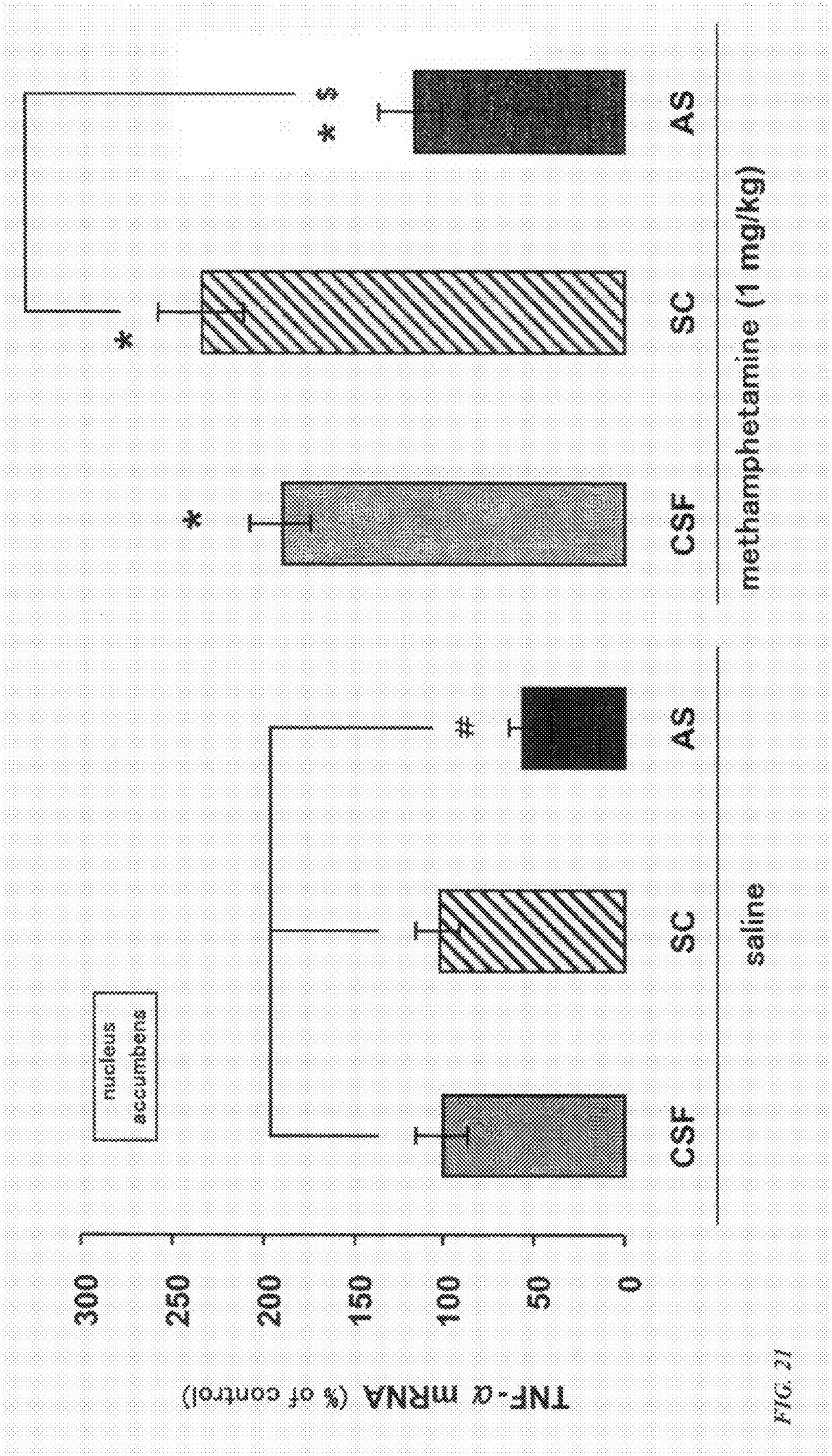

FIG. 21 shows the change in the expression of TNF-α mRNA by the continuous administration of methamphetamine in a mouse to which Gene 1 antisense oligonucleotide was infused. * P<0.05 compared with the physiological saline solution+CSF-treated group. # P<0.05 compared with the physiological saline solution+Gene 1-SC-treated group. * P<0.05 compared with the physiological saline solution+CSF-treated group. # P<0.05 compared with the methamphetamine+Gene 1-SC-treated group.

Figure 22:
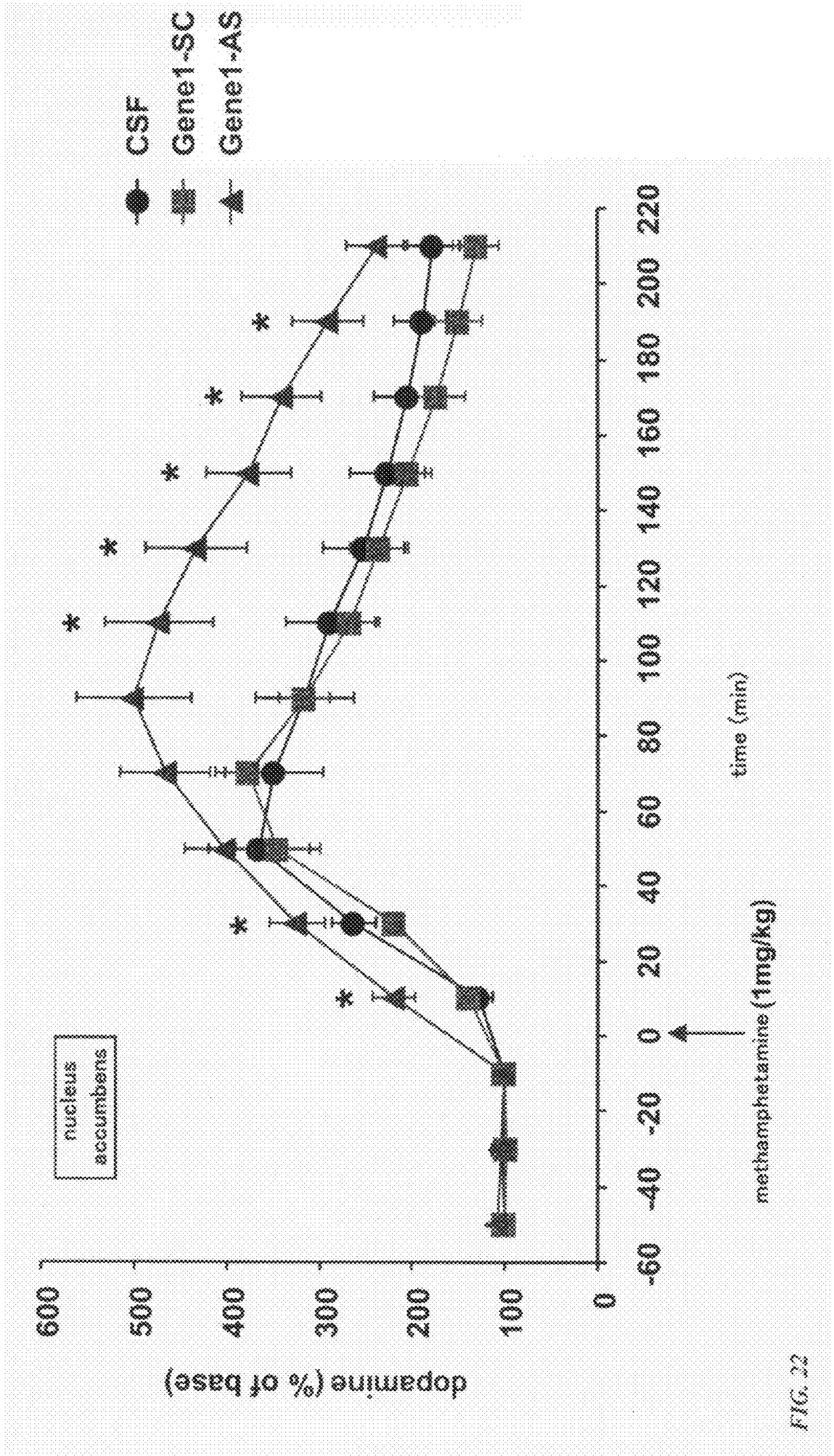

FIG. 22 shows an in vivo effect of Gene 1 antisense oligonucleotide in the increase of the amount of extracellular dopamine induced by methamphetamine. * P<0.05 compared with the Gene 1-SC-infused group.

Figure 23:
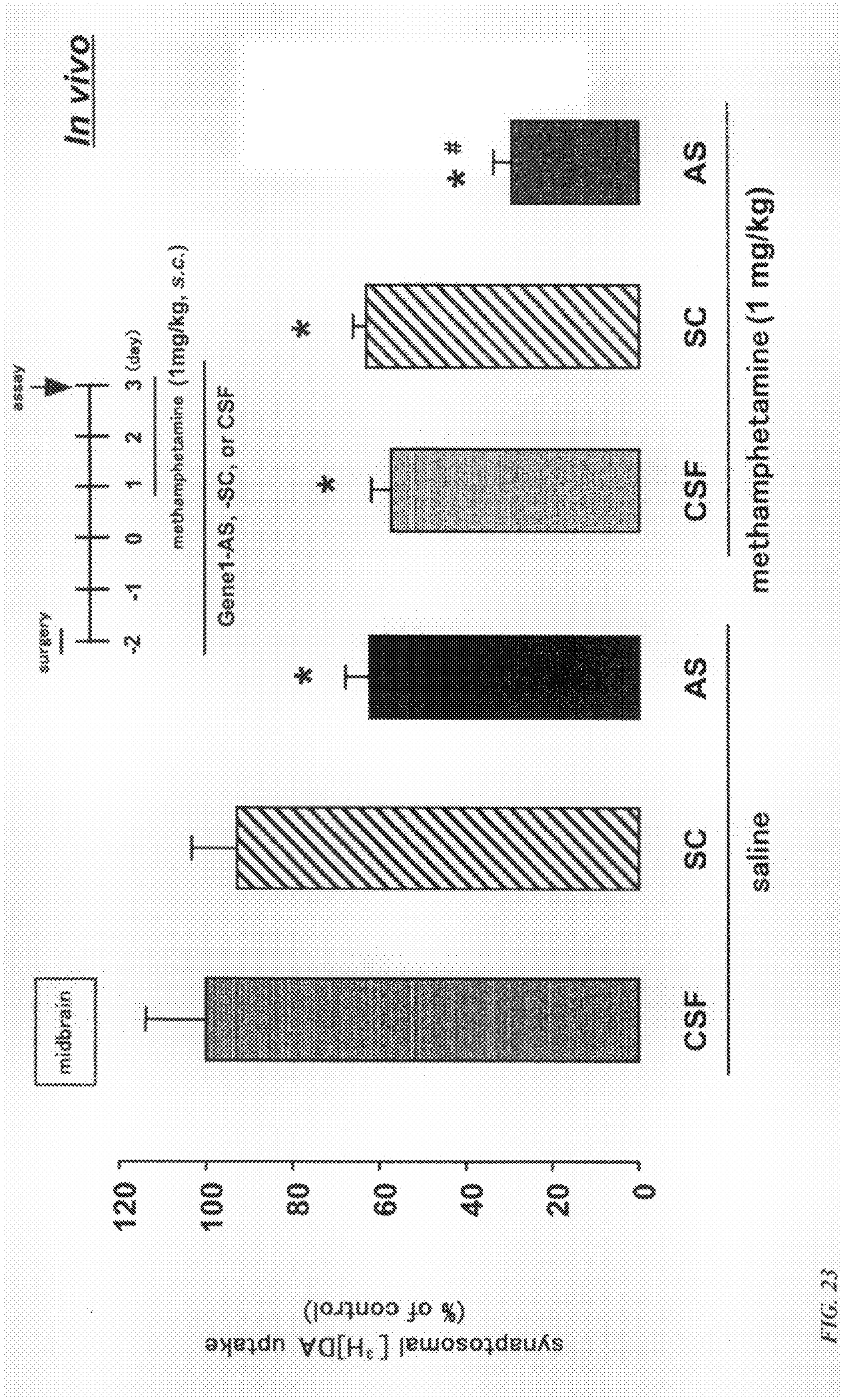

FIG. 23 shows an effect of Gene 1 in the reduction of the uptake of synaptosomal [$^3$H]DA induced by methamphetamine. * P<0.05 compared with the physiological saline solution+CSF-infused group. # P<0.05 compared with the methamphetamine+Gene 1-SC-infused group.

Figure 24:
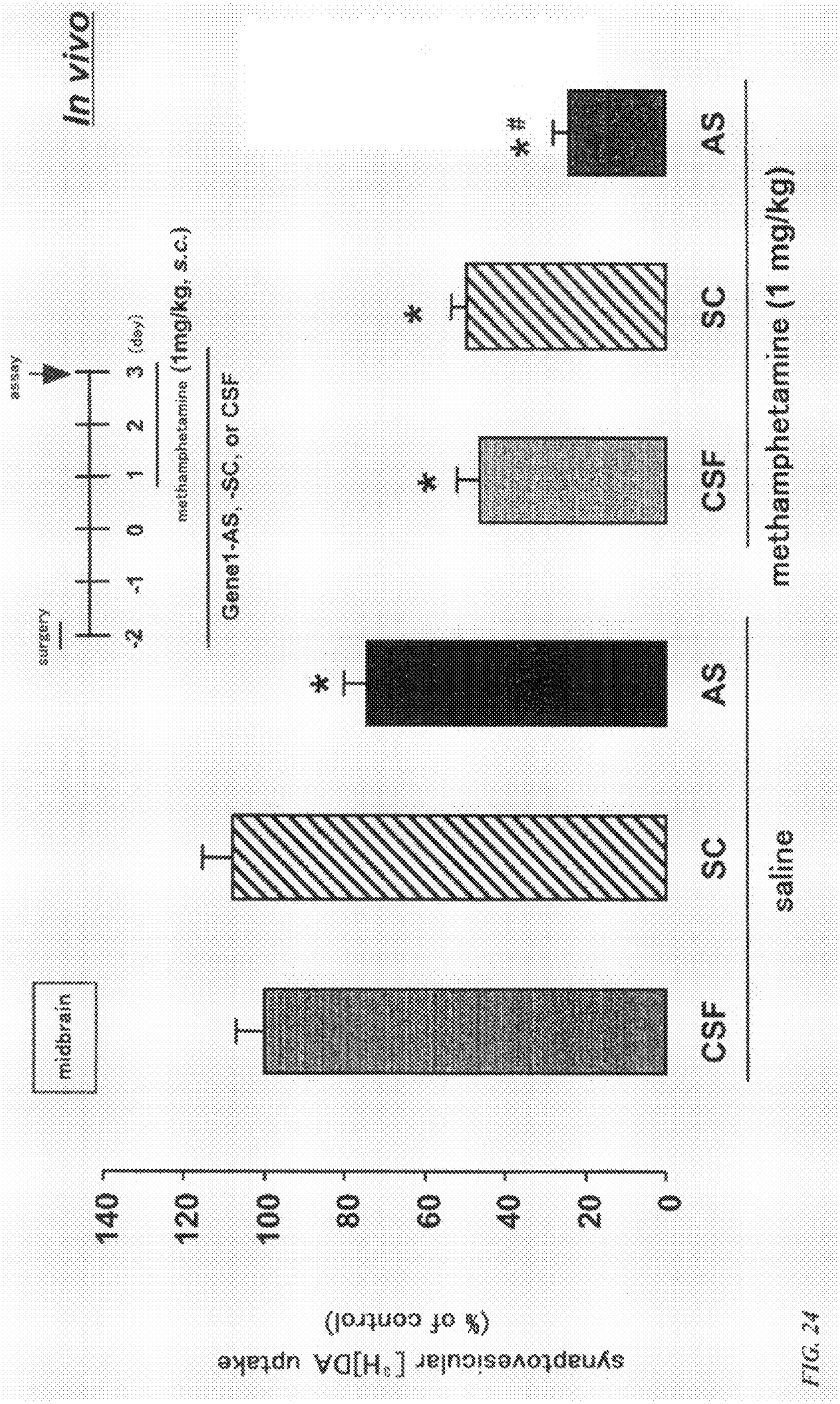

FIG. 24 shows an effect of Gene 1 in the reduction of the uptake of synaptovesicle [$^3$H]DA induced by methamphetamine. * P<0.05 compared with the physiological saline solution+CSF-infused group and physiological saline solution+Gene 1-SC-treated group. # P<0.05 compared with the methamphetamine+Gene 1-SC-infused group.

Figure 25:
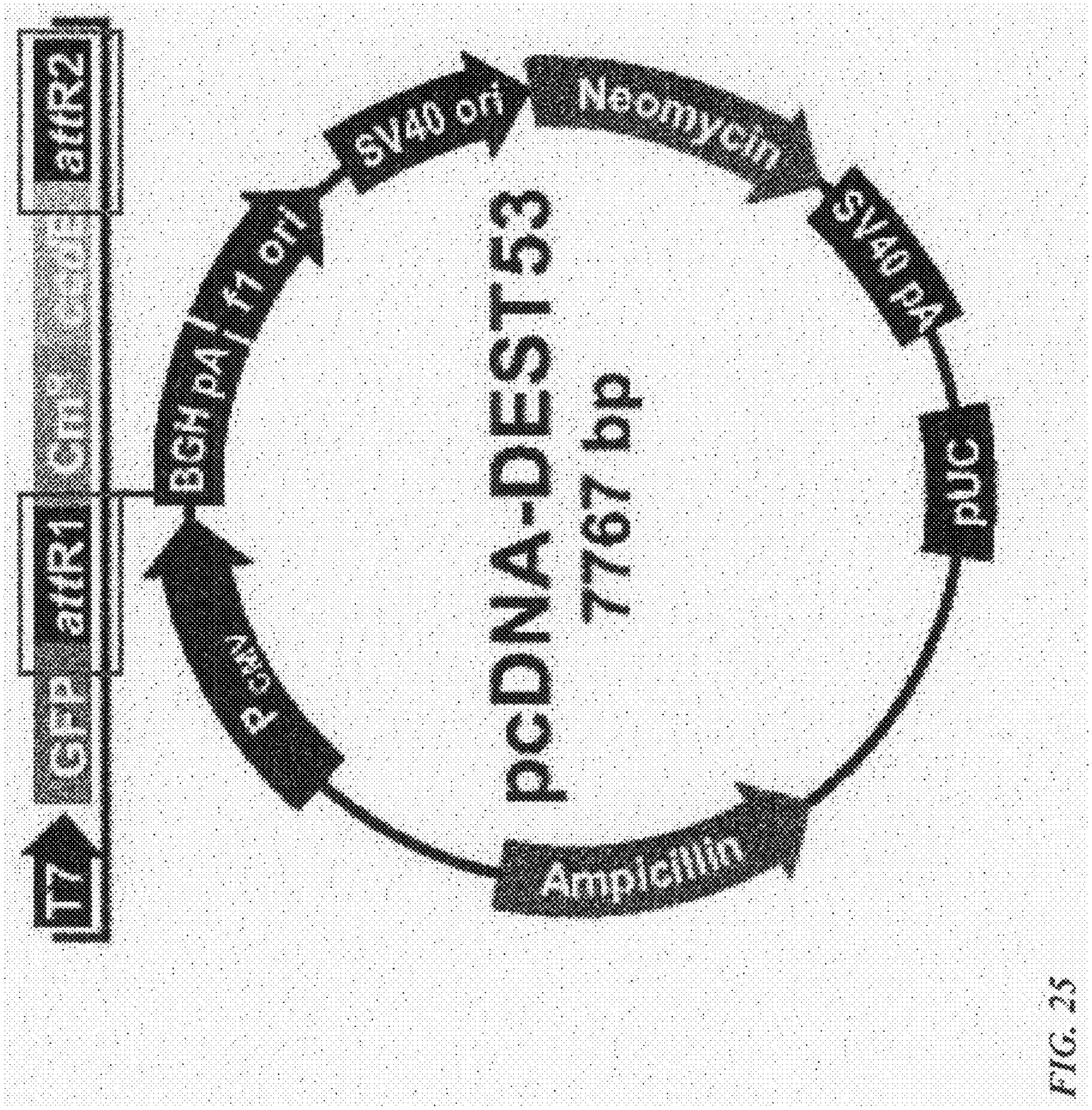

FIG. 25 shows a configuration of an expression vector (pcDNA-DEST53) used in expression experiment of the full length or a fragment of Gene 1. Regions of the base numbers 1650 and 3312 are replaced by Gene 1 DNA (full length or fragment). Into the site of attR1, any one of base numbers 1643 to 1767 and base numbers 3202 to 3326.

Figure 26:
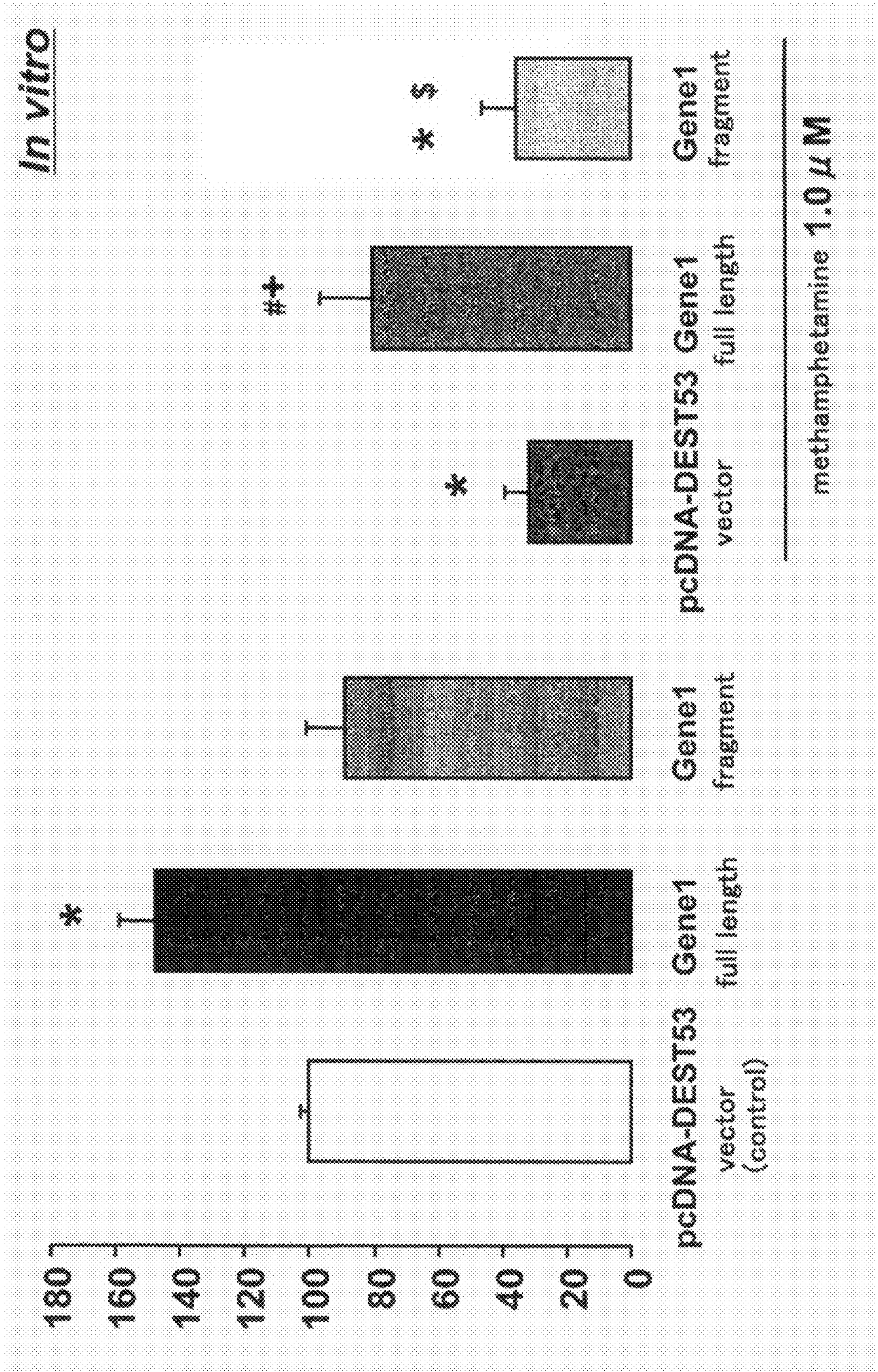

FIG. 26 shows an effect of transfected Gene 1 in the reduction of the uptake of [$^3$H]DA induced by methamphetamine. * P<0.05 compared with pcDNA-DEST53 vector introduced cell. # P<0.05 compared with full length Gene 1-introduced cell. $ P<0.05 compared with Gene 1 fragment introduced cell. + P<0.05 compared with methamphetamine+pcDNA-DEST53 vector introduced cell.

Figure 27:
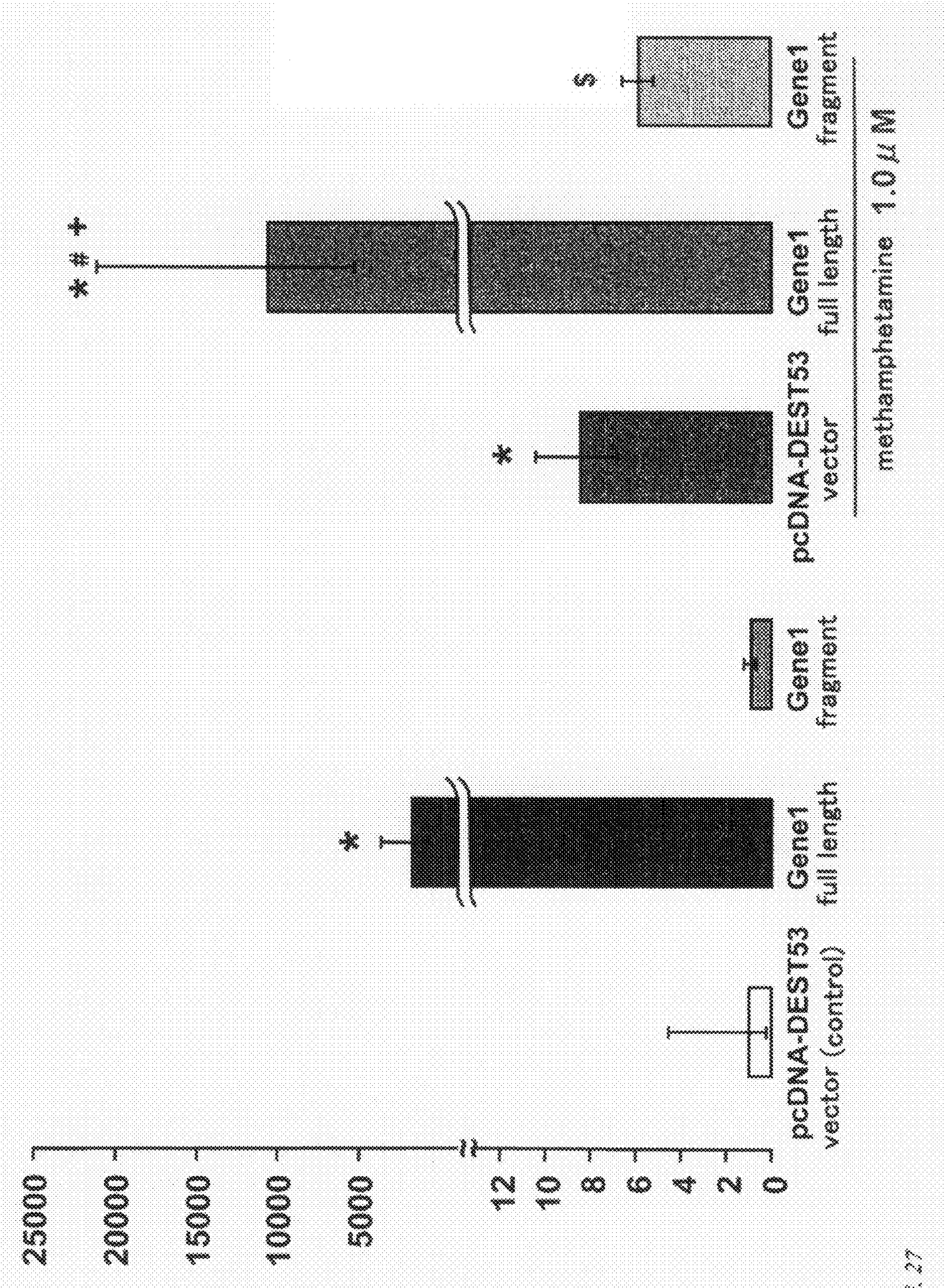

FIG. 27 shows the change in the expression of Gene 1 mRNA after methamphetamine is acted in the PC 12 cell into which the full-length Gene 1 expression vector has been introduced. Into the PC12 cell, by using Lipofectamine, an expression vector for expressing the full length Gene 1, an expression vector for expressing the Gene 1 fragment or a pcDNA-DEST vector (empty vector) is transfected. In a 24-well plate, cells were cultured for 2 to 3 days, and then pre-treated with methamphetamine (1.0 μM) for 30 minutes. Thereafter, the expression level of Gene 1 mRNA in the cell was measured by a RT-PCR method. The results are shown in a mean value±standard error (n=8). * P<0.05 compared with pcDNA-DEST53 vector treated cells, # P<0.05 compared with full-length Gene 1 treated cells, $ P<0.05 compared with Gene 1 fragment treated cells, and + P<0.05 compared with methamphetamine+pcDNA-DEST53 vector treated cells.

Figure 28:
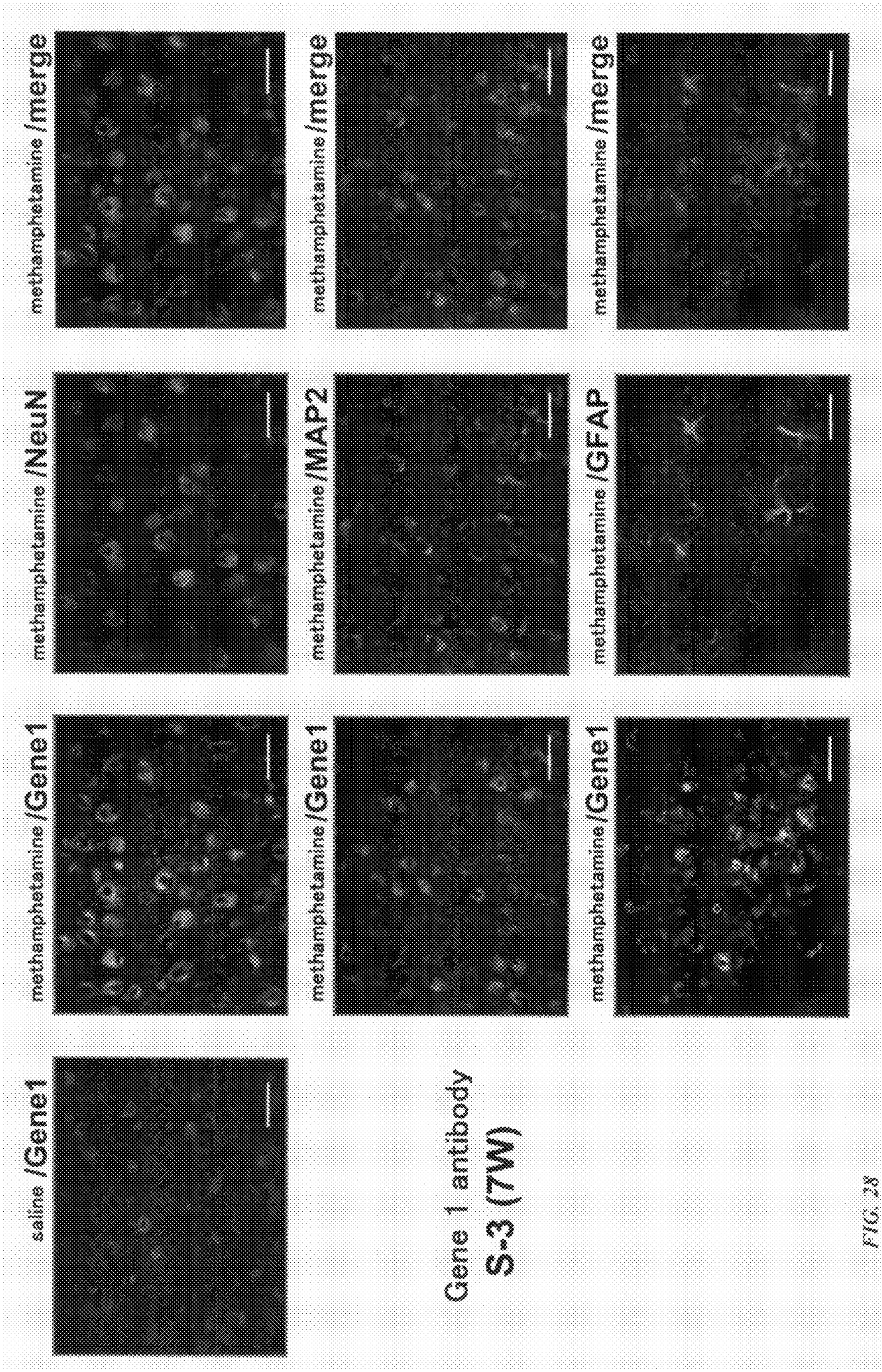

FIG. 28 shows the localization of Gene 1 in the nucleus accumbens after the continuous administration of methamphetamine. Methamphetamine (2 mg/kg, s.c.) was administered to mice for six days, and 24 hours after the final administration, the mice were subjected to decapitation. The nucleus accumbens was immuno-stained with a polyclonal antibody to a partial peptide encoded by Gene 1. Methamphetamine/Gene 1 is a result of staining by using a polyclonal antibody to Gene 1 partial peptide. Furthermore, methamphetamine/NeuN is a result of staining with an anti-NeuN (nerve cell marker) antibody; methamphetamine/MAP2 is a result of staining with an anti-MAP2 (nerve cell marker) antibody, and methamphetamine/GFAP is a result of staining with an anti-GFAP (glia cell marker). Pictures of methamphetamine/merge in the right column show a merge of two pictures showing the results of staining, respectively. Scale bar: 20 μm.

Figure 29:
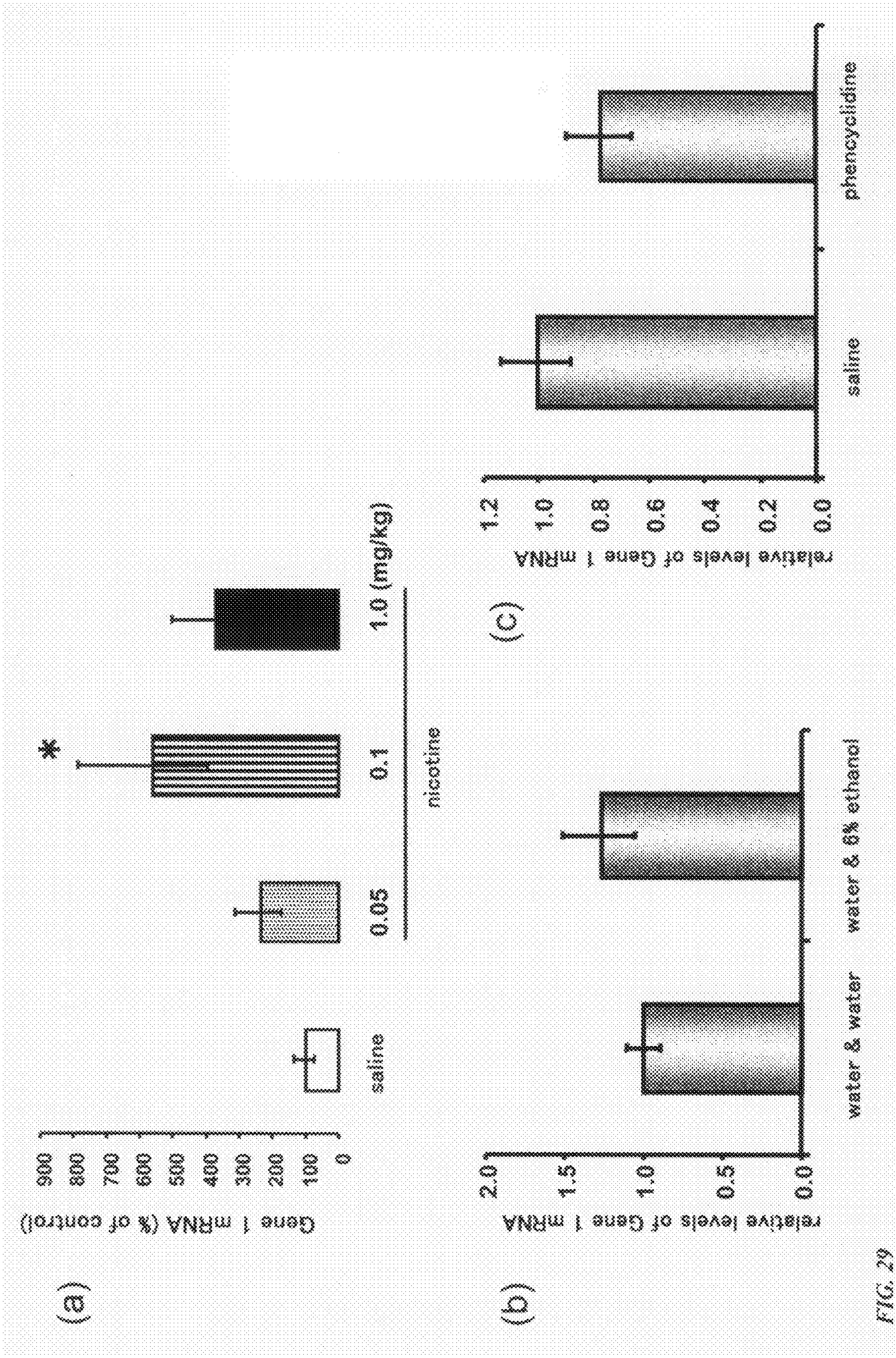

FIG. 29 shows the change in expression of Gene 1 mRNA in nicotine, alcohol and phencyclidine. * $P<0.05$ compared with the physiological saline solution-administered group.

Figure 30:
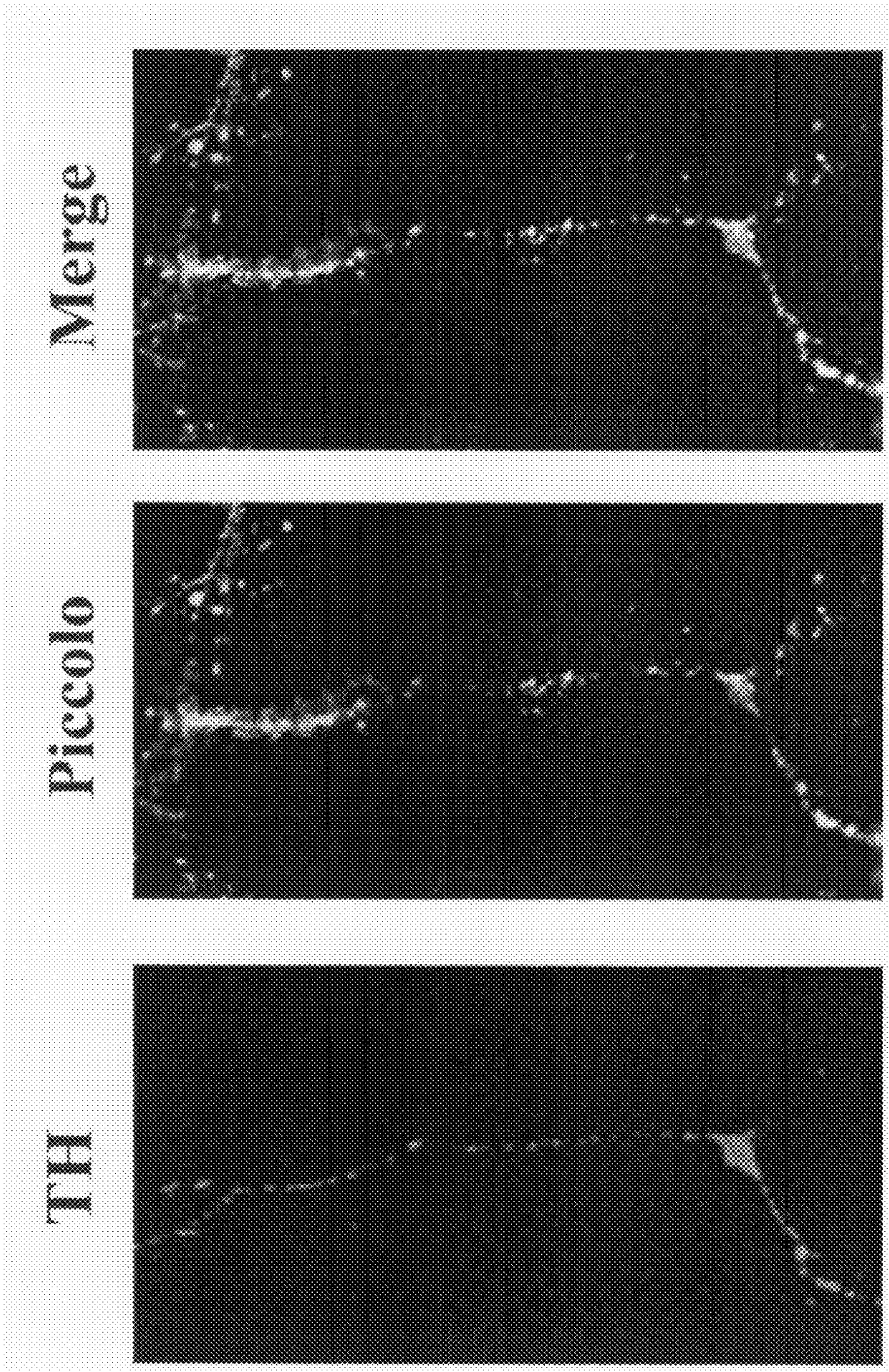

FIG. 30 shows the expression of Piccolo protein in a nerve cell. TH: immunostaining image using an anti-TH (tyrosine hydroxylase) antibody, Piccolo: immunostaining image using an anti-Piccolo antibody, and Merge: merge of two images at the left side.

Figure 31:
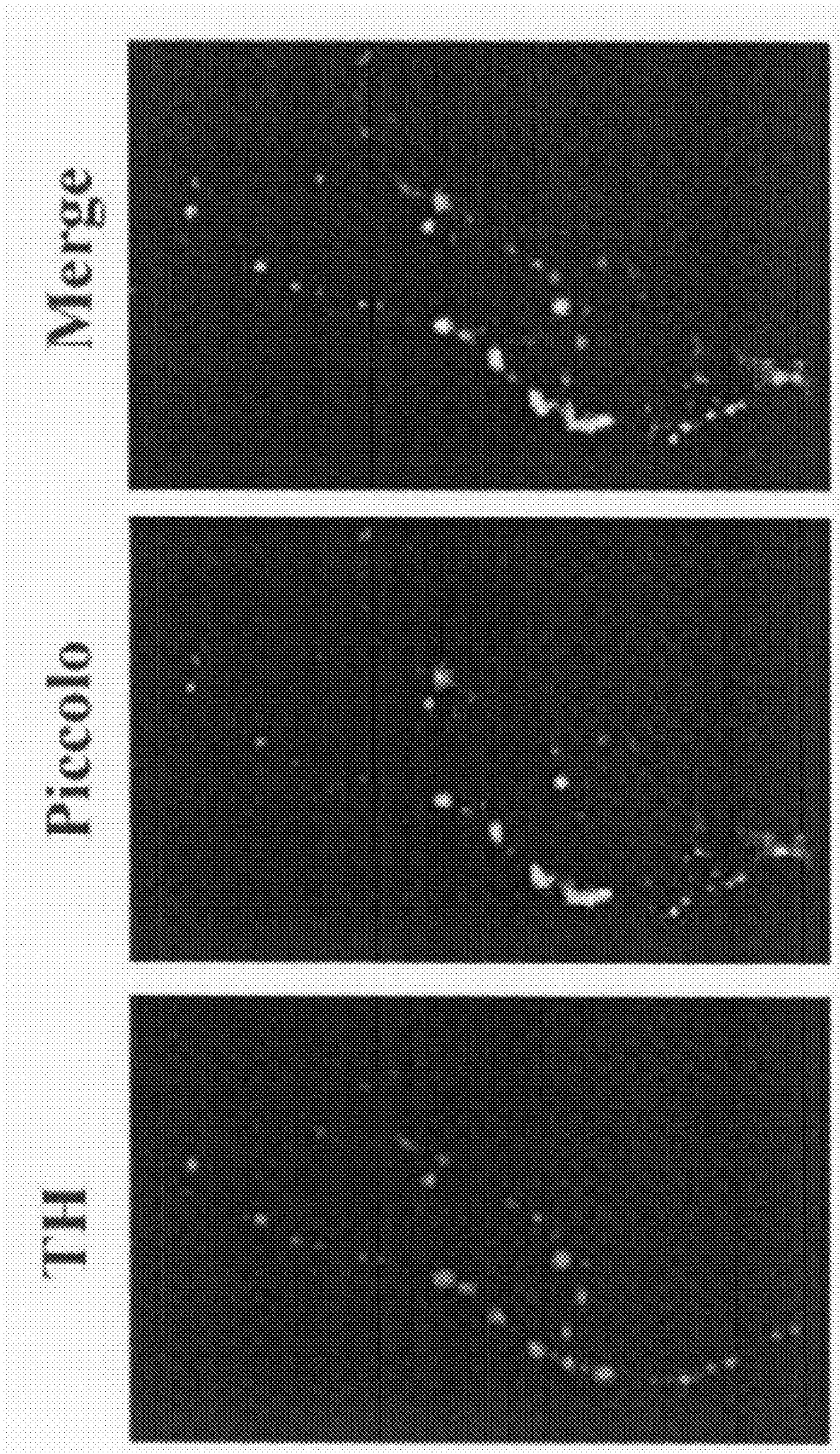

FIG. 31 shows the expression of Piccolo protein in the anterior ganglion of midbrain dopamine neuron. TH: immunostaining image using an anti-TH (tyrosine hydroxylase) antibody, Piccolo: immunostaining image using an anti-Piccolo antibody, and Merge: merge of two images shown in the left side.

Figure 32:
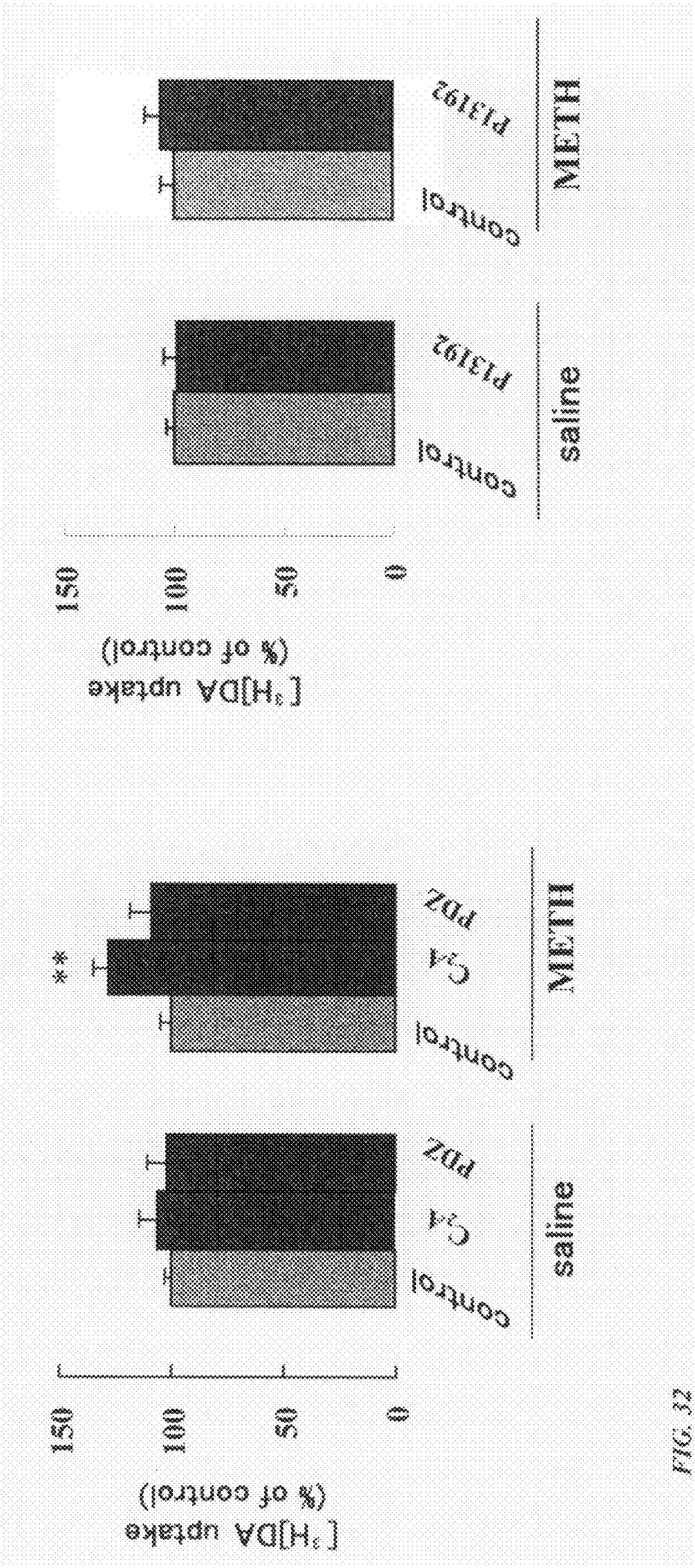

FIG. 32 shows an effect of a Piccolo C2A domain on the suppression of uptake of dopamine in the PC12 cell in which a human dopamine transporter has been forcedly expressed.

Figure 33:
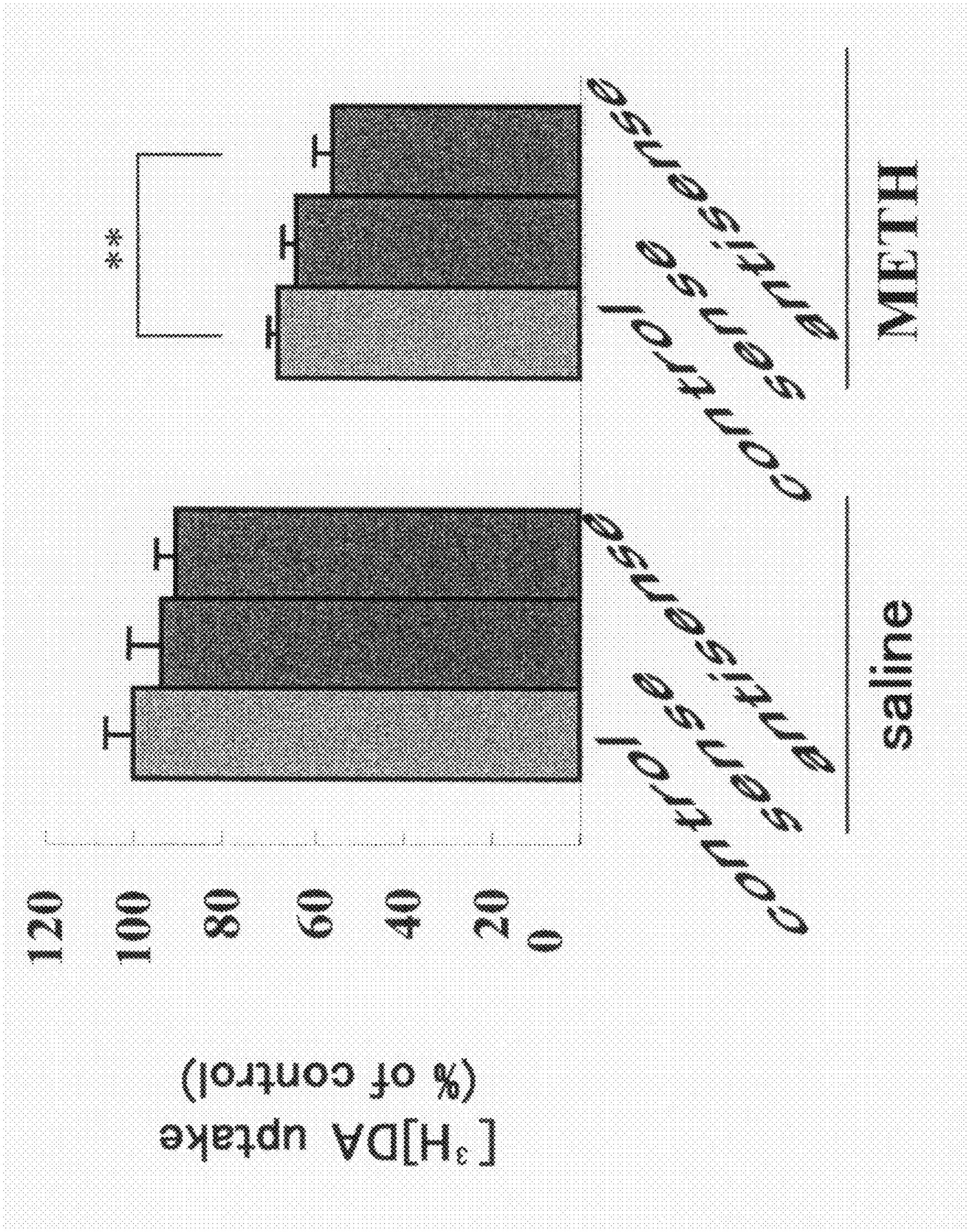

FIG. 33 shows an effect of the suppression of the expression of Piccolo in the PC12 cell in which a human dopamine transporter has been forcedly expressed.

Figure 34:
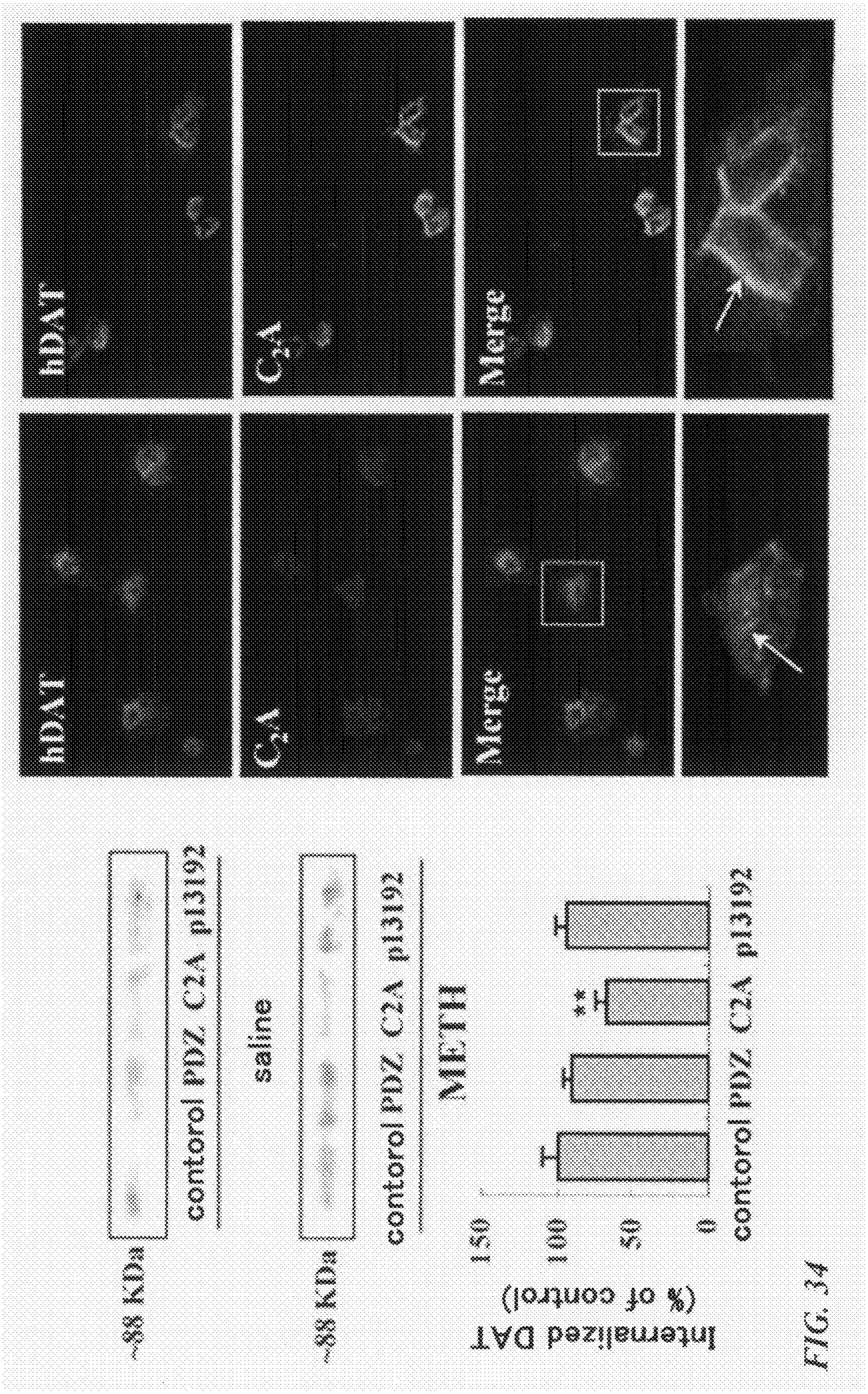

FIG. 34 shows an effect of Piccolo on the intracellular movement of the dopamine transporter by methamphetamine.

Figure 35:
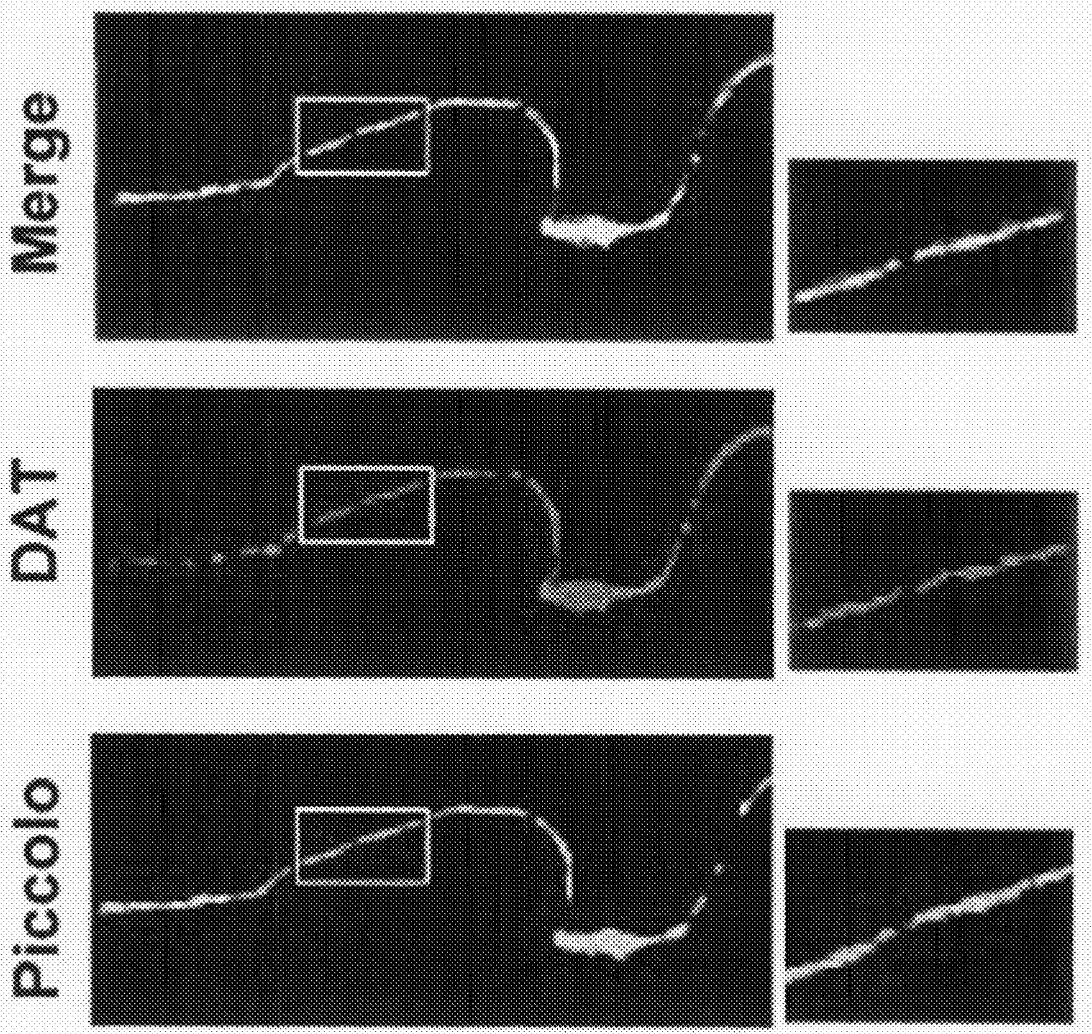

FIG. 35 shows a localization of piccolo in the dopaminergic nerve cell.

Figure 36:
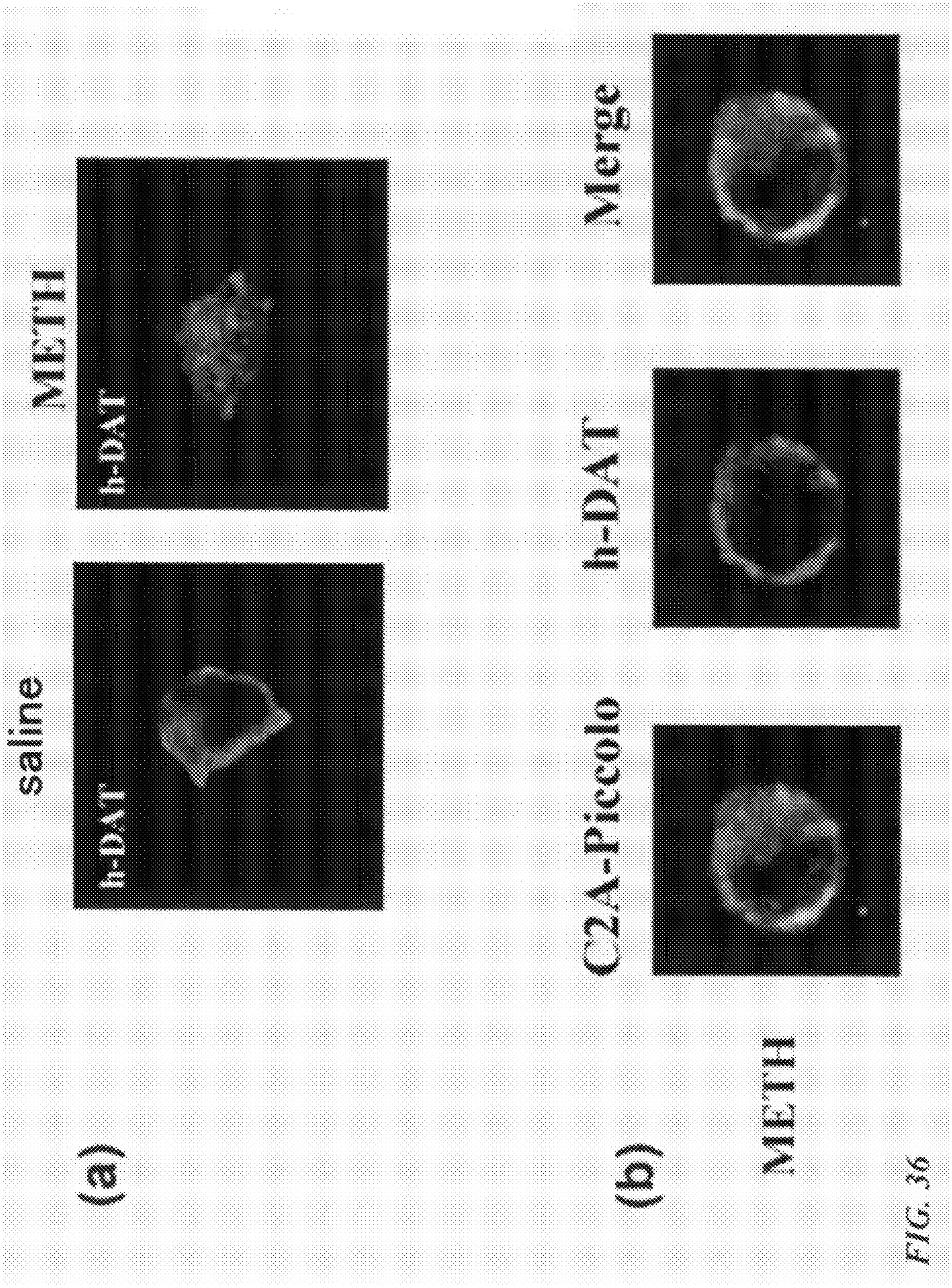

FIG. 36 is a view summarizing the relation between the dopamine transporter between Piccolo protein in the PC12 cell. When methamphetamine is acted, the internalization of the dopamine transporter occurs (FIG. 36(*a*)). Furthermore, the C2A domain of the dopamine transporter and Piccolo are expressed in the same location (FIG. 36(*b*)).

BEST MODE FOR CARRYING OUT THE INVENTION

A mental disorder is generally classified into endogenous mental disorders (schizophrenic disorder and the like), exogenous mental disorders, organic mental disorders (dementia and the like), symptomatic mental disorders (mood swing and the like), toxic mental disorders (alcohol dependence, drug dependence, and the like), and psychogenic mental disorders (neurosis, psychosomatic disease, and the like) according to causes of disease. Preferably, the present invention is directed to endogenous mental disorders and toxic mental disorders. Further preferably, the present invention is directed to schizophrenic disorder that is one example of the endogenous mental disorders or drug dependence that is one example of the toxic mental disorder. Most preferably, the present invention is directed to preference drug dependence among the drug dependence. Depending upon the cause drugs, the drug dependence is characterized by psychic dependence that is dependence on a psychic action (effect) of drug, physical dependence for avoiding the biological response to drug withdrawal, or obtaining of tolerance (or combination thereof). An example of the cause drug of the drug dependence include methamphetamine, morphine, cocaine, nicotine, alcohol, phencyclidine, benzodiazepine, and the like (including each kind of salt). The drug dependence of the present invention is not limited to the drug dependence relating to these drugs.

In the present specification, "antipsychotic drug" refers to as drugs used for suppressing the onset of a mental disorder, or drugs used for reducing the symptoms of a mental disorder (including partial or complete healing). Therefore, the antipsychotic drugs of the present invention include drugs that can be used for preventive treatment of mental disorders and drugs that can be used for treating the mental disorders.

When the present invention refers to a gene, the natural mutant thereof may be contemplated.

(Screening Method)

One aspect of the present invention provides a method for screening a compound effective for a mental disorder. A compound selected by the screening method of the present invention is expected to be effective for medical measurement relating to mental disorders. That is to say, the compound selected by the screening method of the present invention becomes a promising candidate for drugs for mental disorders or a material useful in developing such drugs. When the selected compound has a sufficient drug efficacy with respect to mental disorders, an intact compound can be used as an active ingredient of drugs. On the other hand, when the selected compound does not have a sufficient drug efficacy, the compound can be used after the drug efficacy thereof is enhanced by subjecting the compound to modification such as chemical modification. Needless to say, even when the compound has a sufficient drug efficacy, it may be modified for the purpose of increasing the drug efficacy.

The screening method of the present invention can be carried out by using certain cells or animal individuals.

(Cell-Based Screening Method)

One embodiment of the present invention provides a method for cell-based screening. In this embodiment, whether or not the expression level of a certain gene in the cell is changed is examined by exposing (administering and adding) a test compound to the cell. Specifically, the screening method of the present invention carries out the following steps.

Step 1: preparing a cell capable of expressing a gene (target gene) selected from the group consisting of a gene having a base sequence of SEQ ID NO.: 1, a gene having a base sequence of SEQ ID NO.: 2, a gene having a base sequence of SEQ ID NO.: 3 and homologous genes thereof.

Step 2: exposing the cell to a test compound.

Step 3: determining the expression level of the target gene in the cell after the exposure to the test compound.

Step 4: determining the change in expression level of the target gene due to the exposure to the test compound.

Hereinafter, the detail for each step is described.

1. Step 1

In the step 1, a cell expressing a gene to be detected (which is referred to as "target gene" in the specification) is prepared. The target gene can be selected from a gene having a base sequence of SEQ ID NO.: 1 (which is also referred to as "target mouse gene 1" in the specification), a gene having a base sequence of SEQ ID NO.: 2 (which is also referred to as "target mouse gene 2" in the specification), a gene having a base sequence of SEQ ID NO.: 3 (which is also referred to as "target mouse gene 3" in the specification), and homologous genes thereof. Two kinds or more of genes may be a detection target. Note here that all of the target mouse genes 1 to 3 are mouse genes in which the relationship with respect to drug dependence has been observed (see the below-mentioned Examples).

Herein, the “homologous gene” denotes a homologous gene of human, rat, or the like, corresponding to any one of the target mouse genes 1 to 3 that are genes of a mouse. Human homologous genes corresponding to the target mouse gene 1, the target mouse gene 2 and the target mouse gene 3 are a gene having a base sequence of SEQ ID NO.: 4 (which is also referred to as “target human gene 1” in the specification), a gene having a base sequence of SEQ ID NO.: 5 (which is also referred to as “target human gene 2” in the specification), and a gene having a base sequence of SEQ ID NO.: 6 (which is also referred to as “target human gene 3” in the specification), respectively. Note here that other homologous genes can be found by homology search using public database (for example, BLAST search).

Herein, as the “cells,” mammalian cells may be used. Example of the mammalian cells include cells of rodents such as a mouse, a rat, a guinea pig, and cells of primates such as a human, a monkey, a chimpanzee. The origin of cells are not particularly limited. However, it is preferable to use cells derived from the central nervous system tissue. Among the central nervous system tissue, it is preferable to use cells derived from the prefrontal cortex of the forebrain, the nucleus accumbens, the striatum, the midbrain, or the hippocampus.

On the condition that cells of non-human animals (for example, mouse, rat, rabbit, chicken, and the like) are used, the cells may be used in a state in which it is not separated from the living body (that is to say, a state in which the cells constitute the living body).

In screening, it is possible to use a group of cells (for example, cells forming a specific tissue) in which a network is formed between cells instead of cells which are dispersing. Furthermore, by using two kinds or more of cells together, the screening method of the present invention may be carried out.

In addition to cells capable of inherently expressing a target gene, cells that can express a target gene after the cells are subjected to artificial manipulation can be used. For example, transformants obtained by introducing a target gene in a state in which it can express may be used. An example of the cell that can be used for transformation may include a HeLa cell, a COS cell, and a CHO cell. These cells are readily available from a cell bank such as ATCC.

The number of cells to be used in not particularly limited, and it can be determined while considering the detection sensitivity, experiment facility, and the like. For example, 1 to $10^5$ cells, preferably, 10 to $10^4$ cells, and further preferably, $10^2$ to $10^3$ cells can be used.

2. Step 2

In the step 2, the prepared cells are exposed to a test compound. The exposure to the test compound can be carried out by, for example, culturing cells in the condition in which the test compound is contained in a culture medium. Alternatively, the test compound, a solution containing the test compound, or the like, may be brought into direct contact with the cells.

The amount to be exposed can be set arbitrarily. For example, the maximum exposure amount can be employed as long as the exposure does not bring a lethal effect on the cells.

The exposure time is not particularly limited. For example, the exposure time can be set in the range from one minute to ten days. The exposure may be carried out continuously with any intervals.

The test compound used for the screening method of the present invention can include organic compounds with various molecular sizes (nucleic acid, peptide, protein, lipid (simple lipid, complex lipid (phosphoglyceride, sphingolipid, glycosyl glyceride, cerebroside, and the like), prostaglandin, isoprenoid, terpene, steroid, and the like)), or an inorganic compound. The test compound may be a naturally occurring compound or may be a synthesized compound. In the latter case, for example, it is possible to construct an effective screening system by using a means of the combinatorial synthesis. Note here that a cell extract, culture supernatant, and the like, may be used as the test compound.

3. Step 3

In the step 3, the cells exposed to the test compound are used so as to determine the expression level of target genes. In one embodiment of the present invention, as the expression level of the target gene, the amount of mRNA that is a transcriptional product of the target gene is measured. For the detection of mRNA, routine procedures such as an RT-PCR method, various hybridization methods using specific probes (for example, Southern hybridization, in situ hybridization), and the like can be used.

In another embodiment of the present invention, the amount of protein that is an expression product of the target gene is measured. For example, the detection (measurement) can be carried out by using a compound that specifically binds to a target protein. The detection method (or measurement) is not particularly limited to this alone. However, the detection (measurement) is preferably carried out by an immunological technique. In the immunological technique, an antibody against the specific protein is used, and the protein is detected by using a binding property (binding amount) of the antibody as an indicator. The term used herein “antibody” includes a polyclonal antibody, a monoclonal antibody, a chimeric antibody, a single strand antibody, a CDR graft antibody, a humanized antibody, or the fragment thereof, and the like. The antibody of the present invention can be prepared by using an immunological technique, a phage display method, a ribosome display method, and the like.

According to the immunological detection method, rapid and highly sensitive detection can be carried out and the operation is easy and simple. An example of the detection method includes an ELISA method, radioimmunoassay, FACS, an immunoprecipitation method, immunoblotting, and the like.

By using a labeled antibody, the above-mentioned detection can be carried out easily. For labeling of the antibody, for example, fluorescent dye such as fluorescein, rhodamine, Texas Red, Oregon Green, and the like, an enzyme such as horseradish peroxidase, micro peroxidase, alkaline phosphatase, β-D-galactosidase, and the like, chemiluminescence or bioluminescence compound such as luminal, acridine dye, and the like, radioisotope such as, $^{32}P$, $^{131}I$, $^{125}I$, and the like, and biotin, can be used.

4. Step 4

In the step 4, by using the measurement results of the above-mentioned steps, the change of the expression level of the target gene is determined. For example, cells that are exposed to the test compound (an exposure group) and cells that are not exposed to the test compound (a not exposure group, i.e., a control group) are prepared. The expression levels of the exposure group and the not exposure group are measured respectively, and compared with each other. Note here that the expression level of the target gene when exposure to the test compound is not carried out is known in advance, this expression amount can be used as the expression level of the not exposure group. From the comparison results, as a result of the exposure to the test compound, the degree of changing of the expression of the target gene (the change of the expression level) can be determined. Thus, the effect of the test compound on the expression level of the target gene is evaluated.

When the expression amount of the exposure group is larger as compared with the not exposure group, that is to say, when it is observed that the test compound has an increasing effect of the expression level, it can be determined that the test compound is a compound that is effective for a mental disorder. When the significant increase in the expression level is observed in the exposure group, it can be determined that the test compound is a compound that is particularly effective for a mental disorder.

As mentioned above, by using the results of this step, the effectiveness of the test compound to the mental disorder can be evaluated.

In a cell (or a group of cells), also by comparing the expression level of the gene before and after the exposure, the effect of the test compound can be evaluated. For example, (1) cells into which a target gene together with a reporter gene (for example, a luciferase gene) have been introduced are prepared; (2) the expression level of the introduced target gene is measured before and after the exposure to the test compound by using the expression level of the reporter gene as an indicator (reporter assay), and then, the measurement results are compared.

(Animal Individual Based Screening Method)

The screening of the compound effective for a mental disorder can be carried out by using an animal individual. That is to say, the present invention also provides an animal individual based screening method including the following steps.

Step i: preparing a non-human animal.

Step ii: administering a test compound to the non-human animal.

Step iii: determining the expression level of the gene (target gene) selected from the group consisting of a gene having a base sequence of SEQ ID NO.: 1, a gene having a base sequence of SEQ ID NO.: 2, a gene having a base sequence of SEQ ID NO.: 3 and homologous genes thereof in the central nervous system tissue of the non-human animal after administering the test compound.

Step iv: determining the change in expression level of the target cell due to the administration of the test compound.

Hereinafter, each step is described in detail. As the matters that are not specifically mentioned, the corresponding description of those for the cell-based screening method is applied to.

1. Step i

In the step i, a non-human animal is prepared. An example of the non-human animal includes non-human primates (a monkey, a chimpanzee, and the like), a mouse, a rat, a rabbit, a cow, a horse, a sheep, a dog, a cat, and the like. Among them, a mouse or a rat can be used preferably.

The non-human animal generally expresses homologous genes peculiar to the species with respect to the target mouse genes 1 to 3. Except for using genetically modified animals as mentioned below, in general, the expression level of this homologous gene is to be detected in this screening method.

It is preferable to use a non-human animal with pathological condition of a mental disorder. If such a disease model animal is used, in the mental disorder state, the effect of the test compound on the expression of the target gene can be examined. In other words, this screening system corresponds to an actual treatment. According to such a screening system, it is possible to select a compound that actually acts on the mental disorder and has an excellent effectiveness. On the other hand, when observation of the change in the pathological condition of the non-human animal is carried out in parallel with the measurement of the expression amount of the target gene, it is possible to examine the correlation between the change of the expression level of the target gene and the change of the pathological condition. Thus, it is possible to obtain useful information in evaluating the effect of the test compound.

As the non-human animal with pathological condition of a mental disorder, animals provided with a specific pathological condition by genetic modification and/or breeding under certain conditions can be used. For example, it has been proposed that a genetically modified mouse lacking NMDA receptors ϵ1 and ϵ4 is effective as a model animal of schizophrenic disorders (Miyamoto, Y., Yamada, K., Noda, Y., Mori, H., Mishina, M. and Nabeshima, T.: Hyperfunction of dopaminergic and serotonergic neuronal systems in mice lacking the NMDA receptor ϵ1 subunit.: FASEB J., 15, 1407-1409 (2001), Miyamoto, Y., Yamada, K., Noda, Y., Mori., H., Mishina, M. and Nabeshima, T., Lower sensitivity to stress and altered monoaminergic neuronal function in mice lacking the NDMA receptor ϵ4 subunit.: J. Neurosci., 21, 750-757 (2001)). These non-human animals can be used in the present invention. Furthermore, a mouse representing a symptom of schizophrenic disorder by administration of phencyclidine (PCP) (Noda Y. et al., Repeated phencyclidine treatment induces negative symptom-like behavior in forced swimming test in mice: imbalance of prefrontal serotonergic and dopaminergic functions. Neuropsychopharmacology. 2000 Oct. 23(4):375-87), and the like, can be used as a model animal of schizophrenic disorders of the present invention. On the other hand, as shown in the below-mentioned Examples, a mouse continuously administered with methamphetamine and the like presents pathological conditions of drug dependence. Therefore, a mouse that has been treated under such conditions can be preferably used as a model animal of drug dependence in the present invention.

2. Step ii

In the step ii, a test compound is administered to a non-human animal. The route of administration is not particularly limited and can be appropriately selected from oral administration, intravenous administration (injection), intradermal administration (injection), subcutaneous administration (injection), transdermal administration, intraoral administration, direct administration to the target tissue (injection), and the like. Herein, the target tissue is a tissue involved in mental disorder. A typical example thereof includes the central nervous system tissue (forebrain, in particular, prefrontal cortex, nucleus accumbens, striatum, midbrain, hippocampus, and the like).

The administration amount can be set arbitrarily. For example, a maximum amount can be employed as long as the test compound does not bring a lethal effect on the non-human animals.

The number of administration times may be arbitrarily set. For example, the number of administration may be in the range from once to 20 times.

3. Step iii

In the step iii, by using the non-human animal to which a test compound has been administered, the expression level of the target gene in the central nervous system tissue (forebrain, in particular, prefrontal cortex, nucleus accumbens, striatum, midbrain, hippocampus, and the like) is measured. In other words, the amount of mRNA and/or expression product (protein) of the target gene in the certain central nervous tissue is measured. Note here that any one of the measurement using a tissue extract and measurement using a tissue section (for example, immune structure dyeing) may be carried out.

If the non-human animal used herein is a mouse, the target to be detected is any of the target mouse genes 1 to 3 (or any combination thereof). If the non-human animal used herein is a species other than a mouse, the target to be detected is homologous genes of the species corresponding to the target mouse genes 1 to 3. For example, if a rat is used, the target to be detected is a rat homologous gene. When non-human animals (genetically modified animals) expressing homologous genes of other species are used, these gene are detected. Thus, by using a technique of genetic engineering, it may be possible to construct a screening method in which a subject to be detected may be a gene which the animal species does not inherently express.

4. Step iv

In the step iv, from the measurement results of the above-mentioned steps, the change of the expression level of the target gene is determined. For example, firstly, animal individuals to which the test compound is administered (an administered group) and animal individuals to which the test compound is not administered (a not-administered group) are prepared. The expression levels of the administered group and the not-administered group are measured, respectively. Then, the expression amount of the administered group and the expression amount of the not-administered group are compared with each other. From the comparison results, the degree of changing of the expression of the target gene (the change of the expression amount) as a result of the administration of the test compound can be determined. Thus, the effect of the test compound on the expression amount of the target gene is evaluated.

When the expression level of the administered group is larger than that of the not-administered group, that is to say, when it is observed that the test compound has an increasing effect of the expression level, it can be determined that the test compound is an effective compound for a mental disorder. When the significant increase in the expression level is observed in the administered group, it can be determined that the test compound is a particularly effective compound for a mental disorder.

As mentioned above, by using the results of the step, the effectiveness of the test compound for the mental disorder can be evaluated.

Similar to the cell-based screening method, in a certain animal individual (animal group), by comparing the gene expression level before and after administration of the test compound, the effect of the test compound may be evaluated.

(Diagnostic Application)

Another aspect of the present invention relates to a diagnostic application of genes which the present inventors have succeeded in identification. One embodiment of this aspect relates to a method for obtaining information for diagnosing a mental disorder and includes the following steps.

Step a: step of preparing a biological sample collected from a subject.

Step b: step of determining the expression level in the biological sample of a gene selected from the group consisting of a gene having a base sequence of SEQ ID NO.: 4, a gene having a base sequence of SEQ ID NO.: 5, a gene having a base sequence of SEQ ID NO.: 6, and natural mutants of these genes.

The information obtained by this method is used for diagnosis of mental disorders. For example, the information obtained by carrying out the above-mentioned method to patient with a mental disorder can be used for evaluation and understanding of the pathological conditions of the patient and evaluation of the treatment effect. For example, if the treatment for a mental disorder is carried out in parallel with the method of the present invention, the treatment effect can be evaluated based on the resultant information. Specifically, by carrying out the method of the present invention after administering drugs, it is possible to examine the change of the expression level of a certain gene and to determine the treatment effect from the increase and decrease of the expression level. Thus, the method of the present invention may be used for monitoring the treatment effect.

On the other hand, when the subject of the present invention is persons other than patient, that is to say, persons who have not recognized to have a mental disorder, the obtained information can be used for determination of the presence of the morbidity of mental disorders and the evaluation of the morbidity risk, and the like.

The method of the present invention can carry out a diagnosis of mental disorders based on the expression level of genes that is an objective indicator, it is extremely valuable in the filed of diagnosis of a mental disorder whose objective diagnosis has been difficult conventionally.

1. Step a

In the step a, a biological sample collected from a subject (tested subject) is prepared. The subject herein may include not only patients with mental disorders but also healthy persons (including persons who may have a mental disorder). For example, a tissue piece collected from the subject, a cell extract, cerebrospinal fluid, and the like, may be used as a biological sample. As the biological sample, a nucleic acid sample is preferably used. The nucleic acid sample can be prepared from blood, skin cells, mucosal cells, hair of a subject (a tested subject) by the conventional extract methods and purification methods.

2. Step b

In the step b, the expression level of a certain gene is determined by using a biological sample. The gene to be determined is a gene having a base sequence of SEQ ID NO.: 4 (target human gene 1), a gene having a base sequence of SEQ ID NO.: 5 (target human gene 2), or a gene having a base sequence of SEQ ID NO.: 6 (target human gene 3). The natural mutants of these genes may be a subject to be determined. When a plurality of the natural mutants are present, one or an arbitrary combination may be a subject to be determined.

Both the standard gene and the mutated gene may be a subject to be determined. For example, both the standard gene and the mutated gene are determined at the same time and the total expression level can be used as information for diagnosis. Alternatively, the expression level of the standard gene and the expression level of the mutated gene are determined respectively. Then, comparison data of the both levels may be used as information for diagnosis.

By measuring the corresponding the amount of mRNA or the amount of protein, the expression level of a certain gene can be obtained (as to the specific determination method, see the column of the above-mentioned screening method).

The present invention further relates to the application of the target human genes 1 to 3 to the risk diagnosis of mental disorders. In other words, this aspect relates to a method for obtaining information on the risk diagnosis of mental disorders and includes the following steps.

Step A: step of preparing a nucleic acid sample collected from a subject.

Step B: step of analyzing the genotype of a gene selected from the group consisting of a gene having a base sequence of SEQ ID NO.: 4, a gene having a base sequence of SEQ ID NO.: 5, and a gene having a base sequence of SEQ ID NO.: 6 in the nucleic acid sample.

The step A can be carried out by the same way as in the above-mentioned step a. The nucleic acid sample in the step A can be prepared from blood, skin cells, mucosal cells, hair, and the like, of a subject (a tested subject) by the conventional extract methods and purification methods. Genome DNA having any length can be used as a nucleic acid sample as long as it includes a gene to be analyzed. Furthermore, when a plurality of genes are to be analyzed, it is not always necessary that all genes to be analyzed should be present on the same nucleic acid. In other words, as the nucleic acid sample of the present invention, all genes to be analyzed may be present on one nucleic acid, or all the genes to be analyzed may be present on a plurality of nucleic acid. As the nucleic sample, a gene to be analyzed may not be present in a complete state (that is to say, the full length gene) but it may be a fragment gene or a partial gene as long as it includes a site necessary for analysis of the genotype (that is to say, polymorphic site).

In the step B, the genotype is analyzed. In other words, a specific genetic polymorphism is analyzed. In general, in a gene, there is an individual difference of the DNA sequence constituting the gene. This individual difference is referred to as genetic polymorphism. As the genetic polymorphism, a polymorphism in which one base is substituted by another base (SNP (single nucleotide polymorphism)), a polymorphism in which one to several tens of bases are deleted or inserted (insertion/deletion type polymorphism), a polymorphism in which the number of repetition of the repetitive sequence including two to several bases is different (VNTR (variable number of tandem repeat), microsatellite polymorphism, and the like, are well known. These genetic polymorphisms may specify the expression state of the gene or may change the amino acid in a protein encoded by the gene and affect the function thereof. Therefore, by analyzing a certain genetic polymorphism, it is possible to evaluate the potential function of the protein encoded by the gene.

The information on the resultant genotype in the step B can be used for risk diagnosis of mental disorders. For example, based on the genotype (combination of specific alleles), the degree of genetic risk of a mental disorder can be determined.

The analyzing method of polymorphism is not particularly limited and may employ well-known methods. Example of the method include a method for analyzing the polymorphism of the amplification by a PCR method by using allele specific primer (and probe), a method for analyzing the polymorphism of the amplified product by fluorescence or emission, a PCR-RFLP (restriction fragment length polymorphism) method using a PCR (polymerase chain reaction) method, a PCR-SSCP (single strand conformation polymorphism) method (Orita, M. et al., Proc. Natl. Acad. Sci., U.S.A., 86, 2766-2770 (1989), etc.), a PCR-SSO (specific sequence oligonucleotide) method, an ASO (allele specific oligonucleotide) hybridization method combining the PCR-SSO method and a dot hybridization method (Saiki, Nature, 324, 163-166 (1986), etc.), or a TaqMan-PCR method (Livak, K J, Genet Anal, 14, 143 (1999), Morris, T. et al., J. Clin. Microbiol., 34, 2933 (1996)), an Invader method (Lyamichev V et al., Nat Biotechnol, 17, 292 (1999)), MALDI-TOF/MS (matrix) method using a primer elongation process (Haff L A, Smimov I P, Genome Res 7, 378 (1997)), a RCA (rolling cycle amplification) method (Lizardi P M et al., Nat Genet 19, 225 (1998)), a method a using DNA chip or a microarray (Wang D G et al., Science 280, 1077 (1998), etc.), a primer elongation process, a Southern blotting hybridization method, a dot hybridization method (Southern, E., J. Mol. Biol. 98, 503-517 (1975)), and the like. Furthermore, the analysis may be carried out by directly sequencing a portion of the polymorphism to be analyzed. Note here that combination of these methods may be used for analyzing the polymorphism. Furthermore, after the nucleic acid sample is amplified in advance (including amplification of a partial region of the nucleic acid sample) by a nucleic acid amplification method such as a PCR method or a method applying the PCR method, and the like, any of the above-mentioned analyzed methods may be employed.

When a large number of nucleic acid samples are analyzed, it is preferable to use an analyzing method capable of analyzing a large number of specimens for a relatively short time. Such analyzing method includes an allele specific PCR method, an allele specific hybridization method, a TaqMan-PCR method, an Invader method, a MALDI-TOF/MS (matrix) method using primer elongation process, an RCA (rolling cycle amplification) method, a method a using DNA chip or a microarray, and the like.

The polymorphisms of each gene can be analyzed by using mRNA that is a transcriptional product of gene to be analyzed. After mRNA of gene to be analyzed is extracted/purified from blood, urine, etc. from a subject, a northern blotting method (Molecular Cloning, Third Edition, 7.42, Cold Spring Harbor Laboratory Press, New York), a dot blot method, (Molecular Cloning, Third Edition, 7. 46, Cold Spring Harbor Laboratory Press, New York), an RT-PCR method (Molecular Cloning, Third Edition, 8.46, Cold Spring Harbor Laboratory Press, New York), a method using a DNA chip (DNA array), and the like, are executed. Thereby, polymorphism analysis using mRNA as a starting material can be analyzed.

The polymorphism can be analyzed by using the expression product of gene to be analyzed. In this case, a partial protein or a partial peptide can be used as a sample for analysis as long as it contains amino acid corresponding to a polymorphism site.

As the analysis method using the expression product of a gene, a method for directly analyzing amino acid at the polymorphism site, or a method of immunological analysis by using the change of the three-dimensional structure and the like, can be carried out. For the former example, a well-known amino acid sequence analyzing method (a method using an Edman's method) can be used. As the latter method, by using a monoclonal antibody or a polyclonal antibody having a binding property specific to an expression product of gene having any genotype constituting a polymorphism, an ELISA method (enzyme-linked immunosorbent assay), radioimmunoassay, an immunoprecipitation method, an immunodiffusion technique, and the like, can be used.

(Treatment Application)

The further aspect of the present invention relates to treatment application of genes which the present inventors have successfully identified. In one embodiment of this aspect, an antipsychotic drug is provided. The antipsychotic drug of the present invention includes a compound for increasing the expression level in the target tissue of a gene selected from the group consisting of a gene having a base sequence of SEQ ID NO.: 4 (target human gene 1), a gene having a base sequence of SEQ ID NO.: 5 (target human gene 2), a gene having a base sequence of SEQ ID NO.: 6 (target human gene 3), and the natural mutant thereof. Thus, the antipsychotic drug of the present invention has an effect of increasing the expression level in the target tissue of gene.

In general, herein, a central nervous system tissue is "target tissue." When the expression level of any of the above genes is increased in the central nervous system tissue, the direct effect on mental disorders can be expected.

A specific example of compounds (active ingredients) contained in the drug of the present invention may include an isolated protein having an amino acid sequence of SEQ ID NO.: 10, an isolated protein having an amino acid sequence of SEQ ID NO.: 11, or an isolated protein having an amino acid sequence of SEQ ID NO.: 12. The proteins are expression products of the target human genes 1 to 3, respectively. Therefore, according to the drugs containing the proteins, when the drugs are delivered to a target tissue, the amount of the expression product of the target human gene in the target tissue is increased. Note here that the natural mutant (corresponding to the natural mutant of the target human gene) of the any of the above-mentioned proteins can be used as an active ingredient.

The term "isolated" used herein about protein refers to a state in which the protein is extracted from the original environment (for example, natural environment in the case of the natural material), that is, a state in which the protein existing in a state that is different from the state by the artificial manipulation.

When the protein of the present invention is derived from the natural material, the "isolated" state is generally a state in which the natural material does not substantially contain a component other than the protein (in particular, contaminated protein is not substantially contained). Specifically, in the isolated protein of the present invention, the content of the contaminated protein on a weight basis is, for example, less than about 20%, preferably less than about 10%, further preferably, less than about 5%, and still further preferably, less than about 1% with respect to total weight.

On the other hand, when a protein is produced by recombinant DNA technology, the "isolated" state generally refers to a state that is free from other components derived from the used host cell, a culture medium, or the like. Specifically, in the isolated protein, the content of the contaminated protein on a weight basis is, for example, less than about 20%, preferably less than about 10%, further preferably, less than about 5%, and still further preferably, less than about 1%, with respect to total weight.

Furthermore, when a protein is produced by chemical synthesis, the "isolated" state generally refers to a state that is free from precursors (raw materials), chemical materials used in the synthesizing process, or the like. Specifically, in the isolated protein, the content of a precursor on a weight basis is, for example, less than about 20%, preferably less than about 10%, further preferably, less than about 5%, and still further preferably, less than about 1%, with respect to total weight.

The protein of the present invention is preferably prepared by using genetic engineering techniques. For example, a target protein can be obtained by, for example, introducing nucleic acid encoding the target protein into an appropriate host cell and recovering the protein expressed in the transformant. The recovered protein is purified if necessary. The target protein can be obtained by using a cell-free protein synthesis system. The cell-free protein synthesis system means that from nucleic acid (DNA and mRNA) as a template, mRNA or protein encoded by the nucleic acid is synthesized in vitro by using ribosome derived from living cells (or obtained by genetic engineering techniques) or a transcription—translation factor instead of using living cells. The cell-free synthesis system generally uses a cell extract obtained by purifying a cell homogenized solution if necessary. The cell extract generally includes ribosome that is necessary for protein synthesis, various factors such as an initiation factor, and various enzymes such as tRNA. When protein is synthesized, various amino acids, energy source such as ATP, GTP, and the like, creatine phosphate, and other materials necessary for synthesizing protein are added to this cell extract. Needless to say, when protein is synthesized, ribosome prepared separately, various factors, and/or various enzymes may be supplemented if necessary. The development of a transcription/translation system for reconstructing various molecules (factors) necessary for protein synthesis has been reported (Shimizu, Y. et al.: Nature Biotech., 19, 751-755, 2001). In this synthesis system, genes of three kinds of initiation factors constituting the protein synthesis system of bacteria, three kinds of elongation factors, four kinds of factors involved in termination, 20 kinds of aminoacyl tRNA synthesis synthase for binding various amino acid to tRNA, and 31 kinds of factors including methionyl tRNA formyl transferase are amplified from *Escherichia coli* genome. By using them, a protein synthesis system is reconstructed in vitro. In the present invention, such a reconstructed synthesis system may be used.

The term "cell-free transcription/translation system" can be used compatibly with a cell-free protein synthesis system, an in vitro translation system or an in vitro transcription/translation system. In the in vitro translation system, protein is synthesized by using RNA as a template. An example of the template RNA includes total RNA, mRNA, in vitro transcriptional product, and the like. On the other hand, in the in vitro transcription/translation system, DNA is used as a template. The template DNA should include a ribosome binding region and preferably include an appropriate terminator sequence. The in vitro transcription/translation system sets conditions in which factors necessary to each reaction are added so that the transcription reaction and the translation reaction proceed continuously.

The cell-free synthesis systems widely used at present include the following systems: an *Escherichia coli* S30 fraction extract system (prokaryotic cell system), a wheat germ extract system (eukaryotic cell system), and a rabbit reticulocyte solubilizer system (eukaryotic cell system). These systems are commercially available as a kit and can be used easily.

The target protein can be prepared by separation and purification of a natural source (obtaining source). An example of the source of protein in the present invention includes animal cells (including human cells), plant cells, body fluid (blood, urine, etc.), and the like.

Other specific examples of the compound (active ingredient) contained in the antipsychotic drug of the present invention can include an isolated nucleic acid encoding any of the above-mentioned proteins. That is to say, an example of the active ingredient can include an isolated nucleic acid encoding an amino acid sequence of SEQ ID NO.: 10, an isolated nucleic acid encoding an amino acid sequence of SEQ ID NO.: 11, and an isolated nucleic acid encoding an amino acid sequence of SEQ ID NO.: 12. These nucleic acids are contained in a state in which they can be expressed in the target tissue when the antipsychotic drug of the present invention is administered. For example, a nucleic acid in a state in which it is inserted in an appropriate expression vector is used. That is to say, the present invention provides an expression vector comprising a nucleic acid (specifically, for example, DNA having a base sequence of any of SEQ ID NOs.: 1 to 6) encoding an amino acid sequence of any of SEQ ID NOs.: 7 to 12. The nucleic acid is inserted into the expression vector in a state in which it is linked operatively to an appropriate regulatory sequence working in the target tissue.

The term "nucleic acid" used herein includes DNA (including cDNA and genome DNA), RNA (including mRNA), a DNA analogue and an RNA analogue. The form of nucleic acid of the present invention is not particularly limited. That is to say, it may be any of a single stranded DNA and a double stranded DNA. Preferably, it is a double stranded DNA. Furthermore, codon degeneracy is contemplated. That is to say, in the case of nucleic acid encoding protein, the nucleic acid may include any base sequences as long as the protein can be obtained as an expression product.

In this specification, "nucleic acid encoding protein" denotes nucleic acid from which the protein is obtained when it is expressed. The nucleic acid includes not only nucleic acid having a base sequence corresponding to the amino acid sequence of the protein but also nucleic acid obtained by adding a sequence that does not encode the amino acid sequence to the above-mentioned nucleic acid (for example, DNA including one or a plurality of introns).

Furthermore, in this specification, the term "isolated nucleic acid" is typically one which is separated from other nucleic acids co-existing in the natural state when the nucleic acid is a naturally occurring nucleic acid (for example, nucleic acid in a living human body). However, the isolated nucleic acid may include a part of other nucleic acid components, for example, nucleic acid sequences flanking in the natural state. Preferably, the "isolated nucleic acid" is substantially free of other DNA components (including DNA sequences which naturally flank the nucleic acid) co-existing in a natural state in, for example, the genomic DNA.

Preferably, the "isolated nucleic acid" such as a cDNA molecule can be substantially free of other cellular components or culture medium when produced by recombination techniques. Similarly, preferably, the "isolated nucleic acid" such as a ddNTP can be substantially free of precursors (raw materials), other chemicals used in chemical synthesis, or the like, when chemically synthesized.

When nucleic acid is present as a part of a vector or a composition, or a nucleic acid is present in a cell as an exogenous molecule, the nucleic acid may be an "isolated nucleic acid" as long as it is present as a result of an artificial manipulation.

The nucleic acid used in the present invention can be prepared into an "isolated state" by referring to the sequence information disclosed in the present specification or attached sequence list and by using standard genetic engineering technique, molecular biological technique, biochemical technique, and the like. For example, the nucleic acid can be isolated by a hybridization method using the base sequence of the target nucleic acid or the entire or part of the complementary sequence as a probe. Furthermore, the nucleic acid can be isolated by using a nucleic acid amplification reaction (for example, PCR) using a synthesized oligonucleotide primer that has been designed to specifically hybridize to a part of the base sequence. Note here that the oligonucleotide primer can be easily synthesized by using a commercially available automated DNA synthesizer.

The preferable embodiment of the nucleic acid to be used in the present invention has a base sequence of any of SEQ ID NOs.: 4 to 6. In the other embodiment of the present invention, a DNA molecule (for example, nucleic acid including only a coding region) in which any one or more of the 5' non-translation region or a part thereof and the 3' non-translation region or a part thereof is deleted from the base sequence of any of SEQ ID NOs.: 4 to 6. Note here that a nucleic acid combining a non-translation region that is different from the original non-translation region may be used as long as it does not adversely affect the translation in the coding region.

Drugs of the present invention can be formulated according to the conventional method. In formulation, other ingredients acceptable for formulation (for example, carrier, vehicle, disintegrating agents, buffer agent, emulsifying agent, suspending agent, soothing agent, stabilizer, preservative, antiseptic agent, physiological saline, and the like) can be contained. An example of the vehicle may include lactose, starch, sorbitol, D-mannitol, and sucrose. An example of the disintegrating agents may include starch, carboxymethyl cellulose, calcium carbonate, and the like. An example of the buffer agent may include phosphate, citrate, acetate, and the like. An example of the emulsifying agent may include gum Arabic, alginate sodium, tragacanth, and the like. An example of the suspending agent may include glyceryl monostearate, aluminum monostearate, methylcellulose, carboxymethyl cellulose, hydroxymethyl cellulose, sodium lauryl sulfate, and the like. An example of the soothing agent may include benzyl alcohol, chlorobutanol, sorbitol, and the like. An example of the stabilizer may include propylene glycol, diethylene sulfite, ascorbic acid, and the like. An example of the preservative may include phenol, benzalkonium chloride, benzyl alcohol, chlorobutanol, methylparaben, and the like. An example of the antiseptic agent may include benzalkonium chloride, parahydroxybenzoate, chlorobutanol, and the like.

The dosage form in the formulation is not particularly limited. An example of the dosage form may include tablet, powdered drug, fine subtilae, granule, capsules, syrup, injectable drug, external preparation, and suppository.

The thus formulated drug of the present invention can be administered to a patient by oral administration or parenteral administration (intravenous, intra-arterial, subcutaneous, intramuscular, intraperitoneal injection, and the like) depending upon the dosage form.

The content of the active ingredient (compound) in the drug of the present invention is, for example, in the range from about 0.001 wt. % to about 90 wt. % generally depending upon the dosage form. Thus, a predetermined dosage amount can be achieved.

Another aspect of the present invention provides a prevention method or a treatment method (hereinafter, these two methods are together referred to as "treatment method and the like") of mental disorders by using the above-mentioned drug. The treatment method and the like of the present invention includes a step of administering the antipsychotic drug of the present invention to a living body. The route of administration is not particularly limited and can includes, for example, oral, intravenous, subcutaneous, intramuscular, intraperitoneal, transdermal, transmucosal administrations, and the like. The dosage amount of the drug will vary depending on the symptoms, age, sex, body weight, and the like, of the patient, but the person skilled in the art can set an appropriate dosage amount. For example, the dosage amount can be set so that the dosage amount of active ingredient for adult (body weight: about 60 kg) per day is about 0.001 mg to about 100 mg. The administration regimen can include, for example, once to several times a day, once per two days, or once per three days. For setting administration schedule, conditions of a patient, efficacy duration time of the drug, and the like, can be considered.

(Application for Study)

The present invention further relates to an application for study of genes that have been successfully identified. One embodiment of this aspect provides a reagent for application for study of mental disorders, which includes the isolated nucleic acid having any of the base sequences of SEQ ID NOs.: 1 to 6 or the homologous nucleic acid thereof. Another embodiment of this aspect provides a reagent for application for study of mental disorders, which includes isolated protein having an amino acid sequence of SEQ ID NOs.: 7 to 12 or the homologous protein thereof.

The reagent of the present invention can be used as a research tool for studying the onset mechanism or developing mechanism of symptom of mental disorders. Furthermore, it can be used as a reagent for carrying out the method of the present invention (a screening method, a method of obtaining information for diagnosis, and the like), or can be used as a component constituting the drug of the present invention. The reagent of the present invention can be used for producing a chimera mouse or a transgenic mouse as a model animal of mental disorders.

The reagent of the present invention contains nucleic acid in a state in which, for example, it is inserted into an appropriate vector (for example, an expression vector). In other words, the present invention provides an expression vector comprising a nucleic acid encoding an amino acid sequence of any of SEQ ID NOs.: 7 to 12. Specific embodiment of the expression vector of the present invention comprises a DNA having a base sequence of any of SEQ ID NOs.: 1 to 6.

The "homologous nucleic acid" herein is referred to as nucleic acid in which, as compared with the reference nucleic acid (nucleic acid having a base sequence of any of SEQ ID NOs.: 1 to 6), the function of protein encoded thereby is equal to that of the reference nucleic acid but a part of the base sequence is different from that of the reference base sequence. An example of the homologous nucleic acid includes DNA encoding a protein having a feature that it has a base sequence including substitution, deletion, insertion, addition or inversion in one or a plurality of base when the base sequence of any of SEQ ID NOs.: 1 to 6 is made to be a reference base sequence, and that the expression amount is increased relating to mental disorder. The substitution, deletion, or the like, of the base may occur in a plurality of sites. Herein, "plurality" denotes, for example, 2 to 40 bases, preferably 2 to 20 bases, and more preferably 2 to 10 bases, although it depends upon the positions or kinds of the amino acid residue in the three-dimensional structure of the protein encoded by the nucleic acid. The above-mentioned homologous nucleic acid can be obtained by genetically modifying nucleic acid having a sequence of SEQ ID NOs.: 1 to 6 so that a certain site may include substitution, deletion, insertion, addition or inversion of base by using a site specific mutation method. Furthermore, homologous nucleic acid can be obtained by other method such as irradiation with ultraviolet ray.

Another example of the homologous nucleic acid can include nucleic acid that hybridizes to the complementary strand of the nucleic acid of any of base sequences of SEQ ID NOs.: 1 to 6 under stringent conditions. Herein, "stringent conditions" are referred to as conditions in which a so-called specific hybrid can be formed and a nonspecific hybrid cannot be formed. Such stringent conditions are known to person skilled in the art and can be set with reference to, for example, Molecular Cloning (Third Edition, Cold Spring Harbor Laboratory Press, New York) and Current protocols in molecular biology (edited by Frederick M. Ausubel et al., 1987). An example of the stringent conditions can include a condition in which a hybridization solution (50% formamide, 10×SSC (0.15M NaCl, 15 mM sodium citrate, pH 7.0), 5×Denhardt solution, 1% SDS, 10% dextran sulfate, and 10 μg/ml modified salmon sperm DNA, 50 mM phosphate buffer (pH 7.5)) is used and incubated at about 42° C. to about 50° C., thereafter, 0.1×SSC and 0.1% SDS are used and washed at about 65° C. to about 70° C. Further preferable stringent conditions can include conditions of using, for example, a hybridization solution (50% formamide, 5×SSC (0.15M NaCl, 15 mM sodium citrate, pH 7.0), 1×Denhardt solution, 1% SDS, 10% dextran sulfate, 10 μg/ml modified salmon sperm DNA and 50 mM phosphate buffer (pH 7.5)).

Further example of the homologous nucleic acid can include nucleic acid in which the above-mentioned difference in the base is recognized due to the polymorphism represented by SNP.

(Kit Used in the Present Invention)

Each method of the present invention (screening method, a method for obtaining information for diagnosis, and the like) may be carried out by using a kit of reagent and the like. Another aspect of the present invention provides a kit used for such a purpose. For example, nucleic acid (probe and primer), reaction reagent, dilution, a reactor vessel, and the like, that are used for the method of the present invention can be contained in the kit. Note here that the kit of the present invention is generally includes instruction.

(Antibody to the Protein of the Present Invention)

The present invention further provides an isolated antibody having a specific binding property to the protein (target protein) having amino acid sequences of any of SEQ ID NOs.: 7 to 12. The antibody of the present invention is useful as a tool for studying mental disorders. For example, the antibody of the present invention is used for, for example, detecting, measuring and determining the target protein and expected to be contributed to elucidation of the action mechanism of mental disorders. The antibody of the present invention is expected to be applied to treatment or diagnosis of mental disorders.

The antibody of the present invention may be any one of a polyclonal antibody, an oligoclonal antibody (mixture of several kinds to several tens kinds of antibodies), and a monoclonal antibody. As the polyclonal antibody or the oligoclonal antibody, in addition to an IgG fraction derived from antiserum obtained by immunizing an animal, it is possible to use an antibody obtained by affinity-purifying with antigen. The antibody may be any antibody fragments such as Fab, Fab', $F(ab')_2$, scFv, and dsFv antibodies, and the like.

The antibody of the present invention may be prepared by using an immunological technique, a phage display method, a ribosome display method, and the like. A polyclonal antibody by an immunological technique can be prepared by the following procedures. Antigen (target protein or a part thereof) is prepared and an animal such as a rabbit, mouse, rat, or the like, is immunized with this prepared antigen. The antigen can be obtained by purifying a biological sample. Furthermore, recombinant protein (or peptide) can be used as an antigen. As mentioned below, the present inventors have obtained an antibody having a specific binding property to the protein having a amino acid sequence of SEQ ID NO.: 7 by using two kinds of partial peptides (CNTAFRGLRQHPRTQLL: SEQ ID NO.: 19, and CMSVDSRFRGKGIAKALG: SEQ ID NO.: 20) as an antigen.

Recombinant protein (or peptide) as an antigen can be prepared by, for example, introducing a gene (a part of a gene may be included) encoding an amino acid sequence of any of SEQ ID NOs.: 7 to 12 into an appropriate host by using a vector and expressing the gene in the obtained recombinant cell.

In order to enhance an immune provocation effect, an antigen to which a carrier protein is bonded may be used. As the carrier protein, KLH (Keyhole Limpet Hemocyanin), BSA (Bovine Serum Albumin), OVA (Ovalbumin), and the like, can be used. For the binding of the carrier protein, a carbodiimide method, a glutaraldehyde method, a diazo condensation method, an MBS (maleimide benzoyloxysuccinimide) method, and the like, can be used. On the other hand, it is also possible to use an antigen in which the target protein (or a part thereof) is expressed as a fused protein with GST, β galactosidase, maltose binding protein, histidine (His) tag, or the like, can be used. Such a fused protein can be purified by a general method in a simple way.

Immunization is repeated if necessary. At the time when the antibody titer is sufficiently increased, blood is collected and centrifuged so as to obtain serum. The obtained antiserum is affinity-purified so as to obtain a polyclonal antibody.

On the other hand, the monoclonal antibody can be prepared by the following procedures. Firstly, by the same procedure as mentioned above, immunization operation is carried out. If necessary, immunization is repeated. At the time when the antibody titer is sufficiently increased, antibody production cells are extracted from the immunized animal. Next, the obtained antibody production cells and myeloma cells are fused, so that hybridoma is obtained. Subsequently, this hybridoma is made into monoclones, followed by selecting a clone capable of producing antibody having a high specificity against an objective protein. By purifying the culture medium of the selected clone, the objective antibody can be obtained. On the other hand, after the hybridoma is proliferated into a predetermined number or more, this is transplanted into the peritoneal cavity of an animal (for example, a mouse) and proliferated in the ascites, followed by purifying the ascites. Thereby, the objective antibody can be obtained. For the purification of the above-mentioned culture medium or the purification of the ascites, affinity chromatography using the protein G, protein A, and the like, is preferably used. Furthermore, an affinity chromatography in which antigen is made into a solid phase can be used. Furthermore, an ion exchange chromatography, a gel filtration chromatography, ammonium sulfate fractionation, and centrifugation, and the like, can be used. These methods can be used singly or in a combination of any of them.

EXAMPLES

1. Experimental Materials and Methods

1-1. Search of Genes Related to Drug Dependence 1-1-1 Extract of mRNA

By using RNeasy mini kit (QIAGEN), mRNA was prepared by the following procedure. Mouse brain was taken out and the tissue was divided so as to be 30 mg or less. The brain tissue was dissolved in a solution containing a protein denaturizing agent and centrifuged with a spin column. Ethanol precipitation was repeated. Finally, mRNA was purified with silica gel.

1-1-2 cDNA Subtraction

The cDNA subtraction was carried out by using CLONTECH PCR-Select™ cDNA Subtraction Kit (CLONTECH) according to the attached instruction manual.

1-2. Place Preference Test 1-2-1. Animals

In the test, c57/black6 male mice (Japan SLC, Hamamatsu) that were 8-week old when the test was started. The mice were bred under conditions of light and dark cycle of 12 hours (light up at A.M 8:00), room temperature of 23±1° C., and humidity of 50±5%. The mice were freely fed with food (CE2: CLEA Japan, Tokyo) and water. This research program was approved by Animal Research Committee, Nagoya University School of Medicine and carried out in accordance with Guideline of Animal Research of Nagoya University School of Medicine and Principles of Laboratory Animal Care (National Institutes of Health Publication 85-23, 1985).

1-2-2. Drug

In the test, methamphetamine hydrochloride (philopon, Dainihon Seiyaku, Osaka) dissolved in saline was used.

1-2-3 Device for Test

In the test, a device having two chambers (light and dark chambers) and being provided with a partition between two chambers so that a mouse cannot come and go between two chambers (15 cm in length, 15 cm in width, and 15 cm in height). Staying time in each box was measured by using SCANET (Neuroscience, Tokyo).

1-2-4 Conditioned Place Preference Test

Conditioned place preference test was carried out in accordance with the method by Noda et al. (Noda Y, Miyamoto Y, Mamiya T, Kamei H, Furukawa H, Nabeshima T: Involvement of dopaminergic system in phencyclidine-induced place preference in mice pretreated with phencyclidine repeatedly. J Pharmacol Exp Ther 286: 44-51 (1998)). In the 2-day preconditioning test, mice were allowed to go and come between both chambers for 15 minutes a day for three days so that the mice became accustomed to the device. On day 3, the time staying in each chamber was measured (pre-value). After the pre-conditioning test, the 6-day conditioning test was carried out. In the conditioning test, a partition was put between chambers and mice were made to stay in only one of the chambers. On day 4, 6 and 8, right after methamphetamine or morphine was administered to the mice by subcutaneous administration, the mice were placed in the chamber with lower preference (the chamber with shorter staying time was shown in the pre-conditioning test). On day 5, 7 and 9, right after a physiological saline solution was administered to the mice by subcutaneous administration, the mice were placed in the opposite chambers. In the post conditioning test, the mice were allowed to go and come between the chambers and the staying time of each chamber, that is, the post-value was measured. The place preference was calculated from "(post-value)−(pre-value)." Note here that during all days of test, Leu-Ile was administered by intraperitoneal injection to the mice one hour before they were placed in the chamber.

1-2-5. Statistical Analysis

All the results are shown in a mean value and standard error. For the statistical analysis, one-way layout analysis of variance was carried out. When the significant difference was observed, multiple comparison test by Bonferroni was further carried out. Note here that, the difference with significance level of 5% or less was defined as the significant difference.

1-3. Measurement of Locomotor Activity 1-3-1. Animal

In the test, ICR male mice (Japan SLC, Hamamatsu) that were 8-week old when the test was started. The mice were bred under conditions of light and dark cycle of 12 hours (light up: A.M 8:00), room temperature 23±1° C., and humidity 50±5%. The mice were freely fed with food (CE2: CLEA Japan, Tokyo) and water. Note here that this research program was approved by Animal Research Committee, Nagoya University School of Medicine and carried out in accordance with Guideline of Animal Research of Nagoya University School of Medicine and Principles of Laboratory Animal Care (National Institutes of Health Publication 85-23, 1985).

1-3-2. Drug

In the test, methamphetamine hydrochloride (philopon, Dainihon Seiyaku, Osaka) dissolved in physiological saline solution (saline) was used.

1-3-3 Device for Test

In the test, an acrylic cage (28 cm in length, 17 cm in width and 13 cm in height) that is the same kind as the home case was used. On the floor, a small amount of breeding chip was placed. From the starting day to the completion date, cage and breeding chip at the measurement time were same for each mouse. For measuring the locomotor activity, an infrared detector (Neuroscience, Tokyo) was used. Analysis was carried out by using AB305 Measure and ABTEXT (Neuroscience, Tokyo).

1-3-4. Locomotor Activity Test

On days 1 to 3, mice were placed in a measurement cage for two hours so that the mice became accustomed to the measurement environment. Later than the fourth day, methamphetamine was administered to the mice by subcutaneous administration once a day. Right after the administration, the total locomotor activity for two hours was measured.

1-3-5. Statistical Analysis

All the results are shown in a mean value and standard error. For the statistical analysis, two-way layout analysis of variance was carried out. When the significant difference was observed, multiple comparison test by Bonferroni was further carried out. Note here that, the difference with significance level of 5% or less was defined as the significant difference.

Figure 1:
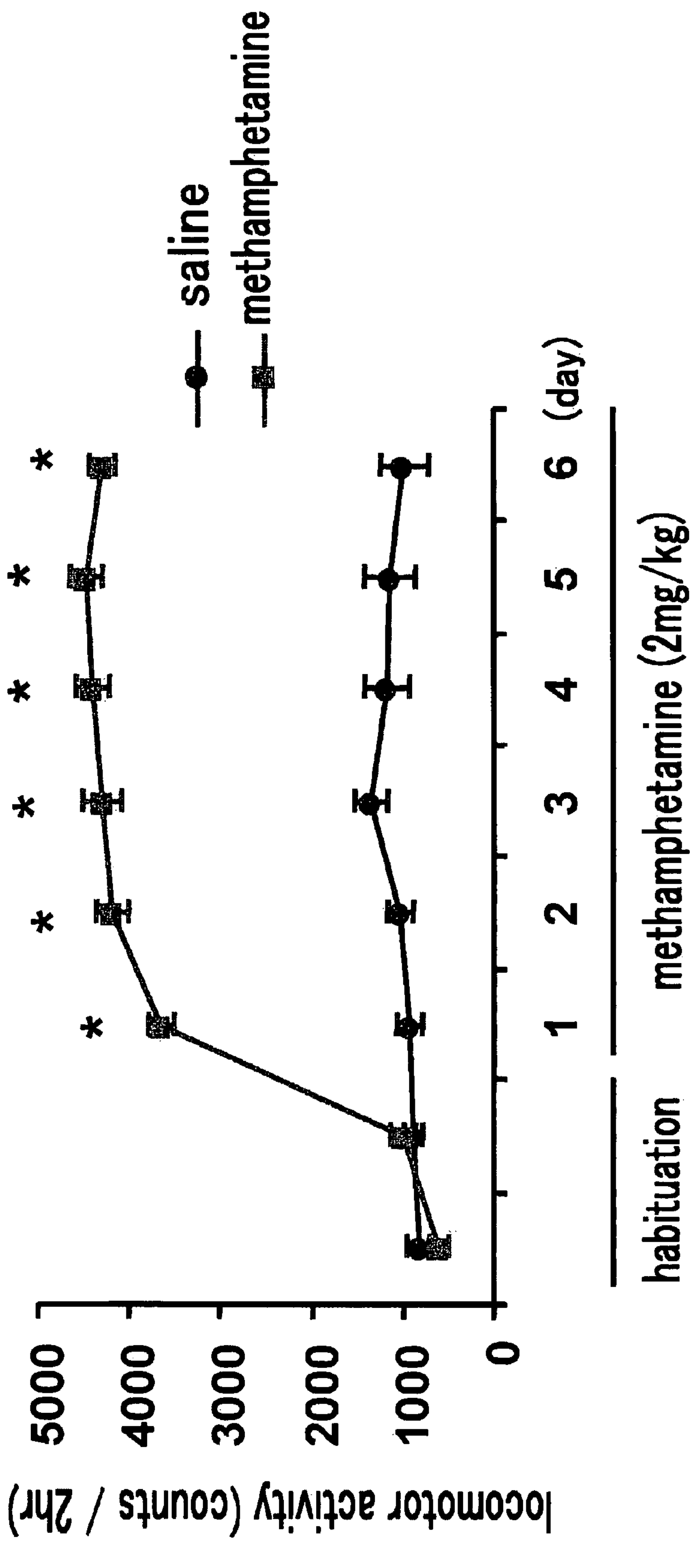
FIG. 1 is a graph showing that the locomotor activity is enhanced when methamphetamine is administered to mice continuously. Methamphetamine (2 mg/kg, s.c.) was administered to mice for six days. The results are shown in a mean value±standard error (n=20-30). *$P<0.05$ compared with the physiological saline solution administered group. In a repetitive two-way layout analysis of variance, a significant difference was observed.
Figure 5:
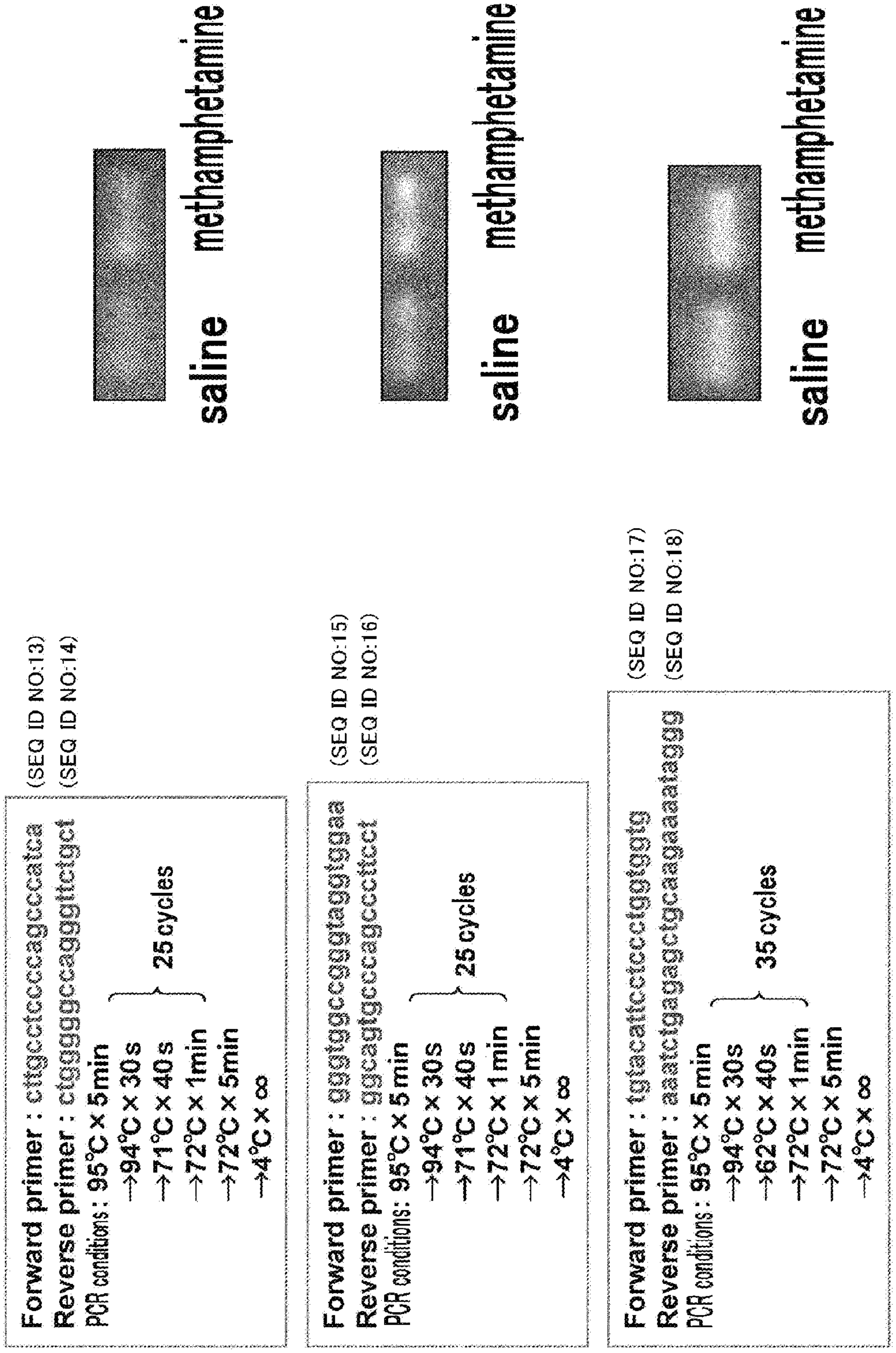
FIG. 5 is a view showing the change of the expression of Gene 1 mRNA after continuous administration of methamphetamine. Methamphetamine (2 mg/kg, s.c.) was administered to mice for six days, and two hours after the final administration, the mice were subjected to decapitation (n=4-5).
Figure 6:
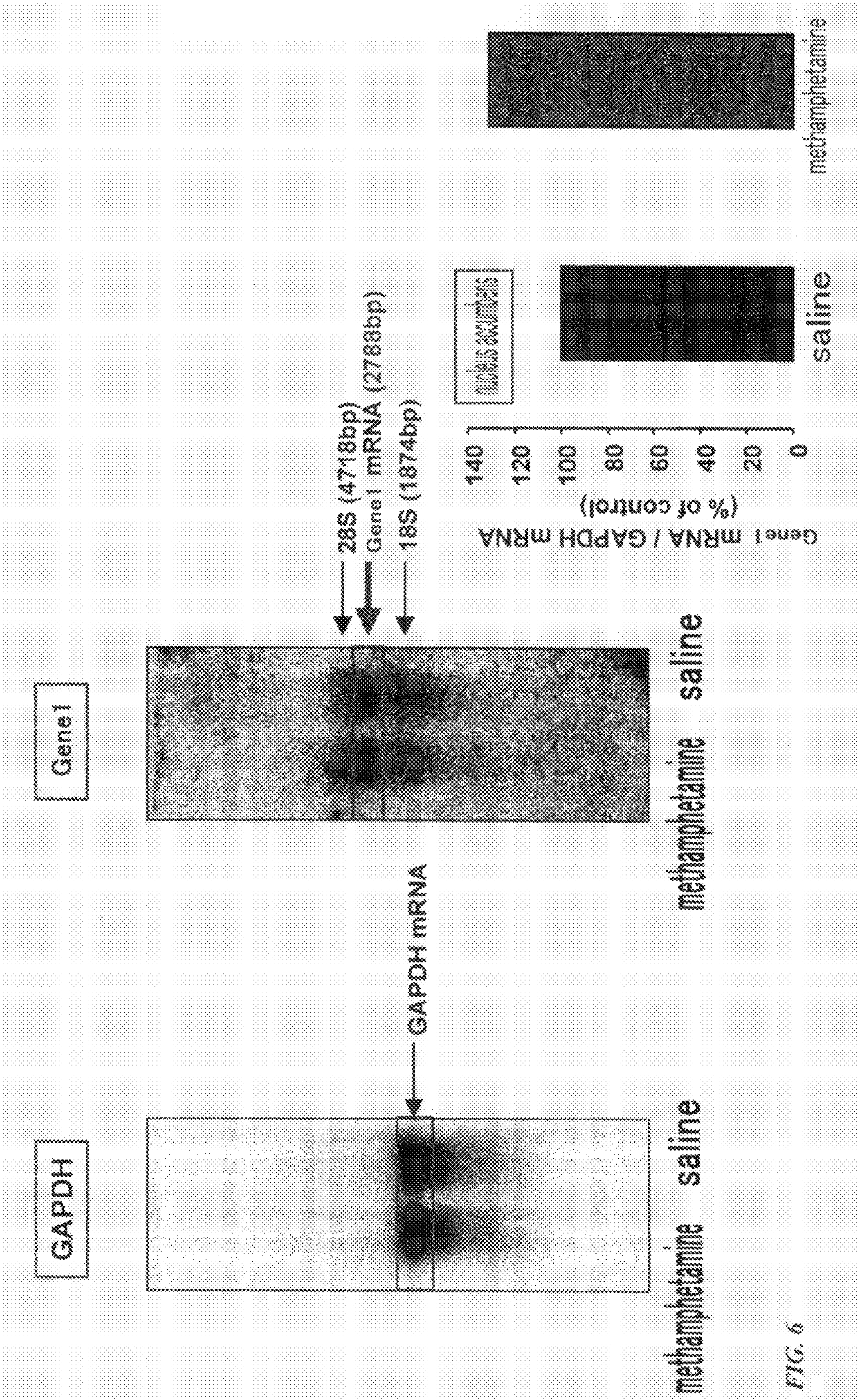
FIG. 6 shows the size of Gene 1 and the change in the expression of Gene 1 mRNA after continuous administration of methamphetamine in the nucleus accumbens. Methamphetamine (2 mg/kg, s.c.) was administered to mice for six days, and two hours after the final administration, the mice were subjected to decapitation (n=4-5). The change in the expression of Gene 1 mRNA was examined by northern hybridization. The data were corrected by using GAPDH mRNA.
Figure 8:
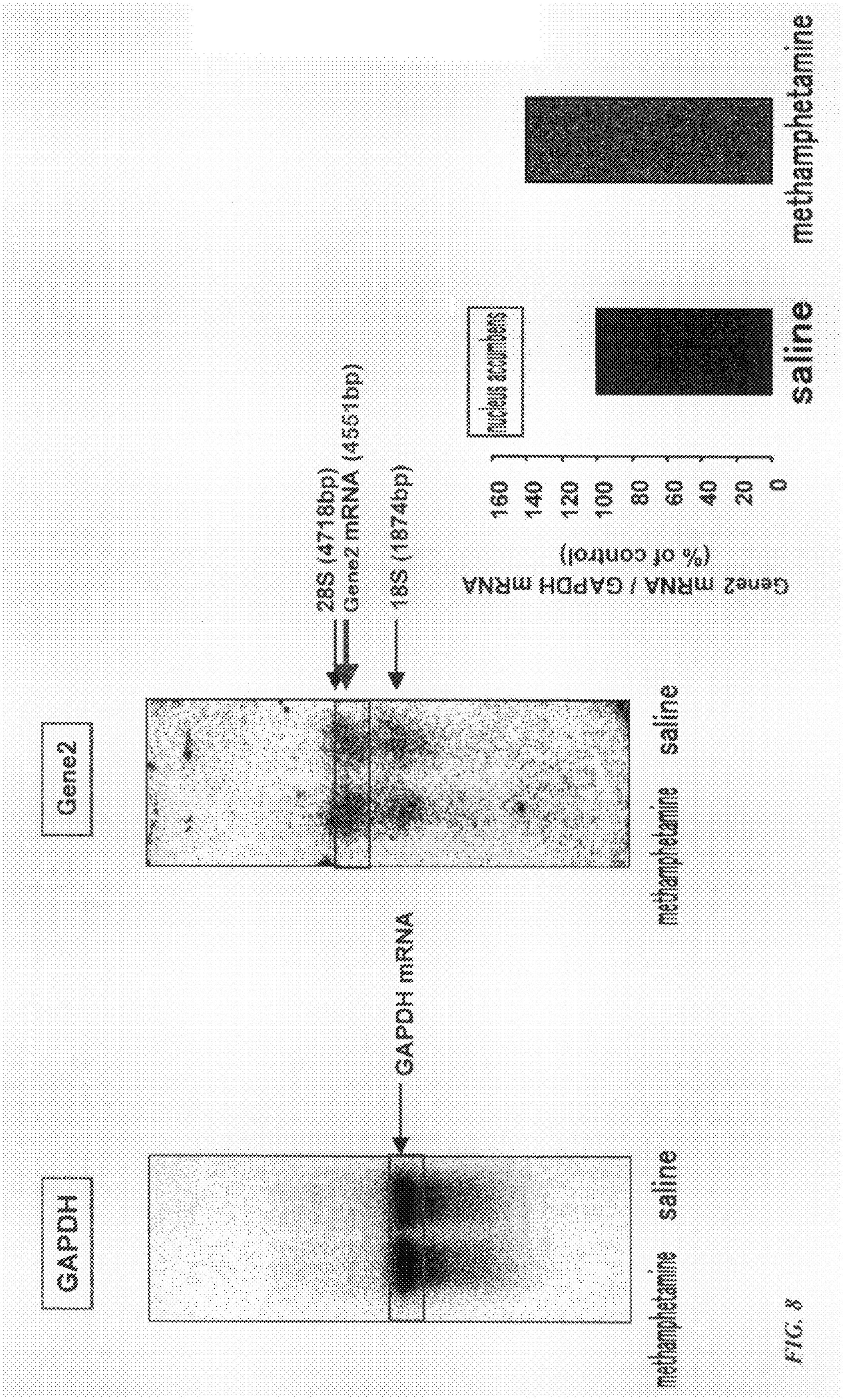
FIG. 8 shows the size of Gene 2 and the change in the expression of Gene 2 mRNA after continuous administration of methamphetamine in the nucleus accumbens. Methamphetamine (2 mg/kg, s.c.) was administered to mice for six days, and two hours after the final administration, the mice were subjected to decapitation (n=4-5). The change in the expression of Gene 2 mRNA was examined by northern hybridization. The data were corrected by using GAPDH mRNA.
Figure 9:
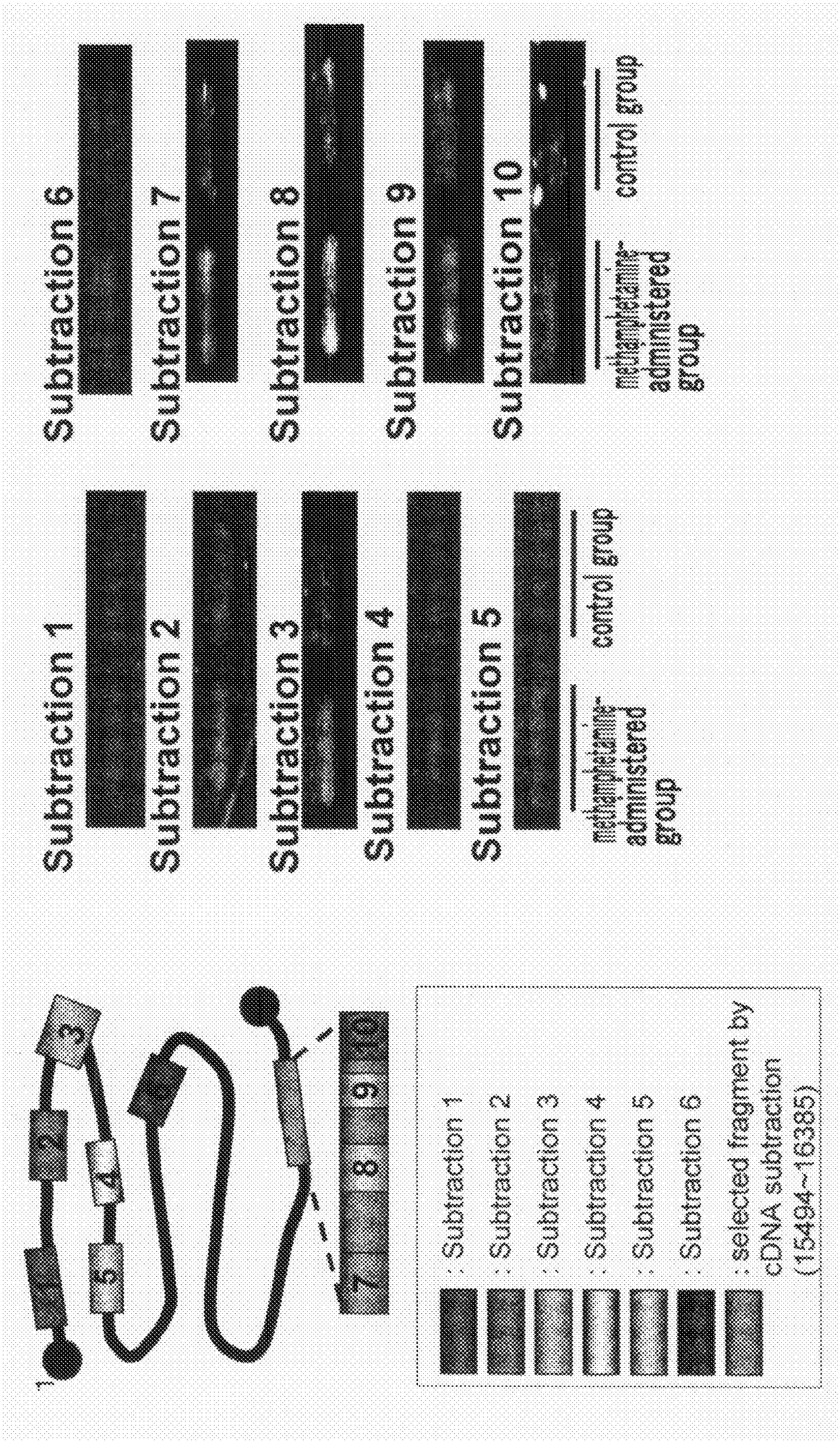
FIG. 9 shows the change in the expression of Piccolo mRNA in the nucleus accumbens after administration of methamphetamine. Methamphetamine (2 mg/kg, subcutaneous administration) was administered to a mouse for six days, and the nucleus accumbens extracted from the brain 24 hours after the final administration was used as a sample.

2. Search of Novel Gene Related to Drug Dependence 2-1. Search of Novel Gene by Using Model Animal Methamphetamine-administered mice show hyperactivity, and when methamphetamine is administered to mice every day, the degree of hyperactivity is increased. This can be thought to be a mental disorder accompanying drug dependence (FIG. 1). Then, mRNA was taken out from the mouse (C57black6) nucleus accumbens to which methamphetamine had been administered for 10 consecutive days. Based on this, cDNA subtraction (CLONTECH) was carried out. In mice to which methamphetamine had been administered, a gene in which mRNA expression amount increased by 20 times or more than that of a control group was searched. As a result, five genes satisfy the requirement (FIG. 2). In the genes, three genes except for CREB3 and Odz4 were used for the later research. For convenience of description, each gene is referred to as Gene 1, Gene 2 and Gene 3 (Piccolo).

When Gene 1, 2 and Gene 3 were retrieved by BLAST search, they were completely matched to partial sequences of the genes registered as BC034068 (GenBank Accession No. NM_001001985 XM_194205, *Mus musculus* cDNA sequence BC034068 (BC034068), mRNA: SEQ ID NO.: 1), 8430437G11Rik (GenBank Accession No. NM_028990, *Mus musculus* RIKEN cDNA 8430437G11 gene (8430437G11Rik), mRNA.: SEQ ID NO.: 2), and Piccolo or Aczonin (GenBank Accession No. NM_011995, *Mus musculus* piccolo (presynaptic cytomatrix protein) (Pclo), mRNA.: SEQ ID NO.: 3), respectively (FIGS. 3 and 4). The amino acid sequences encoded by Gene 1 (BC034068), 2 (8430437G11Rik) and 3 (Piccolo or Aczonin) are shown in SEQ ID NO.: 7, SEQ ID NO.: 8, and SEQ ID NO.: 9, respectively. Note here that Gene 1 was registered under the designation of mouse Shati in GeneBank (Accession No. DQ174094).

2-2. Search of Human Homologous Gene

Human homologous genes of Genes 1, 2 and 3 were retrieved by BLAST search. As a result, human homologous genes of Genes 1, 2 and 3 (which were referred to as Gene 1 human homologous gene, Gene 2 human homologous gene and Gene 3 human homologous gene, respectively) were found as follows. Two of the human homologous genes were genes whose function was not known, and remaining one gene was a gene identified as Piccolo or Aczonin.

Gene 1 human homologous gene: *Homo sapiens* cDNA FLJ3478 fis, clone BRAWH2013219, weakly similar to *Homo sapiens* N-acetyltransferase Camello 2 (CML2) mRNA (Genbank Accession No. AK094797: SEQ ID NO.: 4)

Gene 2 human homologous gene: *Homo sapiens* cDNA FLJ13576 fis, clone PLACE1008715 (Genbank Accession No. AK023638: SEQ ID NO.: 5)

Gene 3 human homologous gene: *Homo sapiens* piccolo (presynaptic cytomatrix protein) (PCLO), mRNA (Genbank Accession No. NM_033026, XM_168530: SEQ ID NO.: 6)

Note here that amino acid sequences encoded by Gene 1 human homologous gene, Gene 2 human homologous gene and Gene 3 human homologous gene are shown in SEQ ID NO.: 10, SEQ ID NO.: 11 and SEQ ID NO.: 12, respectively.

3. Change of Expression of Novel Gene

Figure 10:
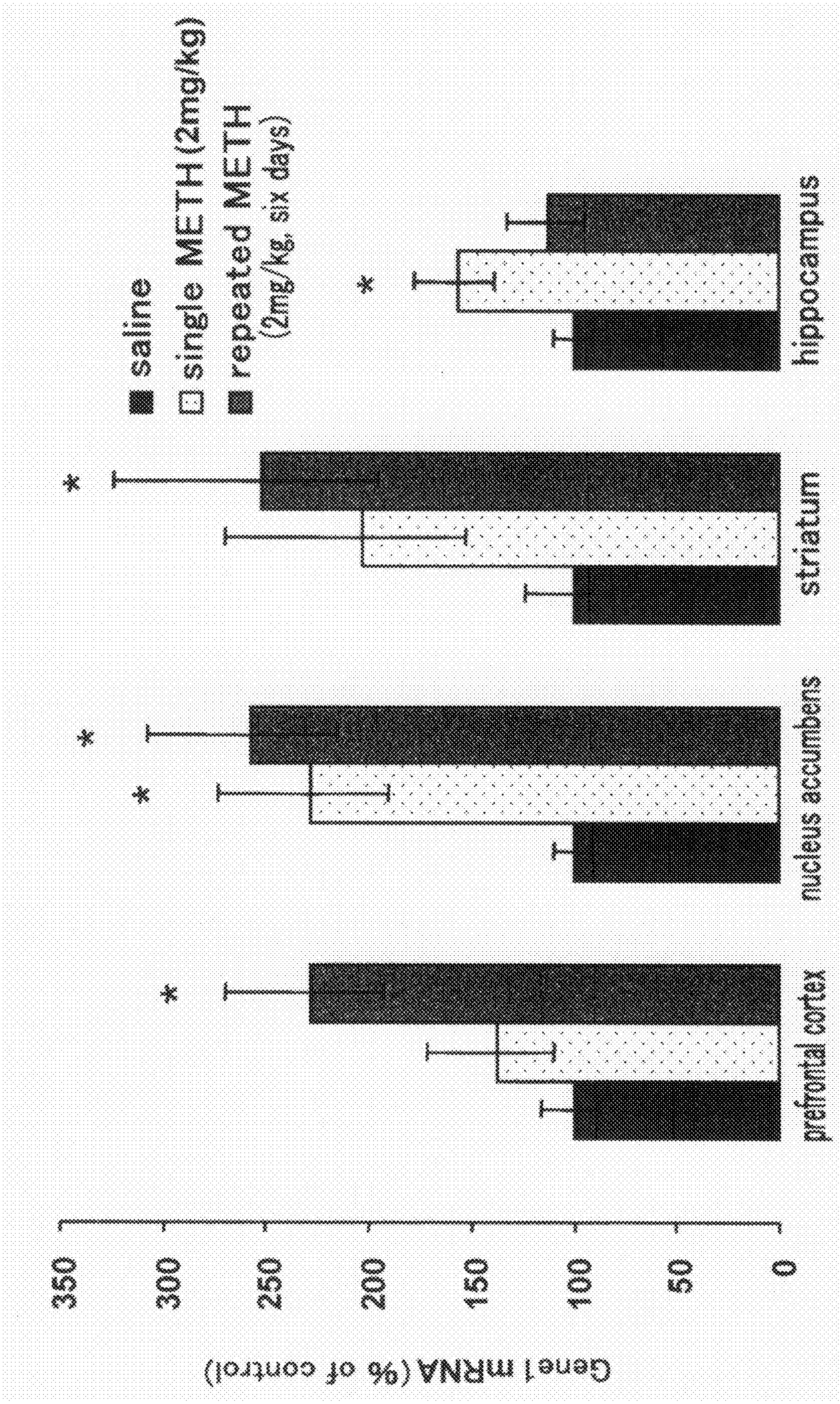
FIG. 10 shows the change in the expression of Gene 1 mRNA after single time administration and repeated administration of methamphetamines. Methamphetamine (2 mg/kg, s.c.) was administered to mice for six days, and two hours after the final administration, the mice were subjected to decapitation. The results are shown in a mean value±standard error (n=8). * $P<0.05$ compared with the physiological saline solution administered group.
Figure 11:
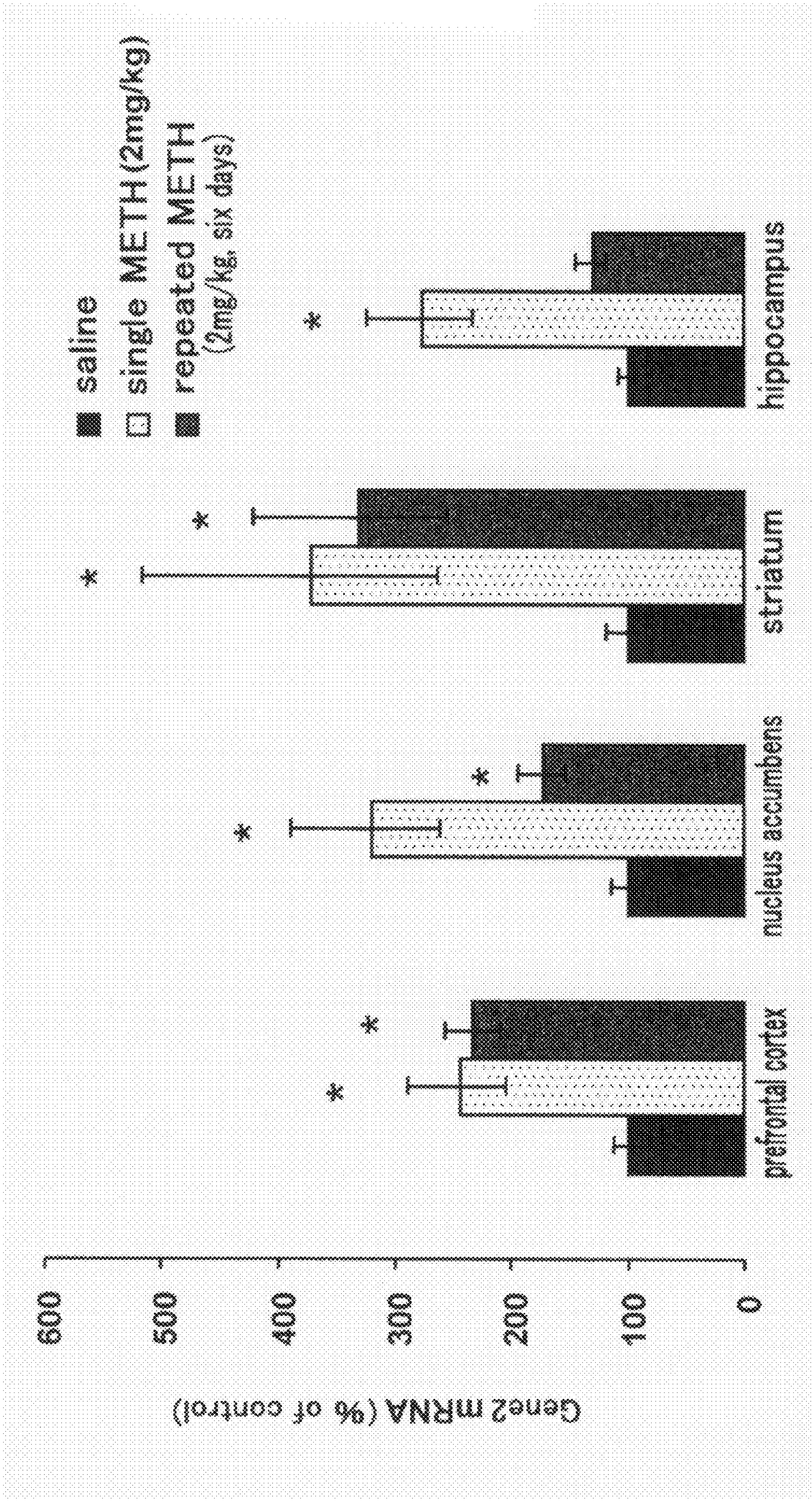
FIG. 11 shows the change in the expression of Gene 2 mRNA after single time administration and repeated administration of methamphetamines. Methamphetamine (2 mg/kg, s.c.) was administered to mice for six days, and two hours after the final administration, the mice were subjected to decapitation. The results are shown in a mean value±standard error (n=8). * $P<0.05$ compared with the physiological saline solution administered group.
Figure 12:
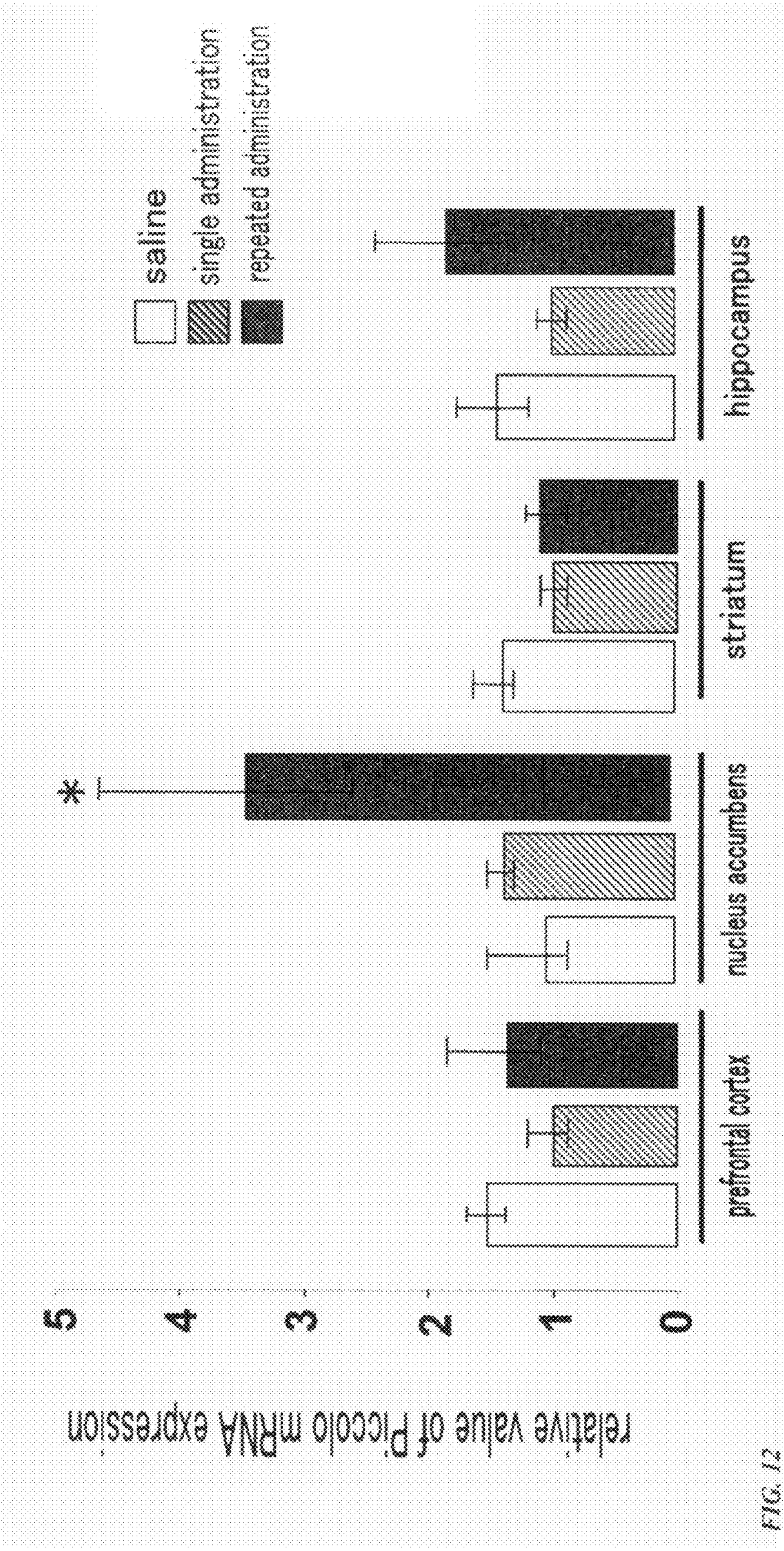
FIG. 12 shows the change in the expression of piccolo (Gene 3) in a mouse after treatment with methamphetamine. Single time administration and continuous administration of methamphetamine (1 mg/kg, subcutaneous administration) was carried out to mice for six days, and two hours after the final administration, the mice were subjected to decapitation and used as samples. The number of mice in each group was made to be 5 to 8. * $P<0.05$ compared with the physiological saline solution administered group.

As to Genes 1 to 3, a part of each gene was subjected to RT-PCR method, in all the combination of primers, the increase of mRNA was observed in the methamphetamine administered group as compared with the control group (FIGS. 5 to 9). Furthermore, when the increase of the expression amount was examined by a real time RT-PCR method, the expression amount was increased in the methamphetamine-administered cortex of frontal lobe, nucleus accumbens and striatum, respectively (FIGS. 10 to 12).

Figure 13:
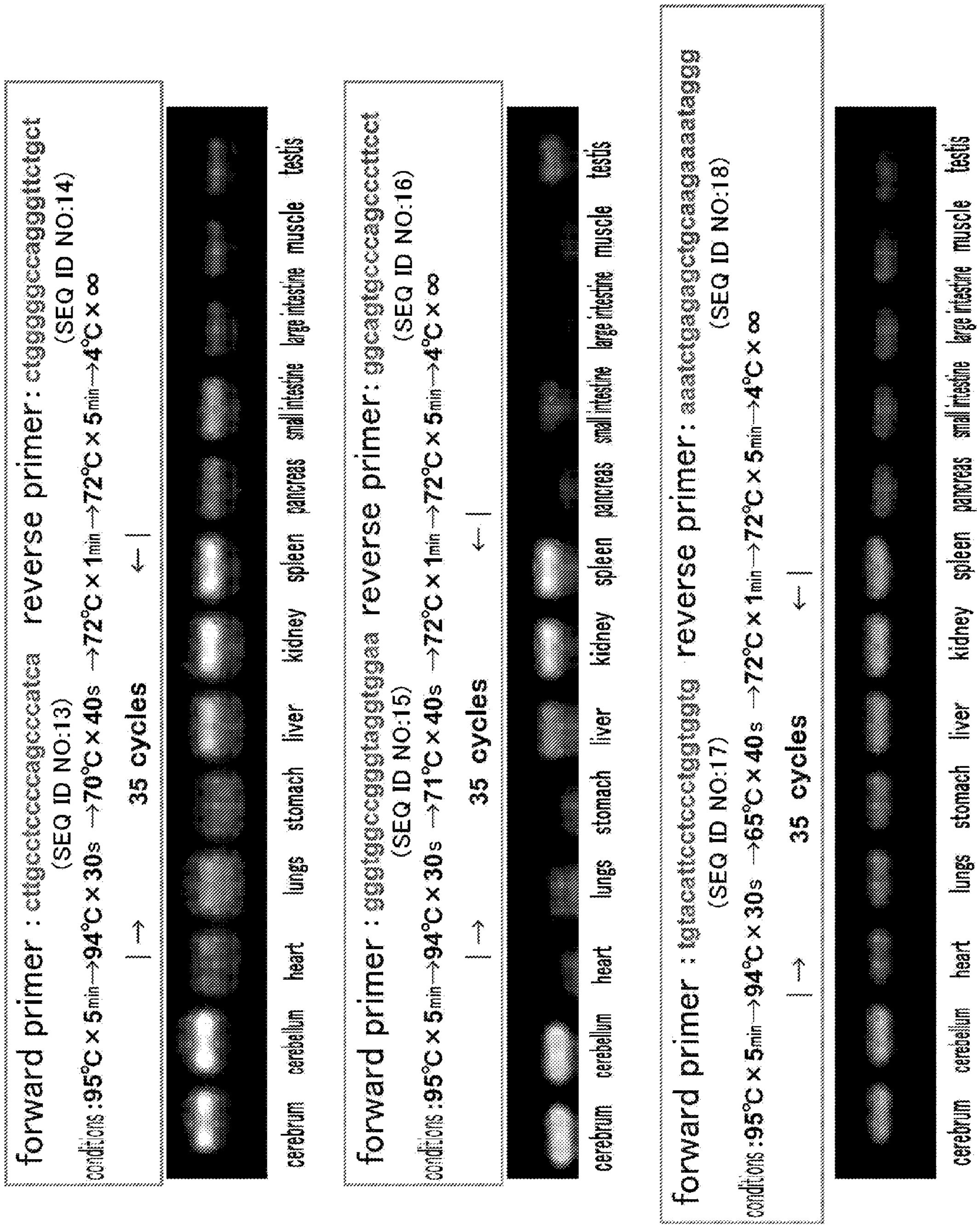
FIG. 13 shows the expression level of Gene 1 in each tissue of a living body of a mouse.

When the expression amount of Gene 1 in each tissue of mouse was examined by RT-PCR, it was confirmed that Gene 1 was highly expressed in the cerebrum and cerebellum (FIG. 13). Furthermore, also in the liver, kidney, and spleen, Gene 1 was highly expressed. Three kinds of primer sets and PCR conditions used in RT-PCR are shown below.

(1) Primer Set 1

```
Forward primer:
cttgcctccccagcccatca      (SEQ ID NO.: 13)
and

reverse primer:
ctgggggccagggttctgct      (SEQ ID NO.: 14)
```

Reaction conditions: reaction was carried out at 95° C. for 5 minutes, followed by repeating reaction cycles 35 times each cycle including reaction at 94° C. for 30 seconds, at 70° C. for 40 seconds and at 72° C. for one minute, then reaction was carried out at 72° C. for 5 minutes and left at 4° C.

(2) Primer Set 2

```
Forward primer:
gggtggccgggtaggtggaa      (SEQ ID NO.: 15)
and

reverse primer:
ggcagtgcccagcccttcct      (SEQ ID NO.: 16)
```

Reaction conditions: reaction was carried out at 95° C. for 5 minutes, followed by repeating reaction cycles 35 times each cycle including reaction at 94° C. for 30 seconds, at 71° C. for 40 seconds, and at 72° C. for one minute, then reaction was carried out at 72° C. for 5 minutes and left at 4° C.

(3) Primer Set 3

```
Forward primer:
tgtacattcctccctggtggtg        (SEQ ID NO.: 17)
and

reverse primer:
aaatctgagagctgcaagaaaataggg   (SEQ ID NO.: 18)
```

Reaction conditions: reaction was carried out at 95° C. for 5 minutes, followed by repeating reaction cycles 35 times each cycle including reaction at 94° C. for 30 seconds, at 65° C. for 40 seconds, and at 72° C. for one minute, then reaction was carried out at 72° C. for 5 minutes and left at 4° C.

4. Expression Suppression Experiment 4-1. Effect of Gene 1 Antisense Oligonucleotide and Gene 2 Antisense Oligonucleotide in Enhancement of Locomotor Activity Induced by Methamphetamine Each of the antisense nucleotide of Gene 1 and 2 was infused into the mice cerebral ventricle continuously by using a mini osmotic pump and methamphetamine was administered to the animals every day. The locomotor activity on the first, third and fifth days was measured. Note here that methamphetamine (1 mg/kg, s.c.) was administered to the mice for five days. The locomotor activity was measured for two hours. In the right cerebral ventricle (AP −0.5 mm, ML +11.0 mm from bregma, DV −2.0 mm from the skull), antisense oligonucleotide (Gene 1-AS or Gene2-AS, 1.8 nmol/6 μl/day), scramble control oligonucleotide (Gene 1-SC or Gene2-SC), and artificial cerebrospinal fluid (CSF) were infused continuously by using an osmotic pump.

Figure 14:
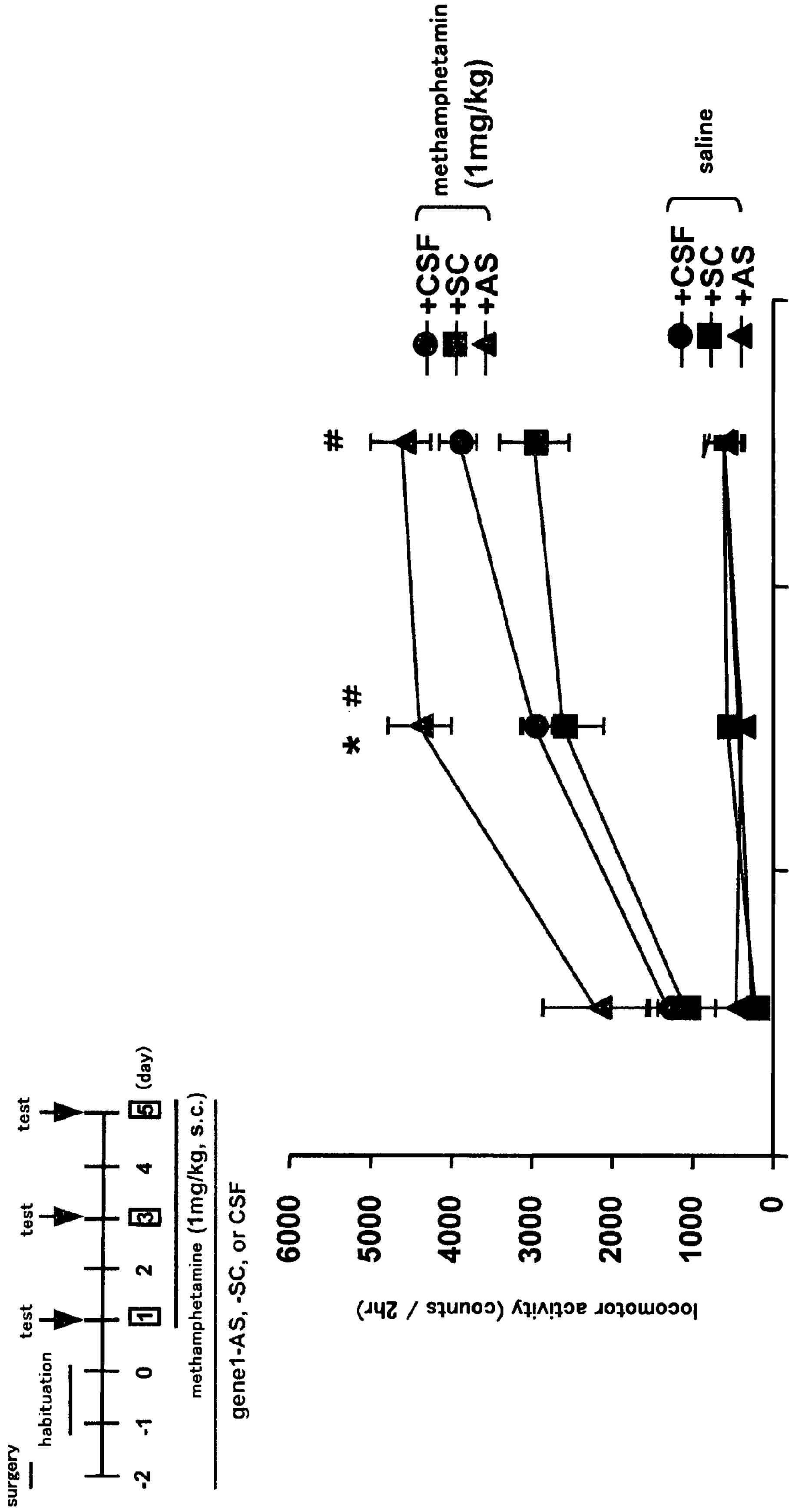
FIG. 14 is a view showing an effect of Gene 1 antisense oligonucleotide in the methamphetamine-induced enhancement of locomotor activity. Methamphetamine (1 mg/kg, s.c.)

The measurement result of Gene 1 is shown in FIG. 14; and the measurement result of Gene 2 is shown in FIG. 15. The results are shown in a mean value±standard error (Gene 1: n=5-7, Gene 2: n=3-5). As to Gene 1, in the repetitive two-way layout analysis of variance, between Gene 1 antisense oligonucleotide treated group and the control group and scramble control oligonucleotide group, the significant difference was observed (* $P<0.05$ compared with the physiological saline solution+CSF-treated group. # $P<0.05$ compared with the physiological saline solution+Gene 1-SC-treated group).

4-2. Effect of Gene 1 Antisense Oligonucleotide and Gene 2 Antisense Oligonucleotide in Place Preference Formation by Methamphetamine As to Gene 1 and Gene 2, by using antisense oligonucleotide, the place preference test was carried out. During the conditioning, methamphetamine (0.3 mg/kg, s.c.) or a physiological saline solution was administered to mice. In the right cerebral ventricle (AP-0.5 mm, ML +1.0 mm from bregma, DV −2.0 mm from the skull), antisense oligonucleotide (Gene 1-AS or Gene2-AS, 1.8 nmol/6 μl/day), scramble control oligonucleotide (Gene 1-SC or Gene2-SC) and artificial cerebrospinal fluid (CSF) were infused continuously by using an osmotic pump.

The measurement result of Gene 1 is shown in FIG. 16; and the measurement result of Gene 2 is shown in FIG. 17. The results are shown in a mean value±standard error (n=5-12). Between the oligonucleotide treated group and the control group and scramble control oligonucleotide group, the significant difference was observed (*$P<0.05$ compared with the physiological saline solution-treated group. # $P<0.05$ compared with the methamphetamine+CSF-treated group).

4-3. Effect of Gene 3 Antisense Oligonucleotide in Enhancement of Locomotor Activity Induced by Methamphetamine As to Gene 3 (piccolo), the antisense nucleotide was infused into the mouse cerebral ventricle continuously by using a mini osmotic pump and methamphetamine was administered to the animals every day. The locomotor activity on the first, third and fifth days was measured. Methamphetamine (1 mg/kg, subcutaneous administration) was administered to the mice for six consecutive days. 24 hours after the final administration, the mice were subjected to decapitation so as to obtain a sample. The number of mice in each group was five.

The measurement results are shown in FIG. 18. The results are shown in a mean value±standard error (n=5). In the repetitive two-way layout analysis of variance, between the Gene 3 antisense oligonucleotide treated group and the control group and sense oligonucleotide group, the significant difference was observed (*** $p<0.0005$ compared with physiological saline solution).

4-4. Change of Expression of Gene 1 mRNA in Gene 1 Antisense Oligonucleotide Treated Mouse by Continuous Administration of Methamphetamine Antisense nucleotide of Gene 1 was continuously infused into the mouse cerebral ventricle by using a mini osmotic pump and methamphetamine was administered to the animals every day. Three days after the start of experiment, the mice were subjected to decapitation and the Gene 1 expression amount in the nucleus accumbens was measured by a real time RT-PCR method. The measurement results are shown in FIG. 19. The results are shown in a mean value±standard error (n=8). In the repetitive two-way layout analysis of variance, between the Gene 1 antisense oligonucleotide treated group and the control group and scramble control oligonucleotide group, the significant difference was observed (* $P<0.05$ compared with the physiological saline solution+CSF-treated group. #$P<0.05$ compared with the physiological saline solution+Gene 1-SC-treated group. $ $P<0.05$ compared with the physiological saline solution+Gene 1-AC-treated group. + $P<0.05$ compared with the methamphetamine+Gene 1-SC-treated group).

5. Effect and Action Mechanism of Gene 1

5-1. Effect of Dopamine D1 Receptor Antagonist R(+)-$SCH_{23390}$ and Dopamine D2 Receptor Antagonist Raclopride in the Increase of Expression of Gene 1 mRNA in the Nucleus Accumbens Induced by Methamphetamine Methamphetamine (2 mg/kg, s.c.) was administered to mice once a day for six days, and 30 minutes before methamphetamine was administered, dopamine D1 receptor antagonist R(+)-SCH23390 (0.1 mg/kg, i.p.) or dopamine D2 receptor antagonist raclopride (2 mg/kg, i.p.) were administered. Two hours after the final administration, the mice were subjected to decapitation and the Gene 1 expression amount in the nucleus accumbens was measured by a RT-PCR method. The measurement results are shown in FIG. 20. The results are shown in a mean value±standard error (n=6-8). In the repetitive two-way layout analysis of variance, in the vehicle administered group, R(+)-SCH23390 administered group and raclopride administered group, the significant difference was observed (* $P<0.05$ compared with the vehicle/physiological saline solution-administered group. # $P<0.05$ compared with the vehicle/methamphetamine administered group). The results suggest that the increase of mRNA expression amount of Gene 1 is controlled by a signal via a dopamine receptor.

5-2. Change of Expression of TNF-α mRNA in Gene 1 Antisense Oligonucleotide Treated Mouse by Continuous Administration of Methamphetamine Methamphetamine (1 mg/kg, s.c.) was administered to mice once a day for five days. During this time, in the right cerebral ventricle (AP −0.5 mm, ML +1.0 mm from bregma, DV −2.0 mm from the skull), Gene 1 antisense oligonucleotide (Gene 1-AS, 1.8 nmol/6 μl/day), scramble control oligonucleotide (Gene 1-SC) and artificial cerebrospinal fluid (CSF) were continuously infused by using an osmotic pump. Two hours after the final administration of methamphetamine, the mice were subjected to decapitation and TNF-α mRNA expression amount in the nucleus accumbens was measured by a RT-PCR method. The measurement results are shown in FIG. 21. The results are shown in a mean value±standard error (n=8-10). In Gene 1 antisense oligonucleotide treated group, control (CSF treated) group and scramble control oligonucleotide group, the significant difference was observed (*$P<0.05$ compared with physiological saline solution-administered group. # $P<0.05$ compared with the physiological saline solution+CSF-treated group and a physiological saline solution+Gene 1-SC-treated group. $ $P<0.05$ compared with the methamphetamine+Gene 1-SC treated group). The results suggest that Gene 1 may act via TNF-α.

5-3. In Vivo Effect of Gene 1 Antisense Oligonucleotide in the Increase of the Amount of Extracellular Dopamine Induced by Methamphetamine Methamphetamine (1 mg/kg, s.c.) was administered to mice for two days. During this time, in the right cerebral ventricle (AP −0.5 mm, ML +1.0 mm from bregma, DV −2.0 mm from the skull), Gene 1 antisense oligonucleotide (Gene 1-AS, 1.8 nmol/6 μl/day), scramble control oligonucleotide (Gene 1-SC), or artificial cerebrospinal fluid (CSF) was continuously infused by using an osmotic pump. On day 3, by in vivo microdialysis method, the amount of extracellular dopamine in the nucleus accumbens (AP +1.7 mm, ML −0.8 mm from bregma, DV −4.0 mm from the skull) was measured for 220 minutes after the administration of methamphetamine. The measurement results are shown in FIG. 22. The results are shown in a mean value±standard error (n=5-6). In the repetitive two-way layout analysis of variance, between the Gene 1 antisense oligonucleotide treated group and the control (CSF) group and scramble control oligonucleotide group, the significant difference was observed (* $P<0.05$ compared with the Gene 1-SC-treated group). The results suggest that Gene 1 suppresses the increase of the amount of extracellular dopamine induced by methamphetamine.

5-4. Effect of Gene 1 in the Reduction of Uptake of Synaptosomal [$^3$H]DA Induced by Methamphetamine Methamphetamine (1 mg/kg, s.c.) was administered to mice for three days. During this time, in the right cerebral ventricle (AP −0.5 mm, ML +1.0 mm from bregma, DV −2.0 mm from the skull), Gene 1 antisense oligonucleotide (Gene 1-AS, 1.8 nmol/6 μl/day), scramble control oligonucleotide (Gene 1-SC), and artificial cerebrospinal fluid (CSF) were continuously infused by using an osmotic pump. The final concentration of [$^3$H]DA was 5 nM. Two hours after the final administration of methamphetamine, the mice were subjected to decapitation and the amount of [$^3$H]DA in the midbrain synaptosome was measured. The measurement results are shown in FIG. 23. The results are shown in a mean value±standard error (n=7-8). The amount of uptake of synaptosomal [$^3$H]DA in the physiological saline solution+CSF-treated group, physiological saline solution+Gene 1-SC-treated group, physiological saline solution+Gene 1-AS-treated group, methamphetamine+CSF-treated group, methamphetamine+Gene 1-SC-treated group, methamphetamine+Gene 1-AS-treated group were 0.32±0.04, 0.29±0.03, 0.20±0.02, 0.18±0.01, 0.20±0.01, and 0.09±0.01 μmol/4 minutes/mg of proteins. This result suggest that Gene 1 suppresses the reduction of uptake of the dopamine into synaptosome induced by methamphetamine.

5-5. Effect of Gene 1 in the Reduction of Uptake Synaptovesicular [$^3$H]DA Induced by Methamphetamine Methamphetamine (1 mg/kg, s.c.) was administered to mice for three days. During this time, in the right cerebral ventricle (AP −0.5 mm, ML +1.0 mm from bregma, DV −2.0 mm from the skull), Gene 1 antisense oligonucleotide (Gene 1-AS, 1.8 nmol/6 μl/day), scramble control oligonucleotide (Gene 1-SC), and artificial cerebrospinal fluid (CSF) were continuously infused by using an osmotic pump. The final concentration of [$^3$H]DA was 30 nM. Two hours after the final administration of methamphetamine, the mice were subjected to decapitation and the amount of [$^3$H]DA in the midbrain synaptosome was measured. The measurement results are shown in FIG. 24. The results are shown in a mean value±standard error (n=8). The amount of uptake of synaptovesicular [$^3$H]DA in the physiological saline solution+CSF-treated group, physiological saline solution+Gene 1-SC-treated group, physiological saline solution+Gene 1-AS-treated group, methamphetamine+CSF-treated group, methamphetamine+Gene 1-SC-treated group, methamphetamine+Gene 1-AS-treated group were 3.76±0.25, 4.05±0.29, 2.80±0.20, 1.74±0.21, 1.85±0.14, and 0.90±0.14 μmol/4 minutes/mg of proteins. These results suggest that Gene 1 suppresses the reduction of dopamine uptake induced by methamphetamine synaptovesicle.

5-6. Effect of Tranfection of Gene 1 in Reduction of Uptake of [$^3$H]DA Induced by Methamphetamine By using pcDNA-DEST53 (Invitrogen), an expression vector in which the full length Gene 1 or a fragment of Gene 1 had been incorporated was constructed (FIG. 25). Into the PC22 cell, an expression vector for expressing the full length Gene 1, an expression vector for expressing the fragment of Gene 1, or a pcDNA-DEST vector (empty vector) was transfected with Lipofectamine. After cells were cultured in a 24-well plate for 2 to 3 days, the cells were pre-treated with methamphetamine (1.0 μM) for 30 minutes. Then, by using Krebs-Ringer HEPES buffer containing 10 μM pagyline and 10 μM ascorbic acid, the amount of [$^3$H]DA uptake in the cell was measured. The final concentration of [$^3$H]DA was 20 nM. Furthermore, the cells were incubated at 22° C. for 10 minutes. The results are shown in a mean value±standard error (n=9-12). The measurement results are shown in FIG. 26. In the cell in which the expression vector for expressing the full length Gene 1 had been transfected, it was shown that the reduction of the uptake amount of [$^3$H]DA induced by methamphetamine was suppressed (* $P<0.05$ compared with the pcDNA-DEST53 vector treated cell. #$P<0.05$ compared with the full length Gene 1 treated cell. $ $P<0.05$ compared with the Gene 1 fragment treated cell. + $P<0.05$ compared with the methamphetamine+pcDNA-DEST53 vector treated cell).

On the other hand, as a result of the measurement of the expression amount of intracellular Gene 1 mRNA by the RT-PCR method, in the cell in which the expression vector for expressing the full length Gene 1 was transfected, the significant increase in the expression amount of Gene 1 mRNA was confirmed (FIG. 27).

The above-mentioned results suggest that the Gene 1 suppresses the reduction of uptake of dopamine into the cell induced by methamphetamine.

5-7. Localization of Gene 1 in the Nucleus Accumbens after Continuous Administration of Methamphetamine A rabbit was immunized with the partial peptide encoded by Gene 1 (S-3 antigen: CNTAFRGLRQHPRTQLL: SEQ ID NO.: 19 or S-4 antigen: CMSVDSRFRGKGIAKALG: SEQ ID NO.: 20) as an antigen so as to obtain two kinds of polyclonal antibodies (Gene 1 antibody S-3 and Gene 1 antibody S-4). On the other hand, methamphetamine (2 mg/kg, s.c.) was administered to mice for six days. 24 hours after the final administration of methamphetamine, the mice were subjected to decapitation. A specimen sample of the nucleus accumbens was produced. By using the above-mentioned polyclonal antibody (Gene 1 antibody S-3), immunostaining was carried out (FIG. 28). The staining results shown in FIG. 28 shows that Gene 1 is localized in the cytoplasm of the nerve cell. Also when Gene 1 antibody S-4 is used, the same stained image was obtained (not shown).

6. Change in Expression of Gene 1 mRNA in Nicotine, Alcohol and Phencyclidine The responsibility of Gene 1 to nicotine, alcohol and phencyclidine was examined.

(1) Nicotine

Nicotine (0.05-1.0 mg/kg, s.c.) was administered to mice for 12 days. Two hours after the final administration, the mice were subjected to decapitation and the Gene 1 mRNA amount in the nucleus accumbens was measured by a RT-PCR method. The measurement results are shown in FIG. 29(*a*). The results are shown in a mean value±standard error (n=5). As shown in the figure, the correlation between the administration of nicotine and the expression amount of Gene 1 was observed (* $P<0.05$ compared with the physiological saline solution-administered group).

(2) Alcohol

A mouse was fed with 6% ethanol or water (control) for 12 days, and then was subjected to decapitation. The amount of Gene 1 mRNA in the nucleus accumbens was measured by a RT-PCR method. The measurement results are shown in FIG. 29 (*b*). The results are shown in a mean value±standard error (n=7-8). As shown in the figure, no significant correlation between the administration of ethanol and the expression amount of Gene 1 was observed.

(3) Phencyclidine

Phencyclidine (10 mg/kg, s.c.) was administered to mice for 14 days. Two hours after the final administration, the mice were subjected to decapitation and the Gene 1 mRNA amount in the cortex of frontal lobe was measured by a RT-PCR method. The measurement results are shown in FIG. 29(*c*). The results are shown in a mean value±standard error (n=8-9). As shown in the figure, no significant correlation between the administration of phencyclidine and the expression amount of Gene 1 was observed.

7. Expression of Gene 3 (Piccolo)

The expression state of Piccolo protein in the nerve cell was examined by the following procedure. By using cultured midbrain cells extracted from 13-day old rat, fluorescence double staining of tyrosine hydroxylase and Piccolo was carried out. The staining results are shown in FIGS. 30 and 31. This results show that the Piccolo protein is expressed in the anterior ganglion of the dopaminergic nerve cell and the midbrain dopamine neuron.

8. Effect of Piccolo on Suppression of Dopamine Uptake by Methamphetamine 8-1. Effect of Piccolo C2a Domain on the Suppression of Dopamine Uptake in PC12 Cell in which the Human Dopamine Transporter was Forcedly Expressed An expression vector for expressing certain domains (CA2 and PDZ) of Piccolo was constructed (not shown). This expression vector was transfected into the PC12 cell in which the human dopamine transporter was forcedly expressed, then 1 μM methamphetamine was acted on the cell for 30 minutes. Then, the amount of uptake of dopamine into the cell was measured. Note here that dopamine labeled with $^3H$ was acted on for 10 minutes so that the final concentration became 20 mM. The measurement result is shown in FIG. 32. As shown in FIG. 32, when Piccolo C2A domain was expressed in the PC12 cell in which a human dopamine transporter was forcedly expressed, the suppression effect of uptake of dopamine by methamphetamine was reduced.

8-2. Effect of Piccolo Expression Suppression on Uptake of Dopamine in PC12 Cell in Which Human Dopamine Transporter was Forcedly Expressed Into the PC12 cell in which a human dopamine transporter was forcedly expressed, the oligonucleotide antisense or sense of the Piccolo protein was introduced, and then dopamine labeled with $^3H$ was acted on for 10 minutes so that the final concentration became 20 nM and the radioactivity in the cell was measured. The measurement results are shown in FIG. 33. This results suggest that the Piccolo inhibits the suppression of uptake of dopamine by methamphetamine in the PC12 cell in which a human dopamine transporter was forcedly expressed.

8-3. Relation Between Dopamine Transporter and Piccolo Protein in PC12 Cell (1) Effect of Piccolo on Intracellular Movement of Dopamine Transporter by Methamphetamine In the PC12 cell, the human dopamine transporter was forcedly expressed and fluorescence immunostaining of a human dopamine transporter was carried out before and after methamphetamine was acted. When methamphetamine was acted on, the intracellular movement of the human dopamine transporter was observed. Furthermore, in the same cell, when the C2A domain of Piccolo was also expressed, the same intracellular localization was observed in both proteins.

From the above-mentioned results, it was determined that the Piccolo CA2 domain promoted the intracellular movement of the dopamine transporter by methamphetamine.

(2) Localization of Piccolo in Dopaminergic Nerve Cell

The expression state of the Piccolo protein in the dopaminergic nerve cell was examined by the following procedure. By using the dopaminergic nerve cell extracted from 13-day fetal rat midbrain, double staining of Piccolo and dopamine transporter was carried out. The staining results were sown in FIG. 35. FIG. 35 shows that the dopamine transporter and the Piccolo are localized in the same region in the dopaminergic nerve cell.

From the above-mentioned results (1) and (2), it was shown that when methamphetamine is acted on, internalization of the dopamine transporter occurs (FIG. 36(*a*)) and that the dopamine transporter and the C2A domain of the Piccolo were expressed in the same place (FIG. 36(*b*)).

9. Conclusion

From the experimental results, it was clarified that in Genes 1 to 3 that has been successfully identified, the expression level in the central nervous system tissue was increased in accordance with the formation of the drug dependence. Furthermore, it was clarified that Gene 1 was involved in the uptake of dopamine into the nerve cell. Furthermore, it was determined that Gene 1 had responsibility to nicotine. It was determined that Gene 3 (Piccolo) was involved in the internalization of the dopamine transporter. Thus, genes having the strong relationship with respect to the drug dependence were identified. Furthermore, the human homologous genes of Genes 1 to 3 were also identified. These genes are expected to be useful in the diagnosis and treatment of drug dependence.

INDUSTRIAL APPLICABILITY

The mental disorder-related genes provided by the present invention are used in screening of compound effective for a mental disorder or treatment, diagnosis and study of the mental disorder, and the like.

The present invention is not limited to the description of the above exemplary embodiments and Examples. A variety of modifications, which are within the scopes of the following claims and which are easily achieved by a person skilled in the art, are included in the present invention.

Contents of the theses, Publication of Patent Applications, Patent Publications, and other published documents referred to in this specification are herein incorporated by reference in its entity.

The invention claimed is:

1. A method for diagnosing methamphetamine dependence in a subject, the method comprising the steps of:

a) obtaining a biological sample from the subject, wherein the biological sample is obtained from the nucleus accumbens, the striatum, or blood; and b) determining the expression level in the biological sample of a gene having a base sequence of SEQ ID NO.: 4, wherein an increase in the expression level compared to a control is indicative of methamphetamine dependence in the subject.

* * * * *

SEQUENCE LISTING

```
<160> NUMBER OF SEQ ID NOS: 40

<210> SEQ ID NO 1
<211> LENGTH: 2785
<212> TYPE: DNA
<213> ORGANISM: Mus musculus

<400> SEQUENCE: 1

tgaggcactg ccgggggcca agaaggacgc gctgctcgtc gccgccggag ccatgtggcc      60

cccgctgccc gccgcgcccg ggccggccgc cgcacccccca cccgcggcag gtccccagcc    120

ccacggaggc accgggggcg cggggccgcc ggaggggcgc ggcgtgtgca tccgcgagtt    180

ccgcgcagcc gagcaggagg cggcgcgccg catcttctac gacggcatct tggagcgcat    240

ccccaacacg gctttccgcg gcctgcggca gcacccgcgc acccaactgc tctacgccct    300

gctggccgcc ctctgttttg ctgtgacccg ctcactgctg ctgacatgcc tggtgccggc    360

cgggctcctg gccctgcgct actactacag ccgcaaggtg attctggcct acctggagtg    420

tgcgctgcac acggacatgg ctgacattga gcagtactac atgaagccac ctggttcctg    480

tttctgggtg gctgtgctgg acggcaacgt tgtgggcatc gtggccgcac gggcccatga    540

ggaggacaac acagtggagc tgctccgcat gtccgtggac tcgcgtttcc gcggaaaagg    600

catcgccaag gctctgggca ggagggtgtt ggagtttgcc atgctgcaca actactctgc    660

agtggtactg ggcaccacag ccgttaaggt ggccgcccac aagctctatg agtcactggg    720

cttcagacac atgggcgcga gtgatcacta cgtgctgcct ggcatgaccc tctcgctggc    780

cgagcgcctc ttcttccagg tccgctacca ccgctaccgc ctgcagctgc gcgaggagtg    840

accaccacca cctgcccacc accctgtctg cccccgtcca cctctgccct cttgctcact    900

gcctagtgcg gccctgcttt ccaatgctca ccttggcatt tgtttgggtt ttcctttttc    960

agcatcatgc tggttcatca cctggctggt tctggggcca cagggtccca gtccagagtg   1020

ctcatctgca acactctggt ggggtggatt gtctgcagcc atggcccttg cctccccagc   1080

ccatcagagt ggctcatcat gccttgaaga gcagcattgt ggaccatctg aactatccac   1140

aaagctgccc agcctgcctc catcagggaa ggactagcct tgcccatcaa gcacagaacc   1200

tctacaacaa cccccccccc cccaaggagc agaaccctgg cccccagcca ggctaaggct   1260

caactattgg cctctggaag agtggtctgc tgggctggcc agccactgcc ccatgggagg   1320

ctgagctggt cccaggccct gctttgccct gtgcatgcta aggacatggc ctggctgcag   1380
```

-continued catgccgcat gccacagccc cctgccccac tatcctgccc agcctggacc tcaggcctga 1440
gctggtgagc tcccttgtcc tgtcctgagc tggcctctgg agggcctacc tgcctgaccc 1500
tgtctactct ctggtgaggc ctggcctggc ctaacctggc tctatccact cctgctttgc 1560
ttcgaaatca tcttacctct ttccctttt ggtccccgtg cctccttgct ctggctgact 1620
tggctggtca cccgggtttg gttcctgtag caatccactg cacagcatgg tggggatttc 1680
atgggggtgg gggggacacc tcccccaaca cctgttagac caggtggcca cctcccagct 1740
gcctgaggtc ctgtggcctc atgctgtttg tggggtctgc cctgtgaatg taactagccc 1800
aggctgttgt tggcaatgcc tgccacagct tctcccagcc tgaaacaacc cattctctaa 1860
taagttacgt agacagaata gcactctgca tgactttaat tactgggaca aaatggtagt 1920
ttgagcctcc agacacacat ctgtgtggtg ctagcatacg catggtctct ggccccattt 1980
gatgggggtg ggtggccggg taggtggaag atttcagttt gaagtatgga aggagactct 2040
aatttagtgt aaacacccct aaagtgccct cacaacacag tctgtgaggc tcaggttgcc 2100
ccttgattcc ttgtatgcag gattgagggg actggagggt cctaaagcct cataggaagg 2160
gctgggcact gcctcggggg aagaagctgg tggttggggt gggtccaggt atcacccact 2220
acagactact ctgctaggtc aactgttcct ggcctctcct ttttgaggtt ctacttcaga 2280
tccagcctag atgggggtgg gtatggccta ggacagggaa aggcagtagc tggcagtggt 2340
catgaggcca gctgaaactt ggacttagct ttagtgcagg gggtgcataa aggcccgtcc 2400
acattcctct gtgtggggct tggggtgagg agtggcaggc taggtagacc atagagctgg 2460
gcccctggca ccaaggctac attattagaa aggctcttta gagttaatga gttggtggaa 2520
caagcccagc ttcctgaggg gccttttgtc ctgttagcaa ttgaggcatt tgcagaacac 2580
tgtacagacc ccgctctccc ctgtacattc ctccctggtg gtgcccggtc cccgcttggg 2640
gatgggagtt ttgtagactg tacagaaatt ggcaccctat tttcttgcag ctctcagatt 2700
ttgttaatct ggattataca gacagatgta aagtgtttta gcaaaatgga aaaaaaaaaa 2760
aaaaaaaaaa aaaaaaaaaa aaaaa 2785

<210> SEQ ID NO 2
<211> LENGTH: 4551
<212> TYPE: DNA
<213> ORGANISM: Mus musculus

<400> SEQUENCE: 2
ggcggcgcgc cttgtccctg acggcgatcc gtagcgctgg gagtcagcgg cggaaacatg 60
gcggtcgtgt cggtcctagc gaaagtttct accgaggcct tgcggtgcta gtgcgggagg 120
cctcgggctc acgtccccac atcacctccg cgttctggct cggaggctcc gcgccctttg 180
gctctgcgag cttcgcagcg gaaagagcga ggctcgctgg cgaccgctga ctcgggtcat 240
tacaaagaaa acttctgaga gaatgttgga gtaggcatta ccaacacctt ggctttattg 300
aatgaaatac aggaagttaa tttttgtgcc tcttgggacc ctccagtgcc agattacatg 360
tgcagatcac tgcgatactg tgttagtcat tgtctctatc tagcaatgac taggctggaa 420
gaagtaaata gagaagtgaa catgcattcc tccgtgcggt acctcggcta tctagccagg 480
atcaacttac ttgtggccat atgtttaggc ctttatgtaa gatgggaaaa aacagcaaat 540
tccttaattt tggtgatttt tatcctcggc ctctttgttc ttgggatcgc cagcatactc 600
tactattact tttcaatgga agcagccagt ttaagtctct ccaatctctg gtttggattt 660
ctgcttggcc ttctgtgttt tcttgataat tcatccttta aaagtgatgt gaaagaagaa 720

-continued

```
acaaccaaat atttgcttct gacatctata gttttaagga tattgtgtgc tttggtggag    780
agaatttctg gatatgtccg ccatcggcct actttactaa ccacagtgga gtttctggaa    840
cttgttgggt ttgccatcgc cagcacaact atgttggtgg agaagtctct gagtgttatt    900
ttgctggtta tggctttggc catgctcatt atcgacctga gaatgaagtc ttttctagct    960
attccaaact taatcatttt ttcagtattg ttatttttct cttcattgga aactccccaa   1020
aatccaattg cttttgcatg ttttttttatt tgcctggtaa ctgatccttt tcttgacatt   1080
tattttagtg gactttcagt aactgagagg tggaaacctt ttctgcatcg tgggagaatt   1140
tgcaggagac tttctgtgct tttcactgca atgattgagc ttacattctt catcctttca   1200
gcatttaaac ttagagacac tcatctctgg tattttgtga taccaggttt ttccattttc   1260
ggatttttct ggatgatttg ccatattatt tttcttttaa ctctttgggg atttcatact   1320
aagttgaatg actgccataa agtgtatatc aaccacaggg cagataacaa tagccttgac   1380
agaatcatgg catccaaagg gatgcgtcat ttttgcttaa tttcagagca gttagttttt   1440
tttagtcttc ttgcaacggc aattttggga gcagtctcct ggcagccaac caatggaatc   1500
ttcttgagca tgtttctcat tgtcttgccg ctggagtcca tggctcatgg gctcttccat   1560
gaacttggca actgcttagg gggaacctct gttggatacg ctattgtgat ccctaccaac   1620
ttctgcagcc ctgatggcca gccaacactg cttccgccag aacatgtaca ggagttaaat   1680
ttgaggtcta ctggcatgct caatgccatc caaagatttt ttgcatatca tatgattgag   1740
acctatggat gtgactattc cacaagtggg ctgtcttttg atactctgca ttccaaactg   1800
aaagctttcc ttgaacttcg gacagtggat ggacctagac atgatacata tgttttatat   1860
tacagtggac acacccatgg ctcaggagag tgggccctcg caggtggaga catacttcgc   1920
cttgatacgc ttttagaatg gtggagagag aagaacggtt ccttctgttc ccggcttatc   1980
atcatcttag acagcgagaa ttcaacccca tgggtgaaag aagtgagaaa gattaatgac   2040
cagtatgttg cagttcaggg agctgagctg gcgaagacag tagatattga agaagctgac   2100
ccgccacagc tgggtgactt tactagagac tgggtagaat acaactgtaa ctccacaaac   2160
aacatctgct ggactgagaa ggggcgcaca gtgagggccg tgtatggcgt gtcaaagcgc   2220
tggagcgact acacgctgca cctgccgaca ggaagcgatg tggccaagca ctggatgtta   2280
cacttccctc gggttacgta tccgttagtg cacttggcca actggttatg tggcctgaac   2340
ctcttttggg tctgcaaagc ttgttttagg tgcttgaaaa ggttaaaaat gagttggttt   2400
cttcctacag tgctggacac aggacaaggc tttaaacttg tcaaatctta atgtggacat   2460
caaggaaggc tattattgag agttcatgtt accatttatc agtaacttgc catttttttgt   2520
atgctgtatt tttatttgtg gaaagtatct tgctacattt gtagctgttc tcactttgtc   2580
ttttcttaag taattatggg atgtggaaga tattgggaat atgcatgatt ttatactaaa   2640
agtatatgga gggtcatgaa aatgctgaat gtaaatgtgt aagagatgtt aaaagtaaca   2700
gtgcactttc aaataacttt ccatttgtct ccaatgaaaa gaaacacagt tgtctgtgct   2760
ctggagtggc caatggacaa ttcctaatgc cttattttct aggcacccgt tagagaatgt   2820
agaccagaca agtgtgtttt aagagaacta ccagtttact tagtaggaga ttctttcatg   2880
tgtgtgattc atataggttt ggccccagga ctgtttgcag aagtataaat acttggagca   2940
ggaagagacc tgctcataat gactgcaaaa tgccctttta ccaccacacc cagatgtctt   3000
ggctatgacc tttacagtac agcagaaaag ccccaactgc ctttgagatg aaagcattgt   3060
```

-continued

```
taatgtaggt aacaataaga gcttacatgc tacaaagtgt tccttcatgg ttagtgaggg   3120

actttgaaaa tactggtaaa tttaagagtc cttctcaggg taattttgtt ttcttaatga   3180

gtagtatttc cagctacaaa ttcctttcaa gtaaattgcc attcttttca aaaagtacac   3240

acttacaaaa ataaatgtat cagtttctca ttgaccgatt cttcctgtct tacgtattta   3300

tgaggagtta gtactctgcc atgaaagttg cttttcagtc ctattgtaat aacttttttc   3360

tgctgaaggt caaggatggg aacagatcat tttgttgttg ttgttgttat atacctgtat   3420

tgtattatgt aaaaaagtat tcattttggc agttttaggt aagcataatg gtatggttgt   3480

aatttgtaaa ctttaattca gtgttttgtt ggagtaaagt aggcgctgat caggatatct   3540

ccttaagagg taagtcactt cctgtcccct tccaattatc cttacattct agattttcat   3600

ctttgaaaga gggaggtata attaaagtgg agattagact ttgttaccat ggtgacttct   3660

caccgttgaa gccatttttc catgcccaga gagggaaggt aacggatgca tctaccattt   3720

tctaccaatg acttgaaaac tgacatttta tttagaaaga agtcacacca tcagggaact   3780

tgtatactgt tatctatgca gcattgctac agcctatttc tatgttttga atattgtact   3840

cttaatactt tgaataatat tttgtaaaaa attaattttt catttaatgt gaaattaaga   3900

gttcctgaat attttactgt attaaaagtg gaagttatac aaaatgcctt tgcttttaga   3960

gtttatgttt ggtggcatgt tgatttgaaa atatttcctt attccagaat actgaagaat   4020

tgatacaata ttgaaagtta gtggcatcct atatacaata tttttttaa aaaatgaatc   4080

ttgttttaca actagaaata cagatagtaa atttcactga ataaatcatt catttgtgtg   4140

catcttgaat ttcagatggg tgccatttca catcagtttt gtataatttt taggttcttc   4200

aggtccacaa ttaaataagg aaactagcgt tgagatgtta ccttgctgtg cacatatctg   4260

tgtatcagga gctaggctcc cctacctaag tggaaaggca ttgctctctc tagctctaat   4320

cctacaattc ctttcttcct ttccatatga aacaactcta tacacagcca tgggtattgt   4380

ctatgatcta attattctaa gtatttttct gtgattgatt ttattacacc ttcccaaatg   4440

ctcttaataa tttaacatag aaatttgtat tttataaatt atgaaactaa ggcagtggac   4500

tcttacaaaa atgacagaat aataaactgc tctgaagcta atttgagact c            4551
```

<210> SEQ ID NO 3
<211> LENGTH: 16754
<212> TYPE: DNA
<213> ORGANISM: Mus musculus

<400> SEQUENCE: 3

```
gcggggcgcg gggcggggcc gtcggcgcgg ggctggccga gctccgctgc ttctgggctg     60

ctccggcgct gaggaggcaa ccgggagaca gggcgtgaga agcttccctg gcgctgtcca    120

acatggagga gctgcccggc gccggcacag cctgcggact ggtctgagct cgccccactt    180

ccccaggcag ccgggagggc gcggagcccc cagggctggg cagcctgcac gccccggggc    240

ggaccccggc tggcggggct cggacggccg cgggcttctg caccgggacg tgtcccgccg    300

agccatgggc aacgaggcga gcttggaagg ggaagggctc cccgaagggt tggcggcggc    360

cgcaggcggg gctggcggct ccgggagcgc cctgcacccg gggatcccag ccggcatgga    420

ggcggacctg agccagctga gcgaggagga gaggagacag atcgctgctg tcatgtcaag    480

ggcgcagggg ctgcccaagg gaagcgtccc cgcggccgct gcggagtcgc cctccatgca    540

caggaaacaa gagttggata gtagtcaggc tccacagcaa cccggaaagc caccggaccc    600

tgggcgtccc cctcagcatg gtcttagcaa aagcagaact acggacacgt ttaggtcaga    660
```

-continued

```
gcagaagctg cctggaagga gcccgtccac tattagcttg aaagaatcca agtccagaac    720
tgattttaag gaagaataca agtctagtat gatgcctggt ttcttctcag aagttaatcc    780
tttaagtgct gtctcctctg ttgtaaataa attcaaccct tttgatttga tatcagactc    840
cgaggcagtc caggaggaaa ctacaaagaa acaaaaagtt gctcagaagg accaagggaa    900
atcggaagga atcacaaaac cttccttaca gcaaccatca cccaagttga tccctaaaca    960
gcaaggacca gggaaggaag tgatcccgca ggatatcccc tccaagtcag tatcctccca   1020
gcaagcagaa aaaacaaaac cacaagcccc tggcacagca aaaccttccc agcagagtcc   1080
agcccaaaca ccagctcagc aagcaaaacc tgtagcccaa cagcctggac ctgcaaaggc   1140
cacagtccag caaccagggc cagcaaagtc cccagctcaa ccagcaggga cagggaagtc   1200
cccagcacaa cctccagtga cagccaagcc cccagctcaa caggctggct tagagaagac   1260
ctcattgcag cagcctgggc caaagtctct agctcagact cctggtcagg gaaaggttcc   1320
accagggcca gcaaagtccc cagcccagca gccagggaca gctaaactcc cagcccaaca   1380
gcctggccca cagactgcat ctaaggtacc tgggcctaca aaaactccag ctcagctatc   1440
tggacctgga aaaacaccag ctcagcagcc tggtccaaca aagccttcac ctcagcagcc   1500
cattccagca aagccccagc ctcaacaacc tgttgccaca aaacctcagc ctcaacagcc   1560
agccccagca aagccccagc ctcagcaccc aactccagca aagccccagc ctcagcagcc   1620
caccccagca aagccccagc ctcagcagcc caccccagca aagccccagc ctcaacaccc   1680
aggcctggga aaaccttcag ctcaacaacc ttctaaatca ataagccaaa cggtaacagg   1740
aagacctctg caagcaccac caacttctgc agcacaggcg ccagcacaag gcctctctaa   1800
aaccatctgt cctctttgca acaccactga gcttctgttg catactccag aaaaggccaa   1860
ttttaacaca tgtactgagt gtcaaagcac cgtgtgtagc ctctgtggtt ttaaccccaa   1920
tcctcactta actgagatca aagagtggct ctgtttaaac tgtcagatgc aaagagctct   1980
gggaggtgaa ctggcagcaa tcccatcctc accgcagcca accccaaagg ctgcctcagt   2040
acagccagca acagccagca aatcacctgt accgtcacag caggcttccc caaagaagga   2100
acttccatcc aaacaggaca gccccaaagc accggagtcc aaaaagccac cgccactggt   2160
gaaacagcca acccttcatg gacctacccc ggctacagcc ccacagcctc cagtggcaga   2220
ggccttacct aagccagccc ctcccaagaa gccttctgca gccctacccg aacaagcaaa   2280
ggcccctgtt gcagatgttg aaccaaagca accgaagacg acagagacac tcacagatag   2340
cccatcttca gcagcagcaa cctcaaagcc tgctattctg agctctcaag tgcaggcaca   2400
ggctcaagtg acaacggccc ctcctttgaa aacagactct gccaaaactt cacagagttt   2460
cccaccaaca ggagatacaa ttaccccact tgattctaaa gccatgccca ggcctgcatc   2520
agactcaaaa attgtttcac atcctgggcc cacttctgag agcaaggatc cagttcagaa   2580
gaaggaggag cctaagaaag cacaaaccaa ggtgacccct aaaccagata caaagccagt   2640
accaaaagga tccccaacac cgtctggcac acgacctacg actggccaag ccacacccca   2700
gtctcagcag cccccgaagc ctccggagca gtcaagacgg ttcagtttga atctgggggg   2760
tatcgctgat gcccccaaat cacagcccac aactcctcaa gaaactgtga cagggaagct   2820
attcgggttc ggagcatcca tctttagcca agcatcaaac ttaatttcca cagcaggtca   2880
gcaagcacct catccacaga ctgggccagc tgccccatca aagcaagccc ctcccccatc   2940
ccagactctg gctgctcagg gaccacccaa gtccacaggt cagcacccat cagcacctgc   3000
```

-continued

```
caagaccact gctgtgaaga aggaaacaaa aggcccggca gctgaaaact tagaggccaa   3060
acctgcgcaa gctccaacag tgaagaaggc agagaaagac aagaagcacc cacctgggaa   3120
ggtcagcaaa cctccaccta cagagcccga gaaggccgtc ctcgcccaga agccagacaa   3180
gaccaccaaa cccaaaccgg cctgtcctct ctgcagaacg gaactcaacg tagggtctca   3240
ggatcctccc aacttcaaca cctgcacaga atgcaagaat caagtttgca atctctgtgg   3300
atttaaccca acgccccacc tgactgagat tcaagaatgg ctttgtttaa actgtcagac   3360
acagagagca atatcaggac aacttggaga tatggacaaa atgccacctg catcctcagg   3420
acccaaagca tcccccgtgc ctgcccctgc agaaccccca cctcagaaaa caccaacagc   3480
tgcccacgcg aaaggtaaaa agaaggaaac agaagtaaaa gcagaaactg aaaaacagat   3540
cccagagaaa gaaacaccat caattgagaa aaccccgcca gcggtcgcca cagatcaaaa   3600
actagaagaa agtgaagtaa ccaaaagcct agtttctgtc ctgccagaaa agaaaccatc   3660
cgaggaagaa aaagccctgc ctgcagacaa aaaggaaaag aagccacctg ctgcagaagc   3720
gccaccactt gaagaaaaga agccgatccc tgatgatcag aaattacccc cagacgcaaa   3780
accatcggcc tcagaggggg aggagaaacg tgatctactt aaagctcacg tacaaattcc   3840
cgaagaagga cccataggca aagtggcttc actggcttgt gaaggagagc agcagccaga   3900
caccaggcct gaagatctgc caggcgccac acctcagacg ttacccaagg acagacagaa   3960
ggaaagcaga gacgtaacac agcctcaggc agaaggcact gcaaaggaag gccgaggggga   4020
gcccagcaaa gacaggacag aaaaggaaga ggacaaatca gacacttcca gttctcagca   4080
acccaagagc ccacaaggcc tgagtgacac agggtactcc tctgacggaa tatccggctc   4140
tcttggggaa atccccagtc ttatacccag tgatgagaaa gatttgctaa aaggactcaa   4200
aaaagactcg ttctcgcaag aaagcagccc ttccagcccc tcagacttag cgaagttgga   4260
aagtacagta ctgtccattt tggaagctca ggcaagcaca cttgtaggtg aaaaggcaga   4320
aaagaaaaca cagccccaga aggtttctcc tgaacaacct caggaccagc agaaaactca   4380
gactccatcc gaaacacggg atatttctat ttcagaagaa gagatcaaag agagtcaaga   4440
aaagaaagtt acttcaaaaa aggatagcgc acaaggtttt ccttccagga aggagcacaa   4500
agagaatcct gagctggtcg atgacctaag tccgcgaaga gcatcctatg attcggttga   4560
agacagcagc gaaagtgaaa actcccctgt tgctcgcagg aagcggagaa ctagcattgg   4620
ctcatcaagc agcgaggagt ataagcagga agacagtcaa ggctcggggg aagacgagga   4680
cttcattcga aagcagatta tagagatgag cgctgatgag gatgcttcag gctctgagga   4740
tgaagagttc atcaggagtc agctcaaaga gattggtggt gttactgaga gccagaagag   4800
ggaggaaaca aaggggaaag gaaaaagccc agcagggaaa cacagacgtc tgactcgaaa   4860
gagtagtacc agcttcgacg atgatgctgg gagacgccat tcctggcatg atgaagatga   4920
cgaaactttt gatgaaagtc ctgaactcaa attccgagaa actaaaagcc aggagagtga   4980
ggaactagtt gttgctggag gaggagggtt acgtcgattt aagactatag aactcaacag   5040
tacagtaaca gataagtact ctgcagaatc ctctcagaaa aagacaactt tgtattttga   5100
tgaagagcca gaattagaaa tggaaagtct gacggactca cccgaggaca ggtctagagg   5160
agagggatcc tcgagtctcc atgcatccag cttcactcct ggcacgtccc ctacatcagt   5220
atcatcactt gatgaagaca gtgacagcag cccaagtcac aaaaaaggag aaagcaagca   5280
gcagcgcaaa gctcggcaca ggtcccatgg ccctctttta cctaccattg aagattcttc   5340
cgaggaagaa gaactacgag aggaagagga gttattaaaa gagcaagaga agcagagaga   5400
```

-continued

```
actggagcag cagcagagga agagttctag taagaaatcg aagaaagaca aagatgaact   5460
tcgagctcag aggaggagag aaagaccaaa gacgccaccc agtaatctct ctcccatcga   5520
ggatgcgtct cccacagaag aattgcgcca ggcagcagaa atggaggagc tccataggtc   5580
ctcttgttct gaatactcgc ctagcataga atcagaccca gaaggatttg agataagccc   5640
cgagaaaata atagaagttc aaaaagttta taaattgccc acagctgtgt ctttatactc   5700
accaacagat gagcaatctg ttatgcagaa agaaggtgct cagaaggctt taaaaagcgc   5760
tgaggagatg tatgaagaaa tgatgcacaa accccacaaa tataaagctt ttccagctgc   5820
aaatgaacga gacgaagtgt ttgaaaaaga gccattgtat ggtggtatgt taatagagga   5880
ctacatttat gaatctttag tagaggacac atacaatgga tcagtagatg gcagcctgct   5940
caccaggcaa gatgaacaaa atggatttat gccgcagaga ggaagagagc aaaaaataag   6000
actacgggag cagatttatg atgatcctat gcagaaaatc acagacctcc agaaagagtt   6060
ttatgaatta gaaagcttac attctattgt gcctcaagaa gacattgttt caagctctta   6120
tatcattcca gaaagccatg agatagtgga tctgggtagc atggtaactt ctaccagcga   6180
agaaaagaaa ctgttagatg cagatgctgc ttatgaagaa ctcatgaagc ggcaacagat   6240
gcaagtaaca gatggatcca gcctcataca gactaccatg ggggatgaca tggctgagtc   6300
cactctggac tttgacaggg tacaagacgc atctttgaca tcaagtatcc tttctggagc   6360
atctcttaca gactcaacca gcagtgcaac tctctctatc ccagatgtta agataaccca   6420
acatttttca acagaagaat ttgaggatga atatgtaact gattatacaa gagaaattca   6480
agagataatt gcccatgaat ctctgatatt gacctactct gagccttcag agagtgctac   6540
gtctgtccca ccttctgaca caccttctct cacatcatct atttcttcag tttgtaccac   6600
agatagctcc tcacctgtca ctaccctcga tagcctaaca actgtttata cggagccagc   6660
agatgtaata actaaattta aagactctga ggaaatttct tcaacttatt ttccaggcag   6720
cgttatcgac tatccagaag atataggtgt atccttagat cgaaccatca caccagaaag   6780
tagaactaac gctgatcaga ttatgatttc ttttcctggt atagcaccat ctatcacaga   6840
atctgtagca actaaacctg agaggccaca agctgacacg atttccactg acttacctat   6900
atctgaaaag gagttgataa aaggcaagaa agaaactggg gatggaatta ttctggaagt   6960
tttggatgct tacaaagata aaagggaaga gtctgaggct gaactaacaa aaattagctt   7020
acctgagact gggttggccc caacaccttc ttctcaaact aaggagcaac ctggatcccc   7080
acactctgta tctggagaga tctcgggtca ggaaaagccc acatacaggt cgccgtctgg   7140
cggtcttcct gtttctaccc atccatccaa atctcaccca tttttccgaa gttcttcttt   7200
ggacatatca gcccagccac cccctcctcc tccacctcct cctcctcctc cgccaccccc   7260
tcctcctccc ccacccccac cgttgcctcc agcaacttct cctaagccac ccacttatcc   7320
taaaagaaag ttggcagctg cagctccagt ggctccaact gctattgtta cggcccatgc   7380
tgatgctatt cctactgtag aggccacagc tgcccgcagg agcaatgggt tacctgcaac   7440
taaaatatgt gctgctgccc ctcctcctgt ccctcctaag ccttcttcaa ttccaactgg   7500
acttgtattt acacatagac cagaggcaag caaacctcca attgccccca agccagcagt   7560
ccctgagatt ccagtgacta cacagaaaac aacagacacg tgccccaaac caacaggtct   7620
acctttaaca tcaaatatgt ccttaaattt agtgacttca gcagactaca aactgccgtc   7680
ccctacctct ccactttccc cacactcgaa taaatcctca ccgagatatt ctaagtctct   7740
```

-continued

```
catggagact tatgtggtca ttacattgcc ctctgaacct gggactccaa cagattcttc   7800
tgctgcccaa gccattacaa gttggccctt gggatcaccc ccaaaagatc tggtttccct   7860
tgaaacggta ttttctgtag ttcctcccat gacatctaca gaaattccaa gtgcttcaca   7920
gccaacccta tatacatctg gagctttggg gacattttct gttacccctg ctgtaacagc   7980
ctctctgttt caaacagtac caacttcact tacacagttt cttccagcag aagcttcaaa   8040
acccgaagtc tctgcagtga gtagtgcagt cccaagtgtt gctcccagga gtgtttccat   8100
accaattcct ccagagcctc ttgctctaga caggcatcag tataaggaaa atggaaagtt   8160
gccacttatt ggagatgcca ttgatttgcg tacaatacca aaatcagaag ttaaagtaac   8220
tgaaaaatgt atggatcttt ctgcttctgc aatggatgtg aaaaggcaga ccacagcgaa   8280
tgaggtttac aggcgacaaa ttagtgctgt ccaaccttct atcataaacc tcagtgcagc   8340
ttcctcctta ggaactccag tcaccatgga ctctaagaca gtggctgttg tcacgtgcac   8400
agacactaca atttacacaa caggcacaga aagccaagtg ggtatagaac atgcagtaac   8460
atcaccactg cagcttacta catcaaaaca tactgagtta caatacagaa aacctagtag   8520
ccaggctttt cccatgattc gagatgaagc accaataaac ttatcattag gtccttccac   8580
tcaggcagta acattggctg tcacaaagcc tgtcactgta cctcctgttg gtgttacaaa   8640
tggatggact gacagcacca tatctcaggg gatcactgat ggagaagtgg tagatctcag   8700
cacatcaaag tctcatagga ctgttgtgac aatggatgaa tctacttcaa atgtagtgac   8760
taaaatcata gaagatgatg aaaagccagt tgatttgact gcaggaagac gagctgtgtg   8820
ctgtgacatg gtttacaagt tgccttttgg acggagctgc acagcacagc agcctgcaac   8880
taccattcct gaagaccgtt ttggttatag ggatgaccac tatcaatatg atagatcagg   8940
gccatatggt tacagaggga ttggtggaat gaaaccttcc atgtcagaca ctaatttagc   9000
agaagctgga catttttct ataaaagcaa gaatgctttt gattattctg gaggaactga   9060
agcagcagta gatctaactt cagggagagt gtctacaggt gaggtaatgg attattcaag   9120
caagactaca ggcccatacc cagaaacacg ccaagtcatt tcgggagttg ggattagtac   9180
cccgcagtat tccacagcaa gaatgactcc acctcctgga ccgcagtatg gtgtgggaag   9240
tgttttgagg tcatctaatg gtgttgtcta ttcttcagta gcaactccaa tcccctccac   9300
atttgctatc accactcaac ctggctccat tttcagcacc acggtcaggg atttatctgg   9360
cattcataca acagatgcaa taacttcatt atcagccctg catcaaagcc agccaatgcc   9420
tagatcgtat ttcataacaa caggtgcatc agaaacagac atctcagtaa ccagtattga   9480
catcaatgcc agcctgcaaa ctattactat ggaaactctt cctgctgaga caatggactc   9540
tgttcctacc ttaaccaccg cctctgaggt gttttctgag gtggttggag aggaaagcac   9600
tcttttgatt gtccctgatg aagacaaaca acaacagcaa cttgacttgg agcgagagct   9660
cctggaactg gagaaaatta agcaacaacg ctttgctgag gaactggagt gggaacgtca   9720
ggagattcaa aggttccgag aacaagaaaa gatcatggtt caaaagaagc tagaagagct   9780
gcaatctatg aagcagcacc ttctttatca acaagaggaa gagcggcagg cccagttcat   9840
gatgagacag gagacgctag ctcaacaaca gttacaactt gagcagatcc aacagctgca   9900
acaacagctc catcagcagc ttgaggaaca aaaacttcgc cagatctacc agtataacta   9960
cgaaccctct gggactgctt ctccacaaac caccactgaa caggcaattt tggagggtca  10020
gtatgttgct acagagggca gtcagttttg ggccactgaa gatgccacca caacagcgtc  10080
tactgtggta gccattgaaa taccacagag ccaaggatgg tacacggttc agtctgacgg  10140
```

-continued

```
tgtgactcag tacattgccc cacctggcat cttgagcact gtttcggaga tacctctgac  10200
agatgttgtt gtaaaagagg agaaacagcc caaaaagaga agttctggag ctaaagttcg  10260
ggggcagtat gacgagatgg gggaaagcat ggcagatgat ccacggaatt taaaaaagat  10320
agtggacagt ggtgtacaaa ctgacgatga agaaactgct gatcggactt atgcaagtag  10380
gagaagaaga actaaaaaga gcgttgatac cagtgtccaa actgatgacg aagatcagga  10440
tgagtgggat atgccttcta ggtccaggag aaaagcgcga acagggaaat acggagatag  10500
cacggcagag ggtgacaaga ccaaaccccc ttccaaagtc tccagtgtag cagttcaaac  10560
agtcgcagag atatctgtgc aaactgagcc attgggaacc ataagaacac cttccatacg  10620
agcacgggtg gatgccaagg tagaaataat taaacacatt tcagcgcctg aaaagactta  10680
caaagggggc agtttaggat gccaaacaga aacagatcca gacacacaga gccctccata  10740
tatgggtgcc acatctccac ccaaagacaa gaaacgccca acacctttag agattggtta  10800
ctcttcttct caccttcggg cagaccccac agtccagctg gctccttccc cacccaaatc  10860
tccaaaagtc ctttactcac ccatctcacc actttcccca ggccacgcct tagaaccagc  10920
ctttgtacct tatgaaaaac ccctccctga tgacataagt ccacagaaag tactccatcc  10980
agatatggct aaagttcccc cggcaagccc taagacagcc aagatgatgc agcgttcaat  11040
gtctgacccc aagcctctga gtccaacagc agacgaaagt tccagggctc cttttcagta  11100
ttccgagggc ttcacggcta aaggttccca aacaacctct ggtactcaga aaaaagtgaa  11160
gagaacactg ccaaatcccc ctcctgagga ggcgtccacg ggaacacagt caacttacag  11220
caccatgggc actgcttcta ggagaagaat gtgcagaacc aataccatgg ctcgagccaa  11280
aattctccag gacatagacc gagagcttga cctcgtggaa agagagtctg ccaagcttag  11340
aaagaagcaa gcagaacttg atgaagaaga aaaggagatt gatgccaagc tacggtatct  11400
ggaaatggga attaacagga gaaaggaagc actattgaag gagagagaaa aaagagagcg  11460
tgcctacctg caaggggtag ccgaggaccg tgattatatg tctgacagtg aggtcagcag  11520
taccagaccc agccgagtag aaagccagca cggcattgag cggccaagaa cagctcctca  11580
gactgaattc agccagttca taccaccaca aacacaaaca gaagctcagc tagttcctcc  11640
gacaagtcct tacacacaat accagtactc atcacccgct cttcccaccc aagccccgac  11700
cccatacacg caacagtctc attttcaaca gcagacattg taccatcagc aagtgtcacc  11760
ttatcagact caaccaacct tccaagctgt ggccaccatg tccttcacac cccaggctca  11820
acctacccca actccacagc catcctatca attaccatca cagatgatgg tgatacaaca  11880
aaagcctcgg caaaccacat tgtatttgga gcctaagata acttctacct atgaagtgat  11940
tcgcaaccaa cccctgatga ttgctccagt ttctactgat aatacgtatg ctgtttccca  12000
tctcgggagt aagtacaata gtttagactt gagaataggt ttggaggaaa gaagcagtat  12060
ggcaagcagt ccaatatcaa gcatatctgc agactccttc tatgcagaca ttgaccacca  12120
tacttcaagg aattatgtcc taatagatga cattggagac attaccaaag ggacggcagc  12180
tttgagctct gcatttagtc tccatgaaaa ggatctgtcc aaaacagatc gtctccttag  12240
aaccactgag acacggaggt ctcaagaagt gacagacttc ctagcgcctt tgcagacttc  12300
ctccagactg catagctatg tgaaggcaga ggaggatccg atggaggatc cttatgagtt  12360
aaagcttctg aaacatcaga ttaagcaaga attccgtagg ggcacagaga gcttagatca  12420
ccttgctggt ctctcacatt attaccatgc tgatactagc tatagacact tccccaagtc  12480
```

-continued

```
tgaaaagtat agcatcagta gactcaccct ggaaaaacaa gctgccaaac aattgcctgc  12540
agccatactt taccaaaagc aatcaaagca taagaaagca ttaattgacc ctaaaatgtc  12600
taagttttca cctattcaag aaagtagaga ccttgaacct gactatccca cttacttgag  12660
ttctagcact tcgtccattg gtggtatttc ttctagggca aggcttcttc aagatgatat  12720
cacatttggc ctcagaaaaa atattacaga tcaacaaaaa ttcatgggtt catcacttgg  12780
gtcaggactg ggcacgttag gaaataccat ccggtcggct ctacaggatg aagcagataa  12840
gccatacagc agtgggagca ggtccaggcc ttcctctagg ccttcctctg tctatgggct  12900
tgatttatca attaagaggg attcttccag ctcatcacta agattgaaag ctcaagaggc  12960
tgaagctctg gatgtctctt ttggccattc ttcatcttct gccagaacta agcccaccag  13020
cttaccaatc agccagagta gaggaagaat accaattgtg gcccagaatt cagaagaaga  13080
aagtccacta agtcctgttg gccagccaat gggaatggcc agggctgcag ctggaccttt  13140
gccgcccata tctgcagata caagggatca atttggatca agtcactcat tgcctgaagt  13200
tcagcaacac atgagagaag agtcacggac aaggggttat gaccgtgaca tagcattcat  13260
catggatgac ttccaacatg ctatgtctga cagtgaagcc tatcacttgc gtcgggagga  13320
aacggattgg tttgataaac ccagggagtc tcggttggaa aatggccatg gtctggaccg  13380
gaaactgcca gaaagactgg ttcactctag acccctcagt caacatcaag agcaaattct  13440
gcagatgaat gggaagacaa tgcactacat ctttcctcat gcaaggataa aaataaccag  13500
agactctaag gatcacacag tttcaggtaa tgggctagga attagaattg ttggtggtaa  13560
agaaattcct ggacatagtg gagaaattgg agcctatatt gctaagattc ttcctggtgg  13620
aagtgcagaa cactcaggga aacttataga agggatgcaa gttttggaat ggaatggaat  13680
cccgttaact tctaaaacat atgaagaagt acagagcatc attaatcagc aaagtgggga  13740
agcagaaata tgtgtaagac tggacctcaa tatgttgtca gactcggaaa atccacagca  13800
tctggaactt catgagccac caaaagttgt ggataaggca aagtctccag gcgtggatcc  13860
caagcagctg gcggcagagc tgcagaaagt ctcactccag cagtccccac tggtcatgtc  13920
atcagttgtg gagaaagggg ctcatgctca ctcaggtccc acatcggcag gatccagttc  13980
tgttcccagc cccgggcagc cagggtcacc ttcagtaagc aaaaagaagc acggcggcag  14040
caagcctact gatgtgtcca agactgcctc tcacccaatt acaggagaga ttcagcttca  14100
aatcaactac gatcttggaa atcttataat acatattctt caagcaagaa acctggtccc  14160
cagagacaac aatggctact cggacccatt tgtgaaggtg tacctacttc caggacgagg  14220
tcaagtcatg gttgtccaga atgcaagtgt tgagtacaag agaaggacta aatatgtcca  14280
gaaaagtctt aatcccgagt ggaatcaaac agtaatttat aaaagtattt ccatggagca  14340
gctcatgaag aagaccttgg aggtgacagt ttgggattat gatagattct catccaacga  14400
cttccttgga gaggtattga ttgatttatc tagcacatct catctggaca acactcctcg  14460
gtggtatccg ctgaaagaac agactgaaag cattgagcat ggcaagtctc actccagtca  14520
aaacagccag cagtccccaa agccctctgt gatcaaaagc agaagccacg gtatcttccc  14580
cgacccatcc aaggatatgc aggttcccac cattgagaaa tcccacagta gtcctggtag  14640
ttcaaaatca tcatctgaag gccatctccg atctcatgga ccatctcgca gtcaaagcaa  14700
aaccagtgtc gcccagaccc acctggaaga tgcaggggcg gccatagccg cagctgaagc  14760
cgctgtgcag caactccgca ttcaaccaag taaaagacgc aaataaattc ctcagcatgg  14820
cagcttaatg ttcatctgtt gccttcctct cccgctgtct ttctccattt gctttctgtt  14880
```

-continued

```
ttttggcatc cctgctcact ctgttctgtc cttttgtctg tgtaagaaca gtatcaacat  14940

ataaatatgc tcttctttta gttcctcttg gttttttctg tttggttttt ttaatttaca  15000

taaactgcaa taaaactggc tgtttctcct ttgtttccac catccatcca acctggctca  15060

tagtatttgg tagccgtgtc cgtgaagttt gcaggcaaag cagtgttgtg tgtcttttgt  15120

gtgcacttcc ttctccttta aaacacagga attataagca caagggactg ccagttttct  15180

agcattatcc ccagtaaagc aaccatggac acacacacac acacacacac acacacacac  15240

acacacacac atttacatca ggttagcaat gagatacttg gacttggaaa cattcaacat  15300

ttgagcagat gcttagtgag accaacagtc aaatctagaa cctagggtga aaagccatct  15360

gaggcaatgt ttaaaaaaga atacgtgcaa aaaggagctt tccatgtgtt tctcctgaag  15420

aacatgtgca gagatttgta ttctcaaaac tacgtatttt tcctatgcat attcgctgat  15480

gttttaaggc aatgtaatct cagtgaggac cattgtctgg tccactctgt tagatcacac  15540

tttgtacaga agtttacaaa ttattatttt tttttatctg tggaatgttt tcagcgtcaa  15600

gaagtgcata tctagtagtt ttagtcaatt aaagtctagc cattgacttg tcttaatcga  15660

tgagttttca ttcatgaaat tttctgatat aattctataa aaacctggct acaggcacat  15720

tgtcaattcc aagaggcgtc ggccaggtca tggagatagt gtgtcatttt cttcatccct  15780

ctagtcctca ttcccaggaa acagccagtt ttaatcccct tcagtgctgt gcatgtggta  15840

tcattttggc atctgacaac acagtttaaa gagagcaaaa gcacacttct gtttgcatga  15900

ataacattta agctggttcc atctgaggat acactctggg tttccatttc acccacactg  15960

ccacagcagc acataaaagc ggtcagtgta atcatgccag gaagcagcac aggcacagca  16020

tagcaggcgt cctccccatt caaagaactc agtctgataa tctgcctcca ccagccaatg  16080

gcaaccaaga ccaaagccag ctagccctca ggaaggtgat gtccgatgga ccagtcaaac  16140

cagaaggagg tgagcagaaa ggccctgttc aaagcacaca gcaagaacgt gcccccaaat  16200

ttaaagctct catccctaat acttagagat tgtctaatga aatatgttta tccccttttt  16260

aatgtgcttt tgtgggcatg gcattttagg atttcatcat caccgtgtaa gtcccaagat  16320

cagtcccata ttatattgac tacagtgatt tgtatttttc tatgcaatgg gtgtcttttg  16380

acatttgttg aaaaatagtt taacggtatt cttattgcag aatggaatgc atgctactaa  16440

cctagtctgt ttaagcatga ctataaaata tgttgcattg tgataaaagt ttccattgct  16500

cacaattcaa gttagcatac ccattgaaat gtagatcagt ttttgttgac tattatttga  16560

catgtaacat ttggaaatgc ttagaggaga gcaaaggaaa aattgttaat gcactcattc  16620

accttggcac agaggaaatt ctctcctgag cctacaagca gacatcttct gtgcgtgtta  16680

ccgtagctgt taagtgtatc agctgtgttg ggcatgtgaa tatccaagtg cctgtgtaat  16740

aaataaagtt cttt                                                    16754
```

<210> SEQ ID NO 4
<211> LENGTH: 2342
<212> TYPE: DNA
<213> ORGANISM: Homo sapiens

<400> SEQUENCE: 4

```
gcgcagctgc tctacgccct gctggcggcg ctgtgcttcg ccgtgagccg ctcgctgctg     60

ctgacgtgcc tggtgccggc cgcgctgctg ggcctgcgct actactacag ccgcaaggtg    120

atccgcgcct acctggagtg cgcgctgcac acggacatgg cggacatcga gcagtactac    180
```

-continued atgaagccgc ccggctcctg cttctgggtg gccgtgctgg atggcaacgt ggtgggcatt 240
gtggctgcac gggcccacga ggaggacaac acggtggagc tgctgcggat gtctgtggac 300
tcacgtttcc gaggcaaggg catcgccaag gcgctgggcc ggaaggtgct ggagttcgcc 360
gtggtgcaca actactccgc ggtggtgctg ggcacgacgg ccgtcaaggt ggccgcccac 420
aagctctacg agtcgctggg cttcagacac atgggcgcca gtgaccacta cgtgctgccg 480
ggcatgaccc tctcgctggc tgagcgcctc ttcttccagg tccgctacca ccgctaccgc 540
ctgcagctgc gcgaggagtg accgccgccg ctcgcccgcc cgcccccccg gccgccctgt 600
ccgcctttgc ccgcctgccc gccgcccggc gcggcctgct ttcagacgct cacttggcgt 660
ttgtgttggg tttccccttt tcaacatcct gcggttgtct ggctggttcc ggggggtgcg 720
gggctgttgt tcttcggcga cactttggtg gggggtgggtt gtttgtcgcc atagcccctc 780
gcccttcccc acctgcctgg gcggcttgcc acctgaagag tggcatcttg gaccaccgcg 840
gctgtccatg acgctgccct gcccgccgcc actggggaag gcccagcctt gctcaccaag 900
cacagaacct ctgcagcaga tcccggggcc aggctccggc cccgcctgcg gccccagcgc 960
cactgcctgt ggaggcccga gctggccacg gcgctgcttt gctccgcgca tgccgagggt 1020
gtggcccggc tgagcatgcc gcatgcacac agccccgccc tgccgccctg cccagactgg 1080
acccggagac ccgggctggt gagcgcccct gtccccagcc cccagctggc tgtgggaggg 1140
cctgcccctg cccccacctc ctggagggcc tggtctgccc cgcgccgccc ggctctgtcc 1200
acacctgctt tgctctgacg ccctccattt ctctggctcc ggcccctccc ctgcctgggc 1260
tgtgctgact ggtgtcatca cccaggtgac tcccatggcg tccgtggcac agccagggtg 1320
ggggtccatg ggacccctct ccccagtgcc cactggatcg tgctggcctc tcccagatgt 1380
ccccggggac ctcctgcctc tggctgacgg tccaccctgt gaatcttatc agcccaggct 1440
gctgccaaca gcgcccagcc cacagcttct cccagcctga aaccaacaca ttttctaata 1500
agttatttag acagaatagc actctgcatg actttaattc ttgggacaaa acggtagttt 1560
gtaccctaag acacagtttc tggcccagtg tgatgggggt gggtggccgg gtgggtggag 1620
cgttttgctg ttggaaacct ggagggaaac cctgattgga tgtcatttcc tgccatggag 1680
cacgcctccc agccctggcc tgcagggtgg gcagggtggg gggcaaggga gtccgcagcc 1740
tccgggagga ggggcagggc gctgccttgg gctgggtggg aagaggggtg gccgcctcgg 1800
cttccgctgg ccatgctcct ggtctctcct tcctgaggtc acaggcaggg gctgccctgg 1860
acggggggcg gggggggtgg cctggaaggg gagacagagg tggagggtgg cacaggctgc 1920
acattcagct tagaagtgga cctggctttg gtggcaggag aagaataaac acttgcccag 1980
accccttttgt gtgggggaat tggggagggg tcgtggcagg cagggtgggc cacggaactg 2040
ggtcccaggc atcaaggcca cgtgcagggc catggaggga tgcttctcac gaggcgcttc 2100
agaagcgagc gaagggacag agaagccctg cgtccaaggg ccttttgtcc tgttagcaat 2160
tgaggtgtgc agagcactgt acagacccca ctcccctgta cattcctccc tggaggtgcc 2220
cggtccccgc ttggggatgg gagttttgta gactgtacag aaatcggcac cctattttct 2280
tgcagctcag attttgttaa tctggaatat acagacagac gtaaagtgtt ttagcaaaat 2340
gg 2342

<210> SEQ ID NO 5
<211> LENGTH: 2774
<212> TYPE: DNA
<213> ORGANISM: Homo sapiens -continued

<400> SEQUENCE: 5

```
tgcagaagac tttcagtcgt ttttgctgga atgattgagc ttacattttt tattctttcc     60
gcattcaaac ttagagacac tcacctctgg tattttgtaa tacctggctt ttccattttt    120
ggaattttct ggatgatttg tcatattatt tttcttttaa ctctttgggg attccatacc    180
aaattaaatg actgccataa agtatatttt actcccagga cagattacaa tagccttgat    240
agaatcatgg catccaaagg gatgcgccat ttttgcttga tttcagagca gttggtgttc    300
tttagtcttc ttgcaacagc gattttggga gcagtttcct ggcagccaac aaatggaatt    360
ttcttgagca tgtttctaat cgttttgcca ttggaatcca tggctcatgg gctcttccat    420
gaattgggta actgtttagg aggaacatct gttggatatg ctattgtgat tcccaccaac    480
ttctgcagtc ctgatggtca gccaacactg cttcccccag aacatgtaca ggagttaaat    540
ttgaggtcta ctggcatgct caatgctatc caaagatttt ttgcatatca tatgattgag    600
acctatggat gtgactattc cacaagtgga ctgtcatttg atactctgca ttccaaacta    660
aaagctttcc tcgaacttcg gacagtggat ggacccagac atgatacgta tattttgtat    720
tacagtgggc acacccatgg tacaggagag tgggctctag caggtggaga tacactacgc    780
cttgacacac ttatagaatg gtggagagaa aagaatggtt ccttttgttc ccggcttatt    840
atcgtattag acagcgaaaa ttcaacccct tgggtgaaag aagtgaggaa aattaatgac    900
cagtatattg cggtgcaagg agcagagttg ataaaagcag tagatattga agaagctgac    960
ccgccacagc taggtgactt tacaaaagac tgggtagaat ataactgcaa ctccagtaat   1020
aacatctgct ggactgaaaa gggacgcaca gtgaaagcag tatatggtgt gtcaaaacgg   1080
tggagtgact acactctgca tttgccaacg ggaagcgatg tggccaagca ctggatgtta   1140
cactttcctc gtattacata tcccctagtg catttggcaa attggttatg cggtctgaac   1200
ctttttgga tctgcaaaac ttgttttagg tgcttgaaaa gattaaaaat gagttggttt    1260
cttcctactg tgctggacac aggacaaggc ttcaaacttg tcaaatctta atttggaccc   1320
caaagcggga tattaataag cactcatact accaattatc actaacttgc catttttgt    1380
atgctgtatt tttatttgtg gaaaatacct tgctacttct gtagctgctc tcactttgtc   1440
ttttcttaag taattatggt atatataagg cgttgggaaa aaacatttta taatgaaagt   1500
atgtagggag tcaaatgctt actgtaaatg cataagagac gttaaaaata acactgcact   1560
ttcaggaatg tttgcttatg gtcctgatta gaaagaaaca gttgtctatg ctctgcaatg   1620
gtcaatgatg aattactaat gccttatttt ctaggcatat aataatagtt tagagaatgt   1680
agaccagata aatttgttta ctgttttaag aaaactacca gtttacttac agaagattct   1740
tttttccaaa cagtaggttt catccaagac catttgaaga gctgcaaact ctttctctta   1800
gaaaagaaag agggcagcct aaaataaacg caaaatttgc ttatactcca tcacattcag   1860
atgtcttggt tgtgacttat taccagtgtg gcagagaacc caagttacat tttagatcaa   1920
aatattcttt atgtaggtat tgttaaaagg ctagagccta caagttgctc ttccatgcgt   1980
tggtcagggg gccctgaaaa cactggtaat attaagagtc tttctcaggg taacttaatg   2040
ttttcttaat gaacagtgtt tccagctaca aattcttcca ataaattgtc ttcctttttg   2100
aaaagtactc tcatagaaga aatttagcaa tttctcgttg actgactcag tctattttaa   2160
gtattcagaa aagattttga tccccattga gttaatgctc tgccttgaaa attatttttc   2220
tgatccttgt tagtgataac atttttttc tactgaaggt cagaggatag gaaacaagta    2280
```

-continued

```
tttctcttct ggtatacatg taatgtattc tgtaaaaaag tattcatatt ggcaatttta   2340

gttaggcata atattgtggt tgtaattttt aaaacttagt gttttgtctg attaaagcag   2400

gcactgatca gggtatctcc taagaggtaa ttcacttctt attcctttcc aataattatt   2460

acattctaaa ttttcatcta tgagaaataa caaacaagaa gggaatagaa ttaaattggg   2520

gtataatcta atcttcattg tttaaatggt ttgccttctc accattgaag ccattttttt   2580

atagcctcag aaagaggaaa taatgcctcc accattttct acctggtgac ttgaaaattg   2640

aacttttaag ttaggaagaa gttagagtca gggaacttgt ataccactat ctatgcagca   2700

ttgttatagt ctgattattt ctgtgttttg aatatgattt tcctaatgct ctaaataaaa   2760

ttttgttaaa aatt                                                       2774
```

<210> SEQ ID NO 6
<211> LENGTH: 3252
<212> TYPE: DNA
<213> ORGANISM: Homo sapiens

<400> SEQUENCE: 6

```
ccacagatcg gagctatgtg agtaggagaa ggagaactaa aaagagtgtg gatacaagcg     60

tccaaactga tgatgaagat caggatgagt gggatatgcc tactagatca aggaggaaag    120

ctcgtgtagg gaaatatggt gacagcatga cagaggctga caagaccaaa cccctttcca    180

aagtctccag catagcagtt caaacggtag cagagatatc tgtgcaaact gaaccagttg    240

gaaccataag aacaccctcc atacgggcac gagtggatgc caaggtagaa ataattaaac    300

acatttcagc acctgaaaag acttacaaag gggcagttt aggatgtcaa acagaagcag     360

attcagacac acaaagtcct caatatctga gtgccacatc tccacccaaa gacaagaaac    420

gcccaacacc tttagagatt ggttattcat ctcacctccg ggcagattcc acagtacagc    480

tggctccttc cccacccaaa tcccccaaag tcctttactc acccatctca ccactttcac    540

caggcaaagc cttagaatca gcctttgtac cttatgaaaa acccctccct gatgatataa    600

gtccacagaa agtactgcat ccagatatgg ctaaagttcc cccagcaagt cctaagacag    660

ccaagatgat gcagcgttct atgtctgacc ccaagcctct gagtccaaca gcagacgaaa    720

gttccagggc tccttttcag tataccgagg gctatacgac taaaggttct caaaccatga    780

catcctctgg agcccagaaa aaagttaaaa gaactctgcc aaatccacct cctgaggaga    840

tttccacagg aactcaatcc acattcagca caatgggcac agtttccagg agaaggatct    900

gcagaaccaa cacaatggca cgagccaaga ttctccagga catagacaga gagcttgatc    960

ttgtggaaag ggagtctgca aaacttcgaa agaaacaagc agagcttgat gaagaagaaa   1020

aggagattga tgctaagcta cgatacctgg aaatgggaat taacaggagg aaagaggccc   1080

tattaaagga gagagaaaag agagaacgag cctacctcca gggagtagct gaggatcgtg   1140

attacatgtc tgacagtgaa gtgagtagca caagaccaac ccgaatagaa agtcagcatg   1200

gcattgagcg accaagaact gctccccaaa ctgaattcag ccagtttata ccaccacaaa   1260

cccaaacaga atctcaacta gttcctccga caagtcctta cacacaatac cagtactctt   1320

cccctgctct tcctacccaa gcacccacct catacactca acagtctcat tttgagcaac   1380

aaactttgta ccatcagcaa gtttcacctt atcagactca gccaacattc caagctgtgg   1440

caacaatgtc cttcacacct caagttcaac ctacaccaac cccacagcct tcttatcagt   1500

taccttcaca gatgatggtg atacaacaga agccacggca aactacatta tatttggagc   1560

ccaagataac ctcaaactat gaagtgattc gcaaccaacc ccttatgata gcacctgttt   1620
```

-continued

```
ctacggataa cacatttgct gtttcccatc ttggtagtaa gtacaatagt ttagacttga   1680

gaataggttt ggaggaaaga agtagcatgg caagcagtcc aatatcaagc atatctgcag   1740

attctttcta tgcagatatt gatcaccata ctccacgaaa ttatgtccta attgacgaca   1800

ttggagagat caccaaagga acagcggcat taagcaccgc atttagcctt catgaaaagg   1860

atctgtcaaa aacagaccgt ctccttcgaa ccactgagac acgccggtct caagaagtga   1920

cagatttcct agcaccttta cagtcttcct ctagattgca tagttatgtg aaggcggagg   1980

aagacccaat ggaggatcct tacgagttaa agcttctgaa acatcagatt aaacaggaat   2040

ttcgtagagg gacagagagc ttagatcacc ttgctggtct ttctcattat taccatgctg   2100

atactagcta cagacatttt ccaaaatctg agaagtatag catcagtaga ctcacacttg   2160

aaaaacaagc agcaaaacaa ctgccagcag ccatacttta tcaaaagcag tcaaagcata   2220

agaaatcact aattgaccct aaaatgtcaa aattttcacc tattcaagaa agtagagacc   2280

ttgaacctga ttattcaagc tatatgactt ctagcacttc atctattggt ggcatttcct   2340

ccagggcaag gctccttcaa gatgacatca cttttggcct cagaaaaaat attacagacc   2400

aacaaaaatt tatgggatct tctcttggca caggactggg cacattagga aataccatac   2460

gctcagctct gcaggatgaa gcggataagc catacagtag tggcagcagg tccagacctt   2520

cctccagacc ttcctctgtc tatgggcttg atttatcaat taaaagggat tcttctagct   2580

cttccctaag actgaaagct caagaggctg aagctctaga tgtttccttt agtcatgcat   2640

catcctctgc cagaactaag ccgaccagtt tgccaattag tcaaagtaga ggaagaatac   2700

caattgtggc ccagaattct gaagaagaaa gcccactcag tcctgttggc cagccaatgg   2760

gaatggccag ggctgcagct ggacccctgc caccaatatc tgcagacacc agggatcagt   2820

ttggatcaag ccactcattg cctgaagttc agcaacacat gagggaagaa tcacggactc   2880

gaggctatga ccgtgacata gcattcatca tggatgactt ccaacatgcc atgtcagaca   2940

gtgaaggtaa attgggcctc aaactaccct gttactctca aaactcaaac tcttattttt   3000

ctgcatgttt aatttccctt ctccagagat gtatcctact tttcttggtg tgtcttttgc   3060

atgtttactt caattttatt tcttgtaaat ggaaatttta tcatgtgtat agattctgta   3120

gcatgctttt ctttatttag ttttacttta ttcctttatt gttctgtttc ttgattgttt   3180

gcttgatttg tttggtgtct gcttttctaa aaccattatc aaataattct gtcaataaaa   3240

tatggtcatc ct                                                        3252
```

```
<210> SEQ ID NO 7
<211> LENGTH: 134
<212> TYPE: PRT
<213> ORGANISM: Mus musculus

<400> SEQUENCE: 7

Met Ala Asp Ile Glu Gln Tyr Tyr Met Lys Pro Pro Gly Ser Cys Phe
1               5                   10                  15

Trp Val Ala Val Leu Asp Gly Asn Val Val Gly Ile Val Ala Ala Arg
            20                  25                  30

Ala His Glu Glu Asp Asn Thr Val Glu Leu Leu Arg Met Ser Val Asp
        35                  40                  45

Ser Arg Phe Arg Gly Lys Gly Ile Ala Lys Ala Leu Gly Arg Arg Val
    50                  55                  60

Leu Glu Phe Ala Met Leu His Asn Tyr Ser Ala Val Val Leu Gly Thr
65                  70                  75                  80
```

-continued

Thr Ala Val Lys Val Ala Ala His Lys Leu Tyr Glu Ser Leu Gly Phe
85 90 95

Arg His Met Gly Ala Ser Asp His Tyr Val Leu Pro Gly Met Thr Leu
100 105 110

Ser Leu Ala Glu Arg Leu Phe Phe Gln Val Arg Tyr His Arg Tyr Arg
115 120 125

Leu Gln Leu Arg Glu Glu
130

<210> SEQ ID NO 8
<211> LENGTH: 697
<212> TYPE: PRT
<213> ORGANISM: Mus musculus

<400> SEQUENCE: 8

Met Cys Arg Ser Leu Arg Tyr Cys Val Ser His Cys Leu Tyr Leu Ala
1 5 10 15

Met Thr Arg Leu Glu Glu Val Asn Arg Glu Val Asn Met His Ser Ser
20 25 30

Val Arg Tyr Leu Gly Tyr Leu Ala Arg Ile Asn Leu Leu Val Ala Ile
35 40 45

Cys Leu Gly Leu Tyr Val Arg Trp Glu Lys Thr Ala Asn Ser Leu Ile
50 55 60

Leu Val Ile Phe Ile Leu Gly Leu Phe Val Leu Gly Ile Ala Ser Ile
65 70 75 80

Leu Tyr Tyr Tyr Phe Ser Met Glu Ala Ala Ser Leu Ser Leu Ser Asn
85 90 95

Leu Trp Phe Gly Phe Leu Leu Gly Leu Leu Cys Phe Leu Asp Asn Ser
100 105 110

Ser Phe Lys Ser Asp Val Lys Glu Glu Thr Thr Lys Tyr Leu Leu Leu
115 120 125

Thr Ser Ile Val Leu Arg Ile Leu Cys Ala Leu Val Glu Arg Ile Ser
130 135 140

Gly Tyr Val Arg His Arg Pro Thr Leu Leu Thr Thr Val Glu Phe Leu
145 150 155 160

Glu Leu Val Gly Phe Ala Ile Ala Ser Thr Thr Met Leu Val Glu Lys
165 170 175

Ser Leu Ser Val Ile Leu Leu Val Met Ala Leu Ala Met Leu Ile Ile
180 185 190

Asp Leu Arg Met Lys Ser Phe Leu Ala Ile Pro Asn Leu Ile Ile Phe
195 200 205

Ser Val Leu Leu Phe Phe Ser Ser Leu Glu Thr Pro Gln Asn Pro Ile
210 215 220

Ala Phe Ala Cys Phe Phe Ile Cys Leu Val Thr Asp Pro Phe Leu Asp
225 230 235 240

Ile Tyr Phe Ser Gly Leu Ser Val Thr Glu Arg Trp Lys Pro Phe Leu
245 250 255

His Arg Gly Arg Ile Cys Arg Arg Leu Ser Val Leu Phe Thr Ala Met
260 265 270

Ile Glu Leu Thr Phe Phe Ile Leu Ser Ala Phe Lys Leu Arg Asp Thr
275 280 285

His Leu Trp Tyr Phe Val Ile Pro Gly Phe Ser Ile Phe Gly Phe Phe
290 295 300

Trp Met Ile Cys His Ile Ile Phe Leu Leu Thr Leu Trp Gly Phe His

-continued

```
305                 310                 315                 320

Thr Lys Leu Asn Asp Cys His Lys Val Tyr Ile Asn His Arg Ala Asp
                325                 330                 335

Asn Asn Ser Leu Asp Arg Ile Met Ala Ser Lys Gly Met Arg His Phe
            340                 345                 350

Cys Leu Ile Ser Glu Gln Leu Val Phe Phe Ser Leu Leu Ala Thr Ala
        355                 360                 365

Ile Leu Gly Ala Val Ser Trp Gln Pro Thr Asn Gly Ile Phe Leu Ser
    370                 375                 380

Met Phe Leu Ile Val Leu Pro Leu Glu Ser Met Ala His Gly Leu Phe
385                 390                 395                 400

His Glu Leu Gly Asn Cys Leu Gly Gly Thr Ser Val Gly Tyr Ala Ile
                405                 410                 415

Val Ile Pro Thr Asn Phe Cys Ser Pro Asp Gly Gln Pro Thr Leu Leu
            420                 425                 430

Pro Pro Glu His Val Gln Glu Leu Asn Leu Arg Ser Thr Gly Met Leu
        435                 440                 445

Asn Ala Ile Gln Arg Phe Phe Ala Tyr His Met Ile Glu Thr Tyr Gly
    450                 455                 460

Cys Asp Tyr Ser Thr Ser Gly Leu Ser Phe Asp Thr Leu His Ser Lys
465                 470                 475                 480

Leu Lys Ala Phe Leu Glu Leu Arg Thr Val Asp Gly Pro Arg His Asp
                485                 490                 495

Thr Tyr Val Leu Tyr Tyr Ser Gly His Thr His Gly Ser Gly Glu Trp
            500                 505                 510

Ala Leu Ala Gly Gly Asp Ile Leu Arg Leu Asp Thr Leu Leu Glu Trp
        515                 520                 525

Trp Arg Glu Lys Asn Gly Ser Phe Cys Ser Arg Leu Ile Ile Ile Leu
    530                 535                 540

Asp Ser Glu Asn Ser Thr Pro Trp Val Lys Glu Val Arg Lys Ile Asn
545                 550                 555                 560

Asp Gln Tyr Val Ala Val Gln Gly Ala Glu Leu Ala Lys Thr Val Asp
                565                 570                 575

Ile Glu Glu Ala Asp Pro Pro Gln Leu Gly Asp Phe Thr Arg Asp Trp
            580                 585                 590

Val Glu Tyr Asn Cys Asn Ser Thr Asn Asn Ile Cys Trp Thr Glu Lys
        595                 600                 605

Gly Arg Thr Val Arg Ala Val Tyr Gly Val Ser Lys Arg Trp Ser Asp
    610                 615                 620

Tyr Thr Leu His Leu Pro Thr Gly Ser Asp Val Ala Lys His Trp Met
625                 630                 635                 640

Leu His Phe Pro Arg Val Thr Tyr Pro Leu Val His Leu Ala Asn Trp
                645                 650                 655

Leu Cys Gly Leu Asn Leu Phe Trp Val Cys Lys Ala Cys Phe Arg Cys
            660                 665                 670

Leu Lys Arg Leu Lys Met Ser Trp Phe Leu Pro Thr Val Leu Asp Thr
        675                 680                 685

Gly Gln Gly Phe Lys Leu Val Lys Ser
    690                 695


<210> SEQ ID NO 9
<211> LENGTH: 4833
<212> TYPE: PRT
<213> ORGANISM: Mus musculus
```

-continued

<400> SEQUENCE: 9

```
Met Gly Asn Glu Ala Ser Leu Glu Gly Glu Gly Leu Pro Glu Gly Leu
1               5                   10                  15

Ala Ala Ala Ala Gly Gly Ala Gly Gly Ser Gly Ser Ala Leu His Pro
            20                  25                  30

Gly Ile Pro Ala Gly Met Glu Ala Asp Leu Ser Gln Leu Ser Glu Glu
        35                  40                  45

Glu Arg Arg Gln Ile Ala Ala Val Met Ser Arg Ala Gln Gly Leu Pro
    50                  55                  60

Lys Gly Ser Val Pro Ala Ala Ala Ala Glu Ser Pro Ser Met His Arg
65                  70                  75                  80

Lys Gln Glu Leu Asp Ser Ser Gln Ala Pro Gln Gln Pro Gly Lys Pro
                85                  90                  95

Pro Asp Pro Gly Arg Pro Pro Gln His Gly Leu Ser Lys Ser Arg Thr
            100                 105                 110

Thr Asp Thr Phe Arg Ser Glu Gln Lys Leu Pro Gly Arg Ser Pro Ser
        115                 120                 125

Thr Ile Ser Leu Lys Glu Ser Lys Ser Arg Thr Asp Phe Lys Glu Glu
    130                 135                 140

Tyr Lys Ser Ser Met Met Pro Gly Phe Phe Ser Glu Val Asn Pro Leu
145                 150                 155                 160

Ser Ala Val Ser Ser Val Val Asn Lys Phe Asn Pro Phe Asp Leu Ile
                165                 170                 175

Ser Asp Ser Glu Ala Val Gln Glu Glu Thr Thr Lys Lys Gln Lys Val
            180                 185                 190

Ala Gln Lys Asp Gln Gly Lys Ser Glu Gly Ile Thr Lys Pro Ser Leu
        195                 200                 205

Gln Gln Pro Ser Pro Lys Leu Ile Pro Lys Gln Gln Gly Pro Gly Lys
    210                 215                 220

Glu Val Ile Pro Gln Asp Ile Pro Ser Lys Ser Val Ser Ser Gln Gln
225                 230                 235                 240

Ala Glu Lys Thr Lys Pro Gln Ala Pro Gly Thr Ala Lys Pro Ser Gln
                245                 250                 255

Gln Ser Pro Ala Gln Thr Pro Ala Gln Gln Ala Lys Pro Val Ala Gln
            260                 265                 270

Gln Pro Gly Pro Ala Lys Ala Thr Val Gln Gln Pro Gly Pro Ala Lys
        275                 280                 285

Ser Pro Ala Gln Pro Ala Gly Thr Gly Lys Ser Pro Ala Gln Pro Pro
    290                 295                 300

Val Thr Ala Lys Pro Pro Ala Gln Gln Ala Gly Leu Glu Lys Thr Ser
305                 310                 315                 320

Leu Gln Gln Pro Gly Pro Lys Ser Leu Ala Gln Thr Pro Gly Gln Gly
                325                 330                 335

Lys Val Pro Pro Gly Pro Ala Lys Ser Pro Ala Gln Gln Pro Gly Thr
            340                 345                 350

Ala Lys Leu Pro Ala Gln Gln Pro Gly Pro Gln Thr Ala Ser Lys Val
        355                 360                 365

Pro Gly Pro Thr Lys Thr Pro Ala Gln Leu Ser Gly Pro Gly Lys Thr
    370                 375                 380

Pro Ala Gln Gln Pro Gly Pro Thr Lys Pro Ser Pro Gln Gln Pro Ile
385                 390                 395                 400

Pro Ala Lys Pro Gln Pro Gln Gln Pro Val Ala Thr Lys Pro Gln Pro
```

-continued

```
            405                 410                 415

Gln Gln Pro Ala Pro Ala Lys Pro Gln Pro Gln His Pro Thr Pro Ala
        420                 425                 430

Lys Pro Gln Pro Gln Gln Pro Thr Pro Ala Lys Pro Gln Pro Gln Gln
    435                 440                 445

Pro Thr Pro Ala Lys Pro Gln Pro Gln His Pro Gly Leu Gly Lys Pro
    450                 455                 460

Ser Ala Gln Gln Pro Ser Lys Ser Ile Ser Gln Thr Val Thr Gly Arg
465                 470                 475                 480

Pro Leu Gln Ala Pro Pro Thr Ser Ala Ala Gln Ala Pro Ala Gln Gly
                485                 490                 495

Leu Ser Lys Thr Ile Cys Pro Leu Cys Asn Thr Thr Glu Leu Leu Leu
            500                 505                 510

His Thr Pro Glu Lys Ala Asn Phe Asn Thr Cys Thr Glu Cys Gln Ser
        515                 520                 525

Thr Val Cys Ser Leu Cys Gly Phe Asn Pro Asn Pro His Leu Thr Glu
    530                 535                 540

Ile Lys Glu Trp Leu Cys Leu Asn Cys Gln Met Gln Arg Ala Leu Gly
545                 550                 555                 560

Gly Glu Leu Ala Ala Ile Pro Ser Ser Pro Gln Pro Thr Pro Lys Ala
                565                 570                 575

Ala Ser Val Gln Pro Ala Thr Ala Ser Lys Ser Pro Val Pro Ser Gln
            580                 585                 590

Gln Ala Ser Pro Lys Lys Glu Leu Pro Ser Lys Gln Asp Ser Pro Lys
        595                 600                 605

Ala Pro Glu Ser Lys Lys Pro Pro Pro Leu Val Lys Gln Pro Thr Leu
    610                 615                 620

His Gly Pro Thr Pro Ala Thr Ala Pro Gln Pro Pro Val Ala Glu Ala
625                 630                 635                 640

Leu Pro Lys Pro Ala Pro Pro Lys Lys Pro Ser Ala Ala Leu Pro Glu
                645                 650                 655

Gln Ala Lys Ala Pro Val Ala Asp Val Glu Pro Lys Gln Pro Lys Thr
            660                 665                 670

Thr Glu Thr Leu Thr Asp Ser Pro Ser Ser Ala Ala Ala Thr Ser Lys
        675                 680                 685

Pro Ala Ile Leu Ser Ser Gln Val Gln Ala Gln Ala Gln Val Thr Thr
    690                 695                 700

Ala Pro Pro Leu Lys Thr Asp Ser Ala Lys Thr Ser Gln Ser Phe Pro
705                 710                 715                 720

Pro Thr Gly Asp Thr Ile Thr Pro Leu Asp Ser Lys Ala Met Pro Arg
                725                 730                 735

Pro Ala Ser Asp Ser Lys Ile Val Ser His Pro Gly Pro Thr Ser Glu
            740                 745                 750

Ser Lys Asp Pro Val Gln Lys Lys Glu Glu Pro Lys Lys Ala Gln Thr
        755                 760                 765

Lys Val Thr Pro Lys Pro Asp Thr Lys Pro Val Pro Lys Gly Ser Pro
    770                 775                 780

Thr Pro Ser Gly Thr Arg Pro Thr Thr Gly Gln Ala Thr Pro Gln Ser
785                 790                 795                 800

Gln Gln Pro Pro Lys Pro Pro Glu Gln Ser Arg Arg Phe Ser Leu Asn
                805                 810                 815

Leu Gly Gly Ile Ala Asp Ala Pro Lys Ser Gln Pro Thr Thr Pro Gln
            820                 825                 830
```

-continued

```
Glu Thr Val Thr Gly Lys Leu Phe Gly Phe Gly Ala Ser Ile Phe Ser
        835                 840                 845

Gln Ala Ser Asn Leu Ile Ser Thr Ala Gly Gln Gln Ala Pro His Pro
    850                 855                 860

Gln Thr Gly Pro Ala Ala Pro Ser Lys Gln Ala Pro Pro Pro Ser Gln
865                 870                 875                 880

Thr Leu Ala Ala Gln Gly Pro Pro Lys Ser Thr Gly Gln His Pro Ser
                885                 890                 895

Ala Pro Ala Lys Thr Thr Ala Val Lys Lys Glu Thr Lys Gly Pro Ala
            900                 905                 910

Ala Glu Asn Leu Glu Ala Lys Pro Ala Gln Ala Pro Thr Val Lys Lys
        915                 920                 925

Ala Glu Lys Asp Lys Lys His Pro Pro Gly Lys Val Ser Lys Pro Pro
    930                 935                 940

Pro Thr Glu Pro Glu Lys Ala Val Leu Ala Gln Lys Pro Asp Lys Thr
945                 950                 955                 960

Thr Lys Pro Lys Pro Ala Cys Pro Leu Cys Arg Thr Glu Leu Asn Val
                965                 970                 975

Gly Ser Gln Asp Pro Pro Asn Phe Asn Thr Cys Thr Glu Cys Lys Asn
            980                 985                 990

Gln Val Cys Asn Leu Cys Gly Phe  Asn Pro Thr Pro His  Leu Thr Glu
        995                 1000                 1005

Ile Gln  Glu Trp Leu Cys Leu  Asn Cys Gln Thr Gln  Arg Ala Ile
    1010                 1015                 1020

Ser Gly  Gln Leu Gly Asp Met  Asp Lys Met Pro Pro  Ala Ser Ser
    1025                 1030                 1035

Gly Pro  Lys Ala Ser Pro Val  Pro Ala Pro Ala Glu  Pro Pro Pro
    1040                 1045                 1050

Gln Lys  Thr Pro Thr Ala Ala  His Ala Lys Gly Lys  Lys Lys Glu
    1055                 1060                 1065

Thr Glu  Val Lys Ala Glu Thr  Glu Lys Gln Ile Pro  Glu Lys Glu
    1070                 1075                 1080

Thr Pro  Ser Ile Glu Lys Thr  Pro Pro Ala Val Ala  Thr Asp Gln
    1085                 1090                 1095

Lys Leu  Glu Glu Ser Glu Val  Thr Lys Ser Leu Val  Ser Val Leu
    1100                 1105                 1110

Pro Glu  Lys Lys Pro Ser Glu  Glu Glu Lys Ala Leu  Pro Ala Asp
    1115                 1120                 1125

Lys Lys  Glu Lys Lys Pro Pro  Ala Ala Glu Ala Pro  Pro Leu Glu
    1130                 1135                 1140

Glu Lys  Lys Pro Ile Pro Asp  Asp Gln Lys Leu Pro  Pro Asp Ala
    1145                 1150                 1155

Lys Pro  Ser Ala Ser Glu Gly  Glu Glu Lys Arg Asp  Leu Leu Lys
    1160                 1165                 1170

Ala His  Val Gln Ile Pro Glu  Glu Gly Pro Ile Gly  Lys Val Ala
    1175                 1180                 1185

Ser Leu  Ala Cys Glu Gly Glu  Gln Gln Pro Asp Thr  Arg Pro Glu
    1190                 1195                 1200

Asp Leu  Pro Gly Ala Thr Pro  Gln Thr Leu Pro Lys  Asp Arg Gln
    1205                 1210                 1215

Lys Glu  Ser Arg Asp Val Thr  Gln Pro Gln Ala Glu  Gly Thr Ala
    1220                 1225                 1230
```

-continued

```
Lys Glu  Gly Arg Gly Glu Pro  Ser Lys Asp Arg Thr  Glu Lys Glu
    1235                 1240                 1245

Glu Asp  Lys Ser Asp Thr Ser  Ser Ser Gln Gln Pro  Lys Ser Pro
    1250                 1255                 1260

Gln Gly  Leu Ser Asp Thr Gly  Tyr Ser Ser Asp Gly  Ile Ser Gly
    1265                 1270                 1275

Ser Leu  Gly Glu Ile Pro Ser  Leu Ile Pro Ser Asp  Glu Lys Asp
    1280                 1285                 1290

Leu Leu  Lys Gly Leu Lys Lys  Asp Ser Phe Ser Gln  Glu Ser Ser
    1295                 1300                 1305

Pro Ser  Ser Pro Ser Asp Leu  Ala Lys Leu Glu Ser  Thr Val Leu
    1310                 1315                 1320

Ser Ile  Leu Glu Ala Gln Ala  Ser Thr Leu Val Gly  Glu Lys Ala
    1325                 1330                 1335

Glu Lys  Lys Thr Gln Pro Gln  Lys Val Ser Pro Glu  Gln Pro Gln
    1340                 1345                 1350

Asp Gln  Gln Lys Thr Gln Thr  Pro Ser Glu Thr Arg  Asp Ile Ser
    1355                 1360                 1365

Ile Ser  Glu Glu Glu Ile Lys  Glu Ser Gln Glu Lys  Lys Val Thr
    1370                 1375                 1380

Ser Lys  Lys Asp Ser Ala Gln  Gly Phe Pro Ser Arg  Lys Glu His
    1385                 1390                 1395

Lys Glu  Asn Pro Glu Leu Val  Asp Asp Leu Ser Pro  Arg Arg Ala
    1400                 1405                 1410

Ser Tyr  Asp Ser Val Glu Asp  Ser Ser Glu Ser Glu  Asn Ser Pro
    1415                 1420                 1425

Val Ala  Arg Arg Lys Arg Arg  Thr Ser Ile Gly Ser  Ser Ser Ser
    1430                 1435                 1440

Glu Glu  Tyr Lys Gln Glu Asp  Ser Gln Gly Ser Gly  Glu Asp Glu
    1445                 1450                 1455

Asp Phe  Ile Arg Lys Gln Ile  Ile Glu Met Ser Ala  Asp Glu Asp
    1460                 1465                 1470

Ala Ser  Gly Ser Glu Asp Glu  Glu Phe Ile Arg Ser  Gln Leu Lys
    1475                 1480                 1485

Glu Ile  Gly Gly Val Thr Glu  Ser Gln Lys Arg Glu  Glu Thr Lys
    1490                 1495                 1500

Gly Lys  Gly Lys Ser Pro Ala  Gly Lys His Arg Arg  Leu Thr Arg
    1505                 1510                 1515

Lys Ser  Ser Thr Ser Phe Asp  Asp Asp Ala Gly Arg  Arg His Ser
    1520                 1525                 1530

Trp His  Asp Glu Asp Asp Glu  Thr Phe Asp Glu Ser  Pro Glu Leu
    1535                 1540                 1545

Lys Phe  Arg Glu Thr Lys Ser  Gln Glu Ser Glu Glu  Leu Val Val
    1550                 1555                 1560

Ala Gly  Gly Gly Gly Leu Arg  Arg Phe Lys Thr Ile  Glu Leu Asn
    1565                 1570                 1575

Ser Thr  Val Thr Asp Lys Tyr  Ser Ala Glu Ser Ser  Gln Lys Lys
    1580                 1585                 1590

Thr Thr  Leu Tyr Phe Asp Glu  Glu Pro Glu Leu Glu  Met Glu Ser
    1595                 1600                 1605

Leu Thr  Asp Ser Pro Glu Asp  Arg Ser Arg Gly Glu  Gly Ser Ser
    1610                 1615                 1620

Ser Leu  His Ala Ser Ser Phe  Thr Pro Gly Thr Ser  Pro Thr Ser
```

-continued

```
    1625                1630                1635

Val Ser  Ser Leu Asp Glu Asp  Ser Asp Ser Ser Pro  Ser His Lys
    1640                1645                1650

Lys Gly  Glu Ser Lys Gln Gln  Arg Lys Ala Arg His  Arg Ser His
    1655                1660                1665

Gly Pro  Leu Leu Pro Thr Ile  Glu Asp Ser Ser Glu  Glu Glu Glu
    1670                1675                1680

Leu Arg  Glu Glu Glu Glu Leu  Leu Lys Glu Gln Glu  Lys Gln Arg
    1685                1690                1695

Glu Leu  Glu Gln Gln Gln Arg  Lys Ser Ser Ser Lys  Lys Ser Lys
    1700                1705                1710

Lys Asp  Lys Asp Glu Leu Arg  Ala Gln Arg Arg Arg  Glu Arg Pro
    1715                1720                1725

Lys Thr  Pro Pro Ser Asn Leu  Ser Pro Ile Glu Asp  Ala Ser Pro
    1730                1735                1740

Thr Glu  Glu Leu Arg Gln Ala  Ala Glu Met Glu Glu  Leu His Arg
    1745                1750                1755

Ser Ser  Cys Ser Glu Tyr Ser  Pro Ser Ile Glu Ser  Asp Pro Glu
    1760                1765                1770

Gly Phe  Glu Ile Ser Pro Glu  Lys Ile Ile Glu Val  Gln Lys Val
    1775                1780                1785

Tyr Lys  Leu Pro Thr Ala Val  Ser Leu Tyr Ser Pro  Thr Asp Glu
    1790                1795                1800

Gln Ser  Val Met Gln Lys Glu  Gly Ala Gln Lys Ala  Leu Lys Ser
    1805                1810                1815

Ala Glu  Glu Met Tyr Glu Glu  Met Met His Lys Pro  His Lys Tyr
    1820                1825                1830

Lys Ala  Phe Pro Ala Ala Asn  Glu Arg Asp Glu Val  Phe Glu Lys
    1835                1840                1845

Glu Pro  Leu Tyr Gly Gly Met  Leu Ile Glu Asp Tyr  Ile Tyr Glu
    1850                1855                1860

Ser Leu  Val Glu Asp Thr Tyr  Asn Gly Ser Val Asp  Gly Ser Leu
    1865                1870                1875

Leu Thr  Arg Gln Asp Glu Gln  Asn Gly Phe Met Pro  Gln Arg Gly
    1880                1885                1890

Arg Glu  Gln Lys Ile Arg Leu  Arg Glu Gln Ile Tyr  Asp Asp Pro
    1895                1900                1905

Met Gln  Lys Ile Thr Asp Leu  Gln Lys Glu Phe Tyr  Glu Leu Glu
    1910                1915                1920

Ser Leu  His Ser Ile Val Pro  Gln Glu Asp Ile Val  Ser Ser Ser
    1925                1930                1935

Tyr Ile  Ile Pro Glu Ser His  Glu Ile Val Asp Leu  Gly Ser Met
    1940                1945                1950

Val Thr  Ser Thr Ser Glu Glu  Lys Lys Leu Leu Asp  Ala Asp Ala
    1955                1960                1965

Ala Tyr  Glu Glu Leu Met Lys  Arg Gln Gln Met Gln  Val Thr Asp
    1970                1975                1980

Gly Ser  Ser Leu Ile Gln Thr  Thr Met Gly Asp Asp  Met Ala Glu
    1985                1990                1995

Ser Thr  Leu Asp Phe Asp Arg  Val Gln Asp Ala Ser  Leu Thr Ser
    2000                2005                2010

Ser Ile  Leu Ser Gly Ala Ser  Leu Thr Asp Ser Thr  Ser Ser Ala
    2015                2020                2025
```

-continued

```
Thr Leu  Ser Ile Pro Asp Val  Lys Ile Thr Gln His  Phe Ser Thr
    2030                 2035                 2040

Glu Glu  Phe Glu Asp Glu Tyr  Val Thr Asp Tyr Thr  Arg Glu Ile
    2045                 2050                 2055

Gln Glu  Ile Ile Ala His Glu  Ser Leu Ile Leu Thr  Tyr Ser Glu
    2060                 2065                 2070

Pro Ser  Glu Ser Ala Thr Ser  Val Pro Pro Ser Asp  Thr Pro Ser
    2075                 2080                 2085

Leu Thr  Ser Ser Ile Ser Ser  Val Cys Thr Thr Asp  Ser Ser Ser
    2090                 2095                 2100

Pro Val  Thr Thr Leu Asp Ser  Leu Thr Thr Val Tyr  Thr Glu Pro
    2105                 2110                 2115

Ala Asp  Val Ile Thr Lys Phe  Lys Asp Ser Glu Glu  Ile Ser Ser
    2120                 2125                 2130

Thr Tyr  Phe Pro Gly Ser Val  Ile Asp Tyr Pro Glu  Asp Ile Gly
    2135                 2140                 2145

Val Ser  Leu Asp Arg Thr Ile  Thr Pro Glu Ser Arg  Thr Asn Ala
    2150                 2155                 2160

Asp Gln  Ile Met Ile Ser Phe  Pro Gly Ile Ala Pro  Ser Ile Thr
    2165                 2170                 2175

Glu Ser  Val Ala Thr Lys Pro  Glu Arg Pro Gln Ala  Asp Thr Ile
    2180                 2185                 2190

Ser Thr  Asp Leu Pro Ile Ser  Glu Lys Glu Leu Ile  Lys Gly Lys
    2195                 2200                 2205

Lys Glu  Thr Gly Asp Gly Ile  Ile Leu Glu Val Leu  Asp Ala Tyr
    2210                 2215                 2220

Lys Asp  Lys Arg Glu Glu Ser  Glu Ala Glu Leu Thr  Lys Ile Ser
    2225                 2230                 2235

Leu Pro  Glu Thr Gly Leu Ala  Pro Thr Pro Ser Ser  Gln Thr Lys
    2240                 2245                 2250

Glu Gln  Pro Gly Ser Pro His  Ser Val Ser Gly Glu  Ile Ser Gly
    2255                 2260                 2265

Gln Glu  Lys Pro Thr Tyr Arg  Ser Pro Ser Gly Gly  Leu Pro Val
    2270                 2275                 2280

Ser Thr  His Pro Ser Lys Ser  His Pro Phe Phe Arg  Ser Ser Ser
    2285                 2290                 2295

Leu Asp  Ile Ser Ala Gln Pro  Pro Pro Pro Pro Pro  Pro Pro Pro
    2300                 2305                 2310

Pro Pro  Pro Pro Pro Pro Pro  Pro Pro Pro Pro Pro  Pro Leu Pro
    2315                 2320                 2325

Pro Ala  Thr Ser Pro Lys Pro  Pro Thr Tyr Pro Lys  Arg Lys Leu
    2330                 2335                 2340

Ala Ala  Ala Ala Pro Val Ala  Pro Thr Ala Ile Val  Thr Ala His
    2345                 2350                 2355

Ala Asp  Ala Ile Pro Thr Val  Glu Ala Thr Ala Ala  Arg Arg Ser
    2360                 2365                 2370

Asn Gly  Leu Pro Ala Thr Lys  Ile Cys Ala Ala Ala  Pro Pro Pro
    2375                 2380                 2385

Val Pro  Pro Lys Pro Ser Ser  Ile Pro Thr Gly Leu  Val Phe Thr
    2390                 2395                 2400

His Arg  Pro Glu Ala Ser Lys  Pro Pro Ile Ala Pro  Lys Pro Ala
    2405                 2410                 2415
```

-continued

```
Val Pro  Glu Ile Pro Val Thr  Thr Gln Lys Thr Thr  Asp Thr Cys
    2420                 2425                 2430

Pro Lys  Pro Thr Gly Leu Pro  Leu Thr Ser Asn Met  Ser Leu Asn
    2435                 2440                 2445

Leu Val  Thr Ser Ala Asp Tyr  Lys Leu Pro Ser Pro  Thr Ser Pro
    2450                 2455                 2460

Leu Ser  Pro His Ser Asn Lys  Ser Ser Pro Arg Tyr  Ser Lys Ser
    2465                 2470                 2475

Leu Met  Glu Thr Tyr Val Val  Ile Thr Leu Pro Ser  Glu Pro Gly
    2480                 2485                 2490

Thr Pro  Thr Asp Ser Ser Ala  Ala Gln Ala Ile Thr  Ser Trp Pro
    2495                 2500                 2505

Leu Gly  Ser Pro Pro Lys Asp  Leu Val Ser Leu Glu  Thr Val Phe
    2510                 2515                 2520

Ser Val  Val Pro Pro Met Thr  Ser Thr Glu Ile Pro  Ser Ala Ser
    2525                 2530                 2535

Gln Pro  Thr Leu Tyr Thr Ser  Gly Ala Leu Gly Thr  Phe Ser Val
    2540                 2545                 2550

Thr Pro  Ala Val Thr Ala Ser  Leu Phe Gln Thr Val  Pro Thr Ser
    2555                 2560                 2565

Leu Thr  Gln Phe Leu Pro Ala  Glu Ala Ser Lys Pro  Glu Val Ser
    2570                 2575                 2580

Ala Val  Ser Ser Ala Val Pro  Ser Val Ala Pro Arg  Ser Val Ser
    2585                 2590                 2595

Ile Pro  Ile Pro Pro Glu Pro  Leu Ala Leu Asp Arg  His Gln Tyr
    2600                 2605                 2610

Lys Glu  Asn Gly Lys Leu Pro  Leu Ile Gly Asp Ala  Ile Asp Leu
    2615                 2620                 2625

Arg Thr  Ile Pro Lys Ser Glu  Val Lys Val Thr Glu  Lys Cys Met
    2630                 2635                 2640

Asp Leu  Ser Ala Ser Ala Met  Asp Val Lys Arg Gln  Thr Thr Ala
    2645                 2650                 2655

Asn Glu  Val Tyr Arg Arg Gln  Ile Ser Ala Val Gln  Pro Ser Ile
    2660                 2665                 2670

Ile Asn  Leu Ser Ala Ala Ser  Ser Leu Gly Thr Pro  Val Thr Met
    2675                 2680                 2685

Asp Ser  Lys Thr Val Ala Val  Val Thr Cys Thr Asp  Thr Thr Ile
    2690                 2695                 2700

Tyr Thr  Thr Gly Thr Glu Ser  Gln Val Gly Ile Glu  His Ala Val
    2705                 2710                 2715

Thr Ser  Pro Leu Gln Leu Thr  Thr Ser Lys His Thr  Glu Leu Gln
    2720                 2725                 2730

Tyr Arg  Lys Pro Ser Ser Gln  Ala Phe Pro Met Ile  Arg Asp Glu
    2735                 2740                 2745

Ala Pro  Ile Asn Leu Ser Leu  Gly Pro Ser Thr Gln  Ala Val Thr
    2750                 2755                 2760

Leu Ala  Val Thr Lys Pro Val  Thr Val Pro Pro Val  Gly Val Thr
    2765                 2770                 2775

Asn Gly  Trp Thr Asp Ser Thr  Ile Ser Gln Gly Ile  Thr Asp Gly
    2780                 2785                 2790

Glu Val  Val Asp Leu Ser Thr  Ser Lys Ser His Arg  Thr Val Val
    2795                 2800                 2805

Thr Met  Asp Glu Ser Thr Ser  Asn Val Val Thr Lys  Ile Ile Glu
```

-continued

```
    2810                2815                2820

Asp Asp  Glu Lys Pro Val Asp  Leu Thr Ala Gly Arg  Arg Ala Val
    2825                2830                2835

Cys Cys  Asp Met Val Tyr Lys  Leu Pro Phe Gly Arg  Ser Cys Thr
    2840                2845                2850

Ala Gln  Gln Pro Ala Thr Thr  Leu Pro Glu Asp Arg  Phe Gly Tyr
    2855                2860                2865

Arg Asp  Asp His Tyr Gln Tyr  Asp Arg Ser Gly Pro  Tyr Gly Tyr
    2870                2875                2880

Arg Gly  Ile Gly Gly Met Lys  Pro Ser Met Ser Asp  Thr Asn Leu
    2885                2890                2895

Ala Glu  Ala Gly His Phe Phe  Tyr Lys Ser Lys Asn  Ala Phe Asp
    2900                2905                2910

Tyr Ser  Gly Gly Thr Glu Ala  Ala Val Asp Leu Thr  Ser Gly Arg
    2915                2920                2925

Val Ser  Thr Gly Glu Val Met  Asp Tyr Ser Ser Lys  Thr Thr Gly
    2930                2935                2940

Pro Tyr  Pro Glu Thr Arg Gln  Val Ile Ser Gly Val  Gly Ile Ser
    2945                2950                2955

Thr Pro  Gln Tyr Ser Thr Ala  Arg Met Thr Pro Pro  Pro Gly Pro
    2960                2965                2970

Gln Tyr  Gly Val Gly Ser Val  Leu Arg Ser Ser Asn  Gly Val Val
    2975                2980                2985

Tyr Ser  Ser Val Ala Thr Pro  Ile Pro Ser Thr Phe  Ala Ile Thr
    2990                2995                3000

Thr Gln  Pro Gly Ser Ile Phe  Ser Thr Thr Val Arg  Asp Leu Ser
    3005                3010                3015

Gly Ile  His Thr Thr Asp Ala  Ile Thr Ser Leu Ser  Ala Leu His
    3020                3025                3030

Gln Ser  Gln Pro Met Pro Arg  Ser Tyr Phe Ile Thr  Thr Gly Ala
    3035                3040                3045

Ser Glu  Thr Asp Ile Ser Val  Thr Ser Ile Asp Ile  Asn Ala Ser
    3050                3055                3060

Leu Gln  Thr Ile Thr Met Glu  Thr Leu Pro Ala Glu  Thr Met Asp
    3065                3070                3075

Ser Val  Pro Thr Leu Thr Thr  Ala Ser Glu Val Phe  Ser Glu Val
    3080                3085                3090

Val Gly  Glu Glu Ser Thr Leu  Leu Ile Val Pro Asp  Glu Asp Lys
    3095                3100                3105

Gln Gln  Gln Gln Leu Asp Leu  Glu Arg Glu Leu Leu  Glu Leu Glu
    3110                3115                3120

Lys Ile  Lys Gln Gln Arg Phe  Ala Glu Glu Leu Glu  Trp Glu Arg
    3125                3130                3135

Gln Glu  Ile Gln Arg Phe Arg  Glu Gln Glu Lys Ile  Met Val Gln
    3140                3145                3150

Lys Lys  Leu Glu Glu Leu Gln  Ser Met Lys Gln His  Leu Leu Tyr
    3155                3160                3165

Gln Gln  Glu Glu Glu Arg Gln  Ala Gln Phe Met Met  Arg Gln Glu
    3170                3175                3180

Thr Leu  Ala Gln Gln Gln Leu  Gln Leu Glu Gln Ile  Gln Gln Leu
    3185                3190                3195

Gln Gln  Gln Leu His Gln Gln  Leu Glu Glu Gln Lys  Leu Arg Gln
    3200                3205                3210
```

-continued

Ile Tyr Gln Tyr Asn Tyr Glu Pro Ser Gly Thr Ala Ser Pro Gln
3215 3220 3225

Thr Thr Thr Glu Gln Ala Ile Leu Glu Gly Gln Tyr Val Ala Thr
3230 3235 3240

Glu Gly Ser Gln Phe Trp Ala Thr Glu Asp Ala Thr Thr Thr Ala
3245 3250 3255

Ser Thr Val Val Ala Ile Glu Ile Pro Gln Ser Gln Gly Trp Tyr
3260 3265 3270

Thr Val Gln Ser Asp Gly Val Thr Gln Tyr Ile Ala Pro Pro Gly
3275 3280 3285

Ile Leu Ser Thr Val Ser Glu Ile Pro Leu Thr Asp Val Val Val
3290 3295 3300

Lys Glu Glu Lys Gln Pro Lys Lys Arg Ser Ser Gly Ala Lys Val
3305 3310 3315

Arg Gly Gln Tyr Asp Glu Met Gly Glu Ser Met Ala Asp Asp Pro
3320 3325 3330

Arg Asn Leu Lys Lys Ile Val Asp Ser Gly Val Gln Thr Asp Asp
3335 3340 3345

Glu Glu Thr Ala Asp Arg Thr Tyr Ala Ser Arg Arg Arg Arg Thr
3350 3355 3360

Lys Lys Ser Val Asp Thr Ser Val Gln Thr Asp Asp Glu Asp Gln
3365 3370 3375

Asp Glu Trp Asp Met Pro Ser Arg Ser Arg Arg Lys Ala Arg Thr
3380 3385 3390

Gly Lys Tyr Gly Asp Ser Thr Ala Glu Gly Asp Lys Thr Lys Pro
3395 3400 3405

Pro Ser Lys Val Ser Ser Val Ala Val Gln Thr Val Ala Glu Ile
3410 3415 3420

Ser Val Gln Thr Glu Pro Leu Gly Thr Ile Arg Thr Pro Ser Ile
3425 3430 3435

Arg Ala Arg Val Asp Ala Lys Val Glu Ile Ile Lys His Ile Ser
3440 3445 3450

Ala Pro Glu Lys Thr Tyr Lys Gly Gly Ser Leu Gly Cys Gln Thr
3455 3460 3465

Glu Thr Asp Pro Asp Thr Gln Ser Pro Pro Tyr Met Gly Ala Thr
3470 3475 3480

Ser Pro Pro Lys Asp Lys Lys Arg Pro Thr Pro Leu Glu Ile Gly
3485 3490 3495

Tyr Ser Ser Ser His Leu Arg Ala Asp Pro Thr Val Gln Leu Ala
3500 3505 3510

Pro Ser Pro Pro Lys Ser Pro Lys Val Leu Tyr Ser Pro Ile Ser
3515 3520 3525

Pro Leu Ser Pro Gly His Ala Leu Glu Pro Ala Phe Val Pro Tyr
3530 3535 3540

Glu Lys Pro Leu Pro Asp Asp Ile Ser Pro Gln Lys Val Leu His
3545 3550 3555

Pro Asp Met Ala Lys Val Pro Pro Ala Ser Pro Lys Thr Ala Lys
3560 3565 3570

Met Met Gln Arg Ser Met Ser Asp Pro Lys Pro Leu Ser Pro Thr
3575 3580 3585

Ala Asp Glu Ser Ser Arg Ala Pro Phe Gln Tyr Ser Glu Gly Phe
3590 3595 3600

-continued

```
Thr Ala  Lys Gly Ser Gln Thr  Thr Ser Gly Thr Gln  Lys Lys Val
    3605                 3610                 3615

Lys Arg  Thr Leu Pro Asn Pro  Pro Pro Glu Glu Ala  Ser Thr Gly
    3620                 3625                 3630

Thr Gln  Ser Thr Tyr Ser Thr  Met Gly Thr Ala Ser  Arg Arg Arg
    3635                 3640                 3645

Met Cys  Arg Thr Asn Thr Met  Ala Arg Ala Lys Ile  Leu Gln Asp
    3650                 3655                 3660

Ile Asp  Arg Glu Leu Asp Leu  Val Glu Arg Glu Ser  Ala Lys Leu
    3665                 3670                 3675

Arg Lys  Lys Gln Ala Glu Leu  Asp Glu Glu Glu Lys  Glu Ile Asp
    3680                 3685                 3690

Ala Lys  Leu Arg Tyr Leu Glu  Met Gly Ile Asn Arg  Arg Lys Glu
    3695                 3700                 3705

Ala Leu  Leu Lys Glu Arg Glu  Lys Arg Glu Arg Ala  Tyr Leu Gln
    3710                 3715                 3720

Gly Val  Ala Glu Asp Arg Asp  Tyr Met Ser Asp Ser  Glu Val Ser
    3725                 3730                 3735

Ser Thr  Arg Pro Ser Arg Val  Glu Ser Gln His Gly  Ile Glu Arg
    3740                 3745                 3750

Pro Arg  Thr Ala Pro Gln Thr  Glu Phe Ser Gln Phe  Ile Pro Pro
    3755                 3760                 3765

Gln Thr  Gln Thr Glu Ala Gln  Leu Val Pro Pro Thr  Ser Pro Tyr
    3770                 3775                 3780

Thr Gln  Tyr Gln Tyr Ser Ser  Pro Ala Leu Pro Thr  Gln Ala Pro
    3785                 3790                 3795

Thr Pro  Tyr Thr Gln Gln Ser  His Phe Gln Gln Gln  Thr Leu Tyr
    3800                 3805                 3810

His Gln  Gln Val Ser Pro Tyr  Gln Thr Gln Pro Thr  Phe Gln Ala
    3815                 3820                 3825

Val Ala  Thr Met Ser Phe Thr  Pro Gln Ala Gln Pro  Thr Pro Thr
    3830                 3835                 3840

Pro Gln  Pro Ser Tyr Gln Leu  Pro Ser Gln Met Met  Val Ile Gln
    3845                 3850                 3855

Gln Lys  Pro Arg Gln Thr Thr  Leu Tyr Leu Glu Pro  Lys Ile Thr
    3860                 3865                 3870

Ser Thr  Tyr Glu Val Ile Arg  Asn Gln Pro Leu Met  Ile Ala Pro
    3875                 3880                 3885

Val Ser  Thr Asp Asn Thr Tyr  Ala Val Ser His Leu  Gly Ser Lys
    3890                 3895                 3900

Tyr Asn  Ser Leu Asp Leu Arg  Ile Gly Leu Glu Glu  Arg Ser Ser
    3905                 3910                 3915

Met Ala  Ser Ser Pro Ile Ser  Ser Ile Ser Ala Asp  Ser Phe Tyr
    3920                 3925                 3930

Ala Asp  Ile Asp His His Thr  Ser Arg Asn Tyr Val  Leu Ile Asp
    3935                 3940                 3945

Asp Ile  Gly Asp Ile Thr Lys  Gly Thr Ala Ala Leu  Ser Ser Ala
    3950                 3955                 3960

Phe Ser  Leu His Glu Lys Asp  Leu Ser Lys Thr Asp  Arg Leu Leu
    3965                 3970                 3975

Arg Thr  Thr Glu Thr Arg Arg  Ser Gln Glu Val Thr  Asp Phe Leu
    3980                 3985                 3990

Ala Pro  Leu Gln Thr Ser Ser  Arg Leu His Ser Tyr  Val Lys Ala
```

-continued

```
    3995                4000                4005

Glu Glu  Asp Pro Met Glu Asp  Pro Tyr Glu Leu Lys  Leu Leu Lys
    4010                4015                4020

His Gln  Ile Lys Gln Glu Phe  Arg Arg Gly Thr Glu  Ser Leu Asp
    4025                4030                4035

His Leu  Ala Gly Leu Ser His  Tyr Tyr His Ala Asp  Thr Ser Tyr
    4040                4045                4050

Arg His  Phe Pro Lys Ser Glu  Lys Tyr Ser Ile Ser  Arg Leu Thr
    4055                4060                4065

Leu Glu  Lys Gln Ala Ala Lys  Gln Leu Pro Ala Ala  Ile Leu Tyr
    4070                4075                4080

Gln Lys  Gln Ser Lys His Lys  Lys Ala Leu Ile Asp  Pro Lys Met
    4085                4090                4095

Ser Lys  Phe Ser Pro Ile Gln  Glu Ser Arg Asp Leu  Glu Pro Asp
    4100                4105                4110

Tyr Pro  Thr Tyr Leu Ser Ser  Ser Thr Ser Ser Ile  Gly Gly Ile
    4115                4120                4125

Ser Ser  Arg Ala Arg Leu Leu  Gln Asp Asp Ile Thr  Phe Gly Leu
    4130                4135                4140

Arg Lys  Asn Ile Thr Asp Gln  Gln Lys Phe Met Gly  Ser Ser Leu
    4145                4150                4155

Gly Ser  Gly Leu Gly Thr Leu  Gly Asn Thr Ile Arg  Ser Ala Leu
    4160                4165                4170

Gln Asp  Glu Ala Asp Lys Pro  Tyr Ser Ser Gly Ser  Arg Ser Arg
    4175                4180                4185

Pro Ser  Ser Arg Pro Ser Ser  Val Tyr Gly Leu Asp  Leu Ser Ile
    4190                4195                4200

Lys Arg  Asp Ser Ser Ser Ser  Ser Leu Arg Leu Lys  Ala Gln Glu
    4205                4210                4215

Ala Glu  Ala Leu Asp Val Ser  Phe Gly His Ser Ser  Ser Ser Ala
    4220                4225                4230

Arg Thr  Lys Pro Thr Ser Leu  Pro Ile Ser Gln Ser  Arg Gly Arg
    4235                4240                4245

Ile Pro  Ile Val Ala Gln Asn  Ser Glu Glu Glu Ser  Pro Leu Ser
    4250                4255                4260

Pro Val  Gly Gln Pro Met Gly  Met Ala Arg Ala Ala  Ala Gly Pro
    4265                4270                4275

Leu Pro  Pro Ile Ser Ala Asp  Thr Arg Asp Gln Phe  Gly Ser Ser
    4280                4285                4290

His Ser  Leu Pro Glu Val Gln  Gln His Met Arg Glu  Glu Ser Arg
    4295                4300                4305

Thr Arg  Gly Tyr Asp Arg Asp  Ile Ala Phe Ile Met  Asp Asp Phe
    4310                4315                4320

Gln His  Ala Met Ser Asp Ser  Glu Ala Tyr His Leu  Arg Arg Glu
    4325                4330                4335

Glu Thr  Asp Trp Phe Asp Lys  Pro Arg Glu Ser Arg  Leu Glu Asn
    4340                4345                4350

Gly His  Gly Leu Asp Arg Lys  Leu Pro Glu Arg Leu  Val His Ser
    4355                4360                4365

Arg Pro  Leu Ser Gln His Gln  Glu Gln Ile Leu Gln  Met Asn Gly
    4370                4375                4380

Lys Thr  Met His Tyr Ile Phe  Pro His Ala Arg Ile  Lys Ile Thr
    4385                4390                4395
```

-continued

```
Arg Asp  Ser Lys Asp His Thr  Val Ser Gly Asn Gly  Leu Gly Ile
    4400                 4405                 4410

Arg Ile  Val Gly Gly Lys Glu  Ile Pro Gly His Ser  Gly Glu Ile
    4415                 4420                 4425

Gly Ala  Tyr Ile Ala Lys Ile  Leu Pro Gly Gly Ser  Ala Glu His
    4430                 4435                 4440

Ser Gly  Lys Leu Ile Glu Gly  Met Gln Val Leu Glu  Trp Asn Gly
    4445                 4450                 4455

Ile Pro  Leu Thr Ser Lys Thr  Tyr Glu Glu Val Gln  Ser Ile Ile
    4460                 4465                 4470

Asn Gln  Gln Ser Gly Glu Ala  Glu Ile Cys Val Arg  Leu Asp Leu
    4475                 4480                 4485

Asn Met  Leu Ser Asp Ser Glu  Asn Pro Gln His Leu  Glu Leu His
    4490                 4495                 4500

Glu Pro  Pro Lys Val Val Asp  Lys Ala Lys Ser Pro  Gly Val Asp
    4505                 4510                 4515

Pro Lys  Gln Leu Ala Ala Glu  Leu Gln Lys Val Ser  Leu Gln Gln
    4520                 4525                 4530

Ser Pro  Leu Val Met Ser Ser  Val Val Glu Lys Gly  Ala His Ala
    4535                 4540                 4545

His Ser  Gly Pro Thr Ser Ala  Gly Ser Ser Ser Val  Pro Ser Pro
    4550                 4555                 4560

Gly Gln  Pro Gly Ser Pro Ser  Val Ser Lys Lys Lys  His Gly Gly
    4565                 4570                 4575

Ser Lys  Pro Thr Asp Val Ser  Lys Thr Ala Ser His  Pro Ile Thr
    4580                 4585                 4590

Gly Glu  Ile Gln Leu Gln Ile  Asn Tyr Asp Leu Gly  Asn Leu Ile
    4595                 4600                 4605

Ile His  Ile Leu Gln Ala Arg  Asn Leu Val Pro Arg  Asp Asn Asn
    4610                 4615                 4620

Gly Tyr  Ser Asp Pro Phe Val  Lys Val Tyr Leu Leu  Pro Gly Arg
    4625                 4630                 4635

Gly Gln  Val Met Val Val Gln  Asn Ala Ser Val Glu  Tyr Lys Arg
    4640                 4645                 4650

Arg Thr  Lys Tyr Val Gln Lys  Ser Leu Asn Pro Glu  Trp Asn Gln
    4655                 4660                 4665

Thr Val  Ile Tyr Lys Ser Ile  Ser Met Glu Gln Leu  Met Lys Lys
    4670                 4675                 4680

Thr Leu  Glu Val Thr Val Trp  Asp Tyr Asp Arg Phe  Ser Ser Asn
    4685                 4690                 4695

Asp Phe  Leu Gly Glu Val Leu  Ile Asp Leu Ser Ser  Thr Ser His
    4700                 4705                 4710

Leu Asp  Asn Thr Pro Arg Trp  Tyr Pro Leu Lys Glu  Gln Thr Glu
    4715                 4720                 4725

Ser Ile  Glu His Gly Lys Ser  His Ser Ser Gln Asn  Ser Gln Gln
    4730                 4735                 4740

Ser Pro  Lys Pro Ser Val Ile  Lys Ser Arg Ser His  Gly Ile Phe
    4745                 4750                 4755

Pro Asp  Pro Ser Lys Asp Met  Gln Val Pro Thr Ile  Glu Lys Ser
    4760                 4765                 4770

His Ser  Ser Pro Gly Ser Ser  Lys Ser Ser Ser Glu  Gly His Leu
    4775                 4780                 4785
```

-continued

```
Arg Ser  His Gly Pro Ser Arg  Ser Gln Ser Lys Thr  Ser Val Ala
    4790                4795                4800

Gln Thr  His Leu Glu Asp Ala  Gly Ala Ala Ile Ala  Ala Ala Glu
    4805                4810                4815

Ala Ala  Val Gln Gln Leu Arg  Ile Gln Pro Ser Lys  Arg Arg Lys
    4820                4825                4830
```

<210> SEQ ID NO 10
<211> LENGTH: 134
<212> TYPE: PRT
<213> ORGANISM: Homo sapiens

<400> SEQUENCE: 10

```
Met Ala Asp Ile Glu Gln Tyr Tyr Met Lys Pro Pro Gly Ser Cys Phe
1               5                   10                  15

Trp Val Ala Val Leu Asp Gly Asn Val Val Gly Ile Val Ala Ala Arg
            20                  25                  30

Ala His Glu Glu Asp Asn Thr Val Glu Leu Leu Arg Met Ser Val Asp
        35                  40                  45

Ser Arg Phe Arg Gly Lys Gly Ile Ala Lys Ala Leu Gly Arg Lys Val
    50                  55                  60

Leu Glu Phe Ala Val Val His Asn Tyr Ser Ala Val Val Leu Gly Thr
65                  70                  75                  80

Thr Ala Val Lys Val Ala Ala His Lys Leu Tyr Glu Ser Leu Gly Phe
                85                  90                  95

Arg His Met Gly Ala Ser Asp His Tyr Val Leu Pro Gly Met Thr Leu
            100                 105                 110

Ser Leu Ala Glu Arg Leu Phe Phe Gln Val Arg Tyr His Arg Tyr Arg
        115                 120                 125

Leu Gln Leu Arg Glu Glu
    130
```

<210> SEQ ID NO 11
<211> LENGTH: 426
<212> TYPE: PRT
<213> ORGANISM: Homo sapiens

<400> SEQUENCE: 11

```
Met Ile Glu Leu Thr Phe Phe Ile Leu Ser Ala Phe Lys Leu Arg Asp
1               5                   10                  15

Thr His Leu Trp Tyr Phe Val Ile Pro Gly Phe Ser Ile Phe Gly Ile
            20                  25                  30

Phe Trp Met Ile Cys His Ile Ile Phe Leu Leu Thr Leu Trp Gly Phe
        35                  40                  45

His Thr Lys Leu Asn Asp Cys His Lys Val Tyr Phe Thr Pro Arg Thr
    50                  55                  60

Asp Tyr Asn Ser Leu Asp Arg Ile Met Ala Ser Lys Gly Met Arg His
65                  70                  75                  80

Phe Cys Leu Ile Ser Glu Gln Leu Val Phe Phe Ser Leu Leu Ala Thr
                85                  90                  95

Ala Ile Leu Gly Ala Val Ser Trp Gln Pro Thr Asn Gly Ile Phe Leu
            100                 105                 110

Ser Met Phe Leu Ile Val Leu Pro Leu Glu Ser Met Ala His Gly Leu
        115                 120                 125

Phe His Glu Leu Gly Asn Cys Leu Gly Gly Thr Ser Val Gly Tyr Ala
    130                 135                 140
```

-continued

Ile Val Ile Pro Thr Asn Phe Cys Ser Pro Asp Gly Gln Pro Thr Leu
145 150 155 160

Leu Pro Pro Glu His Val Gln Glu Leu Asn Leu Arg Ser Thr Gly Met
165 170 175

Leu Asn Ala Ile Gln Arg Phe Phe Ala Tyr His Met Ile Glu Thr Tyr
180 185 190

Gly Cys Asp Tyr Ser Thr Ser Gly Leu Ser Phe Asp Thr Leu His Ser
195 200 205

Lys Leu Lys Ala Phe Leu Glu Leu Arg Thr Val Asp Gly Pro Arg His
210 215 220

Asp Thr Tyr Ile Leu Tyr Tyr Ser Gly His Thr His Gly Thr Gly Glu
225 230 235 240

Trp Ala Leu Ala Gly Gly Asp Thr Leu Arg Leu Asp Thr Leu Ile Glu
245 250 255

Trp Trp Arg Glu Lys Asn Gly Ser Phe Cys Ser Arg Leu Ile Ile Val
260 265 270

Leu Asp Ser Glu Asn Ser Thr Pro Trp Val Lys Glu Val Arg Lys Ile
275 280 285

Asn Asp Gln Tyr Ile Ala Val Gln Gly Ala Glu Leu Ile Lys Ala Val
290 295 300

Asp Ile Glu Glu Ala Asp Pro Pro Gln Leu Gly Asp Phe Thr Lys Asp
305 310 315 320

Trp Val Glu Tyr Asn Cys Asn Ser Ser Asn Asn Ile Cys Trp Thr Glu
325 330 335

Lys Gly Arg Thr Val Lys Ala Val Tyr Gly Val Ser Lys Arg Trp Ser
340 345 350

Asp Tyr Thr Leu His Leu Pro Thr Gly Ser Asp Val Ala Lys His Trp
355 360 365

Met Leu His Phe Pro Arg Ile Thr Tyr Pro Leu Val His Leu Ala Asn
370 375 380

Trp Leu Cys Gly Leu Asn Leu Phe Trp Ile Cys Lys Thr Cys Phe Arg
385 390 395 400

Cys Leu Lys Arg Leu Lys Met Ser Trp Phe Leu Pro Thr Val Leu Asp
405 410 415

Thr Gly Gln Gly Phe Lys Leu Val Lys Ser
420 425

<210> SEQ ID NO 12
<211> LENGTH: 1014
<212> TYPE: PRT
<213> ORGANISM: Homo sapiens

<400> SEQUENCE: 12

Met Pro Thr Arg Ser Arg Arg Lys Ala Arg Val Gly Lys Tyr Gly Asp
1 5 10 15

Ser Met Thr Glu Ala Asp Lys Thr Lys Pro Leu Ser Lys Val Ser Ser
20 25 30

Ile Ala Val Gln Thr Val Ala Glu Ile Ser Val Gln Thr Glu Pro Val
35 40 45

Gly Thr Ile Arg Thr Pro Ser Ile Arg Ala Arg Val Asp Ala Lys Val
50 55 60

Glu Ile Ile Lys His Ile Ser Ala Pro Glu Lys Thr Tyr Lys Gly Gly
65 70 75 80

Ser Leu Gly Cys Gln Thr Glu Ala Asp Ser Asp Thr Gln Ser Pro Gln
85 90 95

-continued

```
Tyr Leu Ser Ala Thr Ser Pro Pro Lys Asp Lys Lys Arg Pro Thr Pro
            100                 105                 110

Leu Glu Ile Gly Tyr Ser Ser His Leu Arg Ala Asp Ser Thr Val Gln
        115                 120                 125

Leu Ala Pro Ser Pro Pro Lys Ser Pro Lys Val Leu Tyr Ser Pro Ile
    130                 135                 140

Ser Pro Leu Ser Pro Gly Lys Ala Leu Glu Ser Ala Phe Val Pro Tyr
145                 150                 155                 160

Glu Lys Pro Leu Pro Asp Asp Ile Ser Pro Gln Lys Val Leu His Pro
                165                 170                 175

Asp Met Ala Lys Val Pro Pro Ala Ser Pro Lys Thr Ala Lys Met Met
            180                 185                 190

Gln Arg Ser Met Ser Asp Pro Lys Pro Leu Ser Pro Thr Ala Asp Glu
        195                 200                 205

Ser Ser Arg Ala Pro Phe Gln Tyr Thr Glu Gly Tyr Thr Thr Lys Gly
    210                 215                 220

Ser Gln Thr Met Thr Ser Ser Gly Ala Gln Lys Lys Val Lys Arg Thr
225                 230                 235                 240

Leu Pro Asn Pro Pro Pro Glu Glu Ile Ser Thr Gly Thr Gln Ser Thr
                245                 250                 255

Phe Ser Thr Met Gly Thr Val Ser Arg Arg Arg Ile Cys Arg Thr Asn
            260                 265                 270

Thr Met Ala Arg Ala Lys Ile Leu Gln Asp Ile Asp Arg Glu Leu Asp
        275                 280                 285

Leu Val Glu Arg Glu Ser Ala Lys Leu Arg Lys Lys Gln Ala Glu Leu
    290                 295                 300

Asp Glu Glu Glu Lys Glu Ile Asp Ala Lys Leu Arg Tyr Leu Glu Met
305                 310                 315                 320

Gly Ile Asn Arg Arg Lys Glu Ala Leu Leu Lys Glu Arg Glu Lys Arg
                325                 330                 335

Glu Arg Ala Tyr Leu Gln Gly Val Ala Glu Asp Arg Asp Tyr Met Ser
            340                 345                 350

Asp Ser Glu Val Ser Ser Thr Arg Pro Thr Arg Ile Glu Ser Gln His
        355                 360                 365

Gly Ile Glu Arg Pro Arg Thr Ala Pro Gln Thr Glu Phe Ser Gln Phe
    370                 375                 380

Ile Pro Pro Gln Thr Gln Thr Glu Ser Gln Leu Val Pro Pro Thr Ser
385                 390                 395                 400

Pro Tyr Thr Gln Tyr Gln Tyr Ser Ser Pro Ala Leu Pro Thr Gln Ala
                405                 410                 415

Pro Thr Ser Tyr Thr Gln Gln Ser His Phe Glu Gln Gln Thr Leu Tyr
            420                 425                 430

His Gln Gln Val Ser Pro Tyr Gln Thr Gln Pro Thr Phe Gln Ala Val
        435                 440                 445

Ala Thr Met Ser Phe Thr Pro Gln Val Gln Pro Thr Pro Thr Pro Gln
    450                 455                 460

Pro Ser Tyr Gln Leu Pro Ser Gln Met Met Val Ile Gln Gln Lys Pro
465                 470                 475                 480

Arg Gln Thr Thr Leu Tyr Leu Glu Pro Lys Ile Thr Ser Asn Tyr Glu
                485                 490                 495

Val Ile Arg Asn Gln Pro Leu Met Ile Ala Pro Val Ser Thr Asp Asn
            500                 505                 510
```

-continued

```
Thr Phe Ala Val Ser His Leu Gly Ser Lys Tyr Asn Ser Leu Asp Leu
        515                 520                 525

Arg Ile Gly Leu Glu Glu Arg Ser Ser Met Ala Ser Ser Pro Ile Ser
    530                 535                 540

Ser Ile Ser Ala Asp Ser Phe Tyr Ala Asp Ile Asp His His Thr Pro
545                 550                 555                 560

Arg Asn Tyr Val Leu Ile Asp Asp Ile Gly Glu Ile Thr Lys Gly Thr
                565                 570                 575

Ala Ala Leu Ser Thr Ala Phe Ser Leu His Glu Lys Asp Leu Ser Lys
            580                 585                 590

Thr Asp Arg Leu Leu Arg Thr Thr Glu Thr Arg Arg Ser Gln Glu Val
        595                 600                 605

Thr Asp Phe Leu Ala Pro Leu Gln Ser Ser Ser Arg Leu His Ser Tyr
    610                 615                 620

Val Lys Ala Glu Glu Asp Pro Met Glu Asp Pro Tyr Glu Leu Lys Leu
625                 630                 635                 640

Leu Lys His Gln Ile Lys Gln Glu Phe Arg Arg Gly Thr Glu Ser Leu
                645                 650                 655

Asp His Leu Ala Gly Leu Ser His Tyr Tyr His Ala Asp Thr Ser Tyr
            660                 665                 670

Arg His Phe Pro Lys Ser Glu Lys Tyr Ser Ile Ser Arg Leu Thr Leu
        675                 680                 685

Glu Lys Gln Ala Ala Lys Gln Leu Pro Ala Ala Ile Leu Tyr Gln Lys
    690                 695                 700

Gln Ser Lys His Lys Lys Ser Leu Ile Asp Pro Lys Met Ser Lys Phe
705                 710                 715                 720

Ser Pro Ile Gln Glu Ser Arg Asp Leu Glu Pro Asp Tyr Ser Ser Tyr
                725                 730                 735

Met Thr Ser Ser Thr Ser Ser Ile Gly Gly Ile Ser Ser Arg Ala Arg
            740                 745                 750

Leu Leu Gln Asp Asp Ile Thr Phe Gly Leu Arg Lys Asn Ile Thr Asp
        755                 760                 765

Gln Gln Lys Phe Met Gly Ser Ser Leu Gly Thr Gly Leu Gly Thr Leu
    770                 775                 780

Gly Asn Thr Ile Arg Ser Ala Leu Gln Asp Glu Ala Asp Lys Pro Tyr
785                 790                 795                 800

Ser Ser Gly Ser Arg Ser Arg Pro Ser Ser Arg Pro Ser Ser Val Tyr
                805                 810                 815

Gly Leu Asp Leu Ser Ile Lys Arg Asp Ser Ser Ser Ser Ser Leu Arg
            820                 825                 830

Leu Lys Ala Gln Glu Ala Glu Ala Leu Asp Val Ser Phe Ser His Ala
        835                 840                 845

Ser Ser Ser Ala Arg Thr Lys Pro Thr Ser Leu Pro Ile Ser Gln Ser
    850                 855                 860

Arg Gly Arg Ile Pro Ile Val Ala Gln Asn Ser Glu Glu Glu Ser Pro
865                 870                 875                 880

Leu Ser Pro Val Gly Gln Pro Met Gly Met Ala Arg Ala Ala Ala Gly
                885                 890                 895

Pro Leu Pro Pro Ile Ser Ala Asp Thr Arg Asp Gln Phe Gly Ser Ser
            900                 905                 910

His Ser Leu Pro Glu Val Gln Gln His Met Arg Glu Glu Ser Arg Thr
        915                 920                 925

Arg Gly Tyr Asp Arg Asp Ile Ala Phe Ile Met Asp Asp Phe Gln His
```

-continued

```
    930                 935                 940

Ala Met Ser Asp Ser Glu Gly Lys Leu Gly Leu Lys Leu Pro Cys Tyr
945                 950                 955                 960

Ser Gln Asn Ser Asn Ser Tyr Phe Ser Ala Cys Leu Ile Ser Leu Leu
                965                 970                 975

Gln Arg Cys Ile Leu Leu Phe Leu Val Cys Leu Leu His Val Tyr Phe
            980                 985                 990

Asn Phe Ile Ser Cys Lys Trp Lys  Phe Tyr His Val Tyr  Arg Phe Cys
        995                 1000                1005

Ser Met  Leu Phe Phe Ile
    1010
```

<210> SEQ ID NO 13
<211> LENGTH: 20
<212> TYPE: DNA
<213> ORGANISM: Artificial
<220> FEATURE:
<223> OTHER INFORMATION: forward primer for RT-PCR

<400> SEQUENCE: 13
cttgcctccc cagcccatca 20

<210> SEQ ID NO 14
<211> LENGTH: 20
<212> TYPE: DNA
<213> ORGANISM: Artificial
<220> FEATURE:
<223> OTHER INFORMATION: reverse primer for RT-PCR

<400> SEQUENCE: 14
ctgggggcca gggttctgct 20

<210> SEQ ID NO 15
<211> LENGTH: 20
<212> TYPE: DNA
<213> ORGANISM: Artificial
<220> FEATURE:
<223> OTHER INFORMATION: forward primer for RT-PCR

<400> SEQUENCE: 15
gggtggccgg gtaggtggaa 20

<210> SEQ ID NO 16
<211> LENGTH: 20
<212> TYPE: DNA
<213> ORGANISM: Artificial
<220> FEATURE:
<223> OTHER INFORMATION: reverse primer for RT-PCR

<400> SEQUENCE: 16
ggcagtgccc agcccttcct 20

<210> SEQ ID NO 17
<211> LENGTH: 22
<212> TYPE: DNA
<213> ORGANISM: Artificial
<220> FEATURE:
<223> OTHER INFORMATION: forward primer for RT-PCR

<400> SEQUENCE: 17
tgtacattcc tccctggtgg tg 22

<210> SEQ ID NO 18

-continued

<211> LENGTH: 27
<212> TYPE: DNA
<213> ORGANISM: Artificial
<220> FEATURE:
<223> OTHER INFORMATION: reverse primer for RT-PCR

<400> SEQUENCE: 18
aaatctgaga gctgcaagaa aataggg 27

<210> SEQ ID NO 19
<211> LENGTH: 17
<212> TYPE: PRT
<213> ORGANISM: Mus musculus

<400> SEQUENCE: 19

Cys Asn Thr Ala Phe Arg Gly Leu Arg Gln His Pro Arg Thr Gln Leu
1 5 10 15

Leu

<210> SEQ ID NO 20
<211> LENGTH: 18
<212> TYPE: PRT
<213> ORGANISM: Mus musculus

<400> SEQUENCE: 20

Cys Met Ser Val Asp Ser Arg Phe Arg Gly Lys Gly Ile Ala Lys Ala
1 5 10 15

Leu Gly

<210> SEQ ID NO 21
<211> LENGTH: 2788
<212> TYPE: DNA
<213> ORGANISM: Mus musculus

<400> SEQUENCE: 21
atggtctgcg agacgaagat cgtggctacg gaggaccatg aggcactgcc gggggccaag 60
aaggacgcgc tgctcgtcgc cgccggagcc atgtggcccc cgctgcccgc cgcgcccggg 120
ccggccgccg cacccccacc cgcggcaggt ccccagcccc acggaggcac cgggggcgcg 180
gggccgccgg aggggcgcgg cgtgtgcatc cgcgagttcc gcgcagccga gcaggaggcg 240
gcgcgccgca tcttctacga cggcatcttg gagcgcatcc ccaacacggc tttccgcggc 300
ctgcggcagc acccgcgcac ccaactgctc tacgccctgc tggccgccct ctgttttgct 360
gtgacccgct cactgctgct gacatgcctg gtgccggccg ggctcctggc cctgcgctac 420
tactacagcc gcaaggtgat tctggcctac ctggagtgtg cgctgcacac ggacatggct 480
gacattgagc agtactacat gaagccacct ggttcctgtt tctgggtggc tgtgctggac 540
ggcaacgttg tgggcatcgt ggccgcacgg gcccatgagg aggacaacac agtggagctg 600
ctccgcatgt ccgtggactc gcgtttccgc ggaaaaggca tcgccaaggc tctgggcagg 660
agggtgttgg agtttgccat gctgcacaac tactctgcag tggtactggg caccacagcc 720
gttaaggtgg ccgcccacaa gctctatgag tcactgggct tcagacacat gggcgcgagt 780
gatcactacg tgctgcctgg catgaccctc tcgctggccg agcgcctctt cttccaggtc 840
cgctaccacc gctaccgcct gcagctgcgc gaggagtgac caccaccacc tgcccaccac 900
cctgtctgcc cccgtccacc tctgccctct tgctcactgc ctagtgcggc cctgctttcc 960
aatgctcacc ttggcatttg tttgggtttt cctttttcag catcatgctg gttcatcacc 1020
tggctggttc tggggccaca gggtcccagt ccagagtgct catctgcaac actctggtgg 1080

-continued ggtggattgt ctgcagccat ggcccttgcc tccccagccc atcagagtgg ctcatcatgc 1140
cttgaagagc agcattgtgg accatctgaa ctatccacaa agctgcccag cctgcctcca 1200
tcagggaagg actagccttg cccatcaagc acagaacctc tacaacaacc cccccccccc 1260
caaggagcag aaccctggcc cccagccagg ctaaggctca actattggcc tctggaagag 1320
tggtctgctg ggctggccag ccactgcccc atgggaggct gagctggtcc caggccctgc 1380
tttgccctgt gcatgctaag gacatggcct ggctgcagca tgccgcatgc cacagccccc 1440
tgccccacta tcctgcccag cctggacctc aggcctgagc tggtgagctc ccttgtcctg 1500
tcctgagctg gcctctggag ggcctacctg cctgaccctg tctactctct ggtgaggcct 1560
ggcctggcct aacctggctc tatccactcc tgctttgctt cgaaatcatc ttacctcttt 1620 cccttttttgg tccccgtgcc tccttgctct ggctgacttg gctggtcacc cgggtttggt 1680
tcctgtagca atccactgca cagcatggtg gggatttcat gggggtgggg ggggacacct 1740
cccccaacac ctgttagacc aggtggccac ctcccagctg cctgaggtcc tgtggcctca 1800
tgctgtttgt ggggtctgcc ctgtgaatgt aactagccca ggctgttgtt ggcaatgcct 1860
gccacagctt ctcccagcct gaaacaaccc attctctaat aagttacgta gacagaatag 1920
cactctgcat gactttaatt actgggacaa aatggtagtt tgagcctcca gacacacatc 1980
tgtgtggtgc tagcatacgc atggtctctg gccccatttg atgggggtgg gtggccgggt 2040
aggtggaaga tttcagtttg aagtatggaa ggagactcta atttagtgta aacaccccta 2100
aagtgccctc acaacacagt ctgtgaggct caggttgccc cttgattcct tgtatgcagg 2160
attgagggga ctggagggtc ctaaagcctc ataggaaggg ctgggcactg cctcggggga 2220
agaagctggt ggttggggtg ggtccaggta tcacccacta cagactactc tgctaggtca 2280
actgttcctg gcctctcctt tttgaggttc tacttcagat ccagcctaga tgggggtggg 2340
tatggcctag gacagggaaa ggcagtagct ggcagtggtc atgaggccag ctgaaacttg 2400
gacttagctt tagtgcaggg ggtgcataaa ggcccgtcca cattcctctg tgtggggctt 2460
ggggtgagga gtggcaggct aggtagacca tagagctggg cccctggcac caaggctaca 2520
ttattagaaa ggctctttag agttaatgag ttggtggaac aagcccagct tcctgagggg 2580
ccttttgtcc tgttagcaat tgaggcattt gcagaacact gtacagaccc cgctctcccc 2640
tgtacattcc tccctggtgg tgcccggtcc ccgcttgggg atgggagttt tgtagactgt 2700
acagaaattg gcaccctatt ttcttgcagc tctcagattt tgttaatctg gattatacag 2760
acagatgtaa agtgttttag caaaatgg 2788

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
cttgcctccc cagcccatca 20

<210> SEQ ID NO 23
<211> LENGTH: 20
<212> TYPE: DNA
<213> ORGANISM: Artificial Sequence
<220> FEATURE:
<223> OTHER INFORMATION: Primer -continued

<400> SEQUENCE: 23
ctgggggcca gggttctgct 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gggtggccgg gtaggtggaa 20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
ggcagtgccc agcccttcct 20

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
tgtacattcc tccctggtgg tg 22

<210> SEQ ID NO 27
<211> LENGTH: 27
<212> TYPE: DNA
<213> ORGANISM: Artificial Sequence
<220> FEATURE:
<223> OTHER INFORMATION: Primer

<400> SEQUENCE: 27
aaatctgaga gctgcaagaa aataggg 27

<210> SEQ ID NO 28
<211> LENGTH: 4551
<212> TYPE: DNA
<213> ORGANISM: Mus musculus

<400> SEQUENCE: 28
gagtctcaaa ttagcttcag agcagtttat tattctgtca tttttgtaag agtccactgc 60
cttagtttca taatttataa aatacaaatt tctatgttaa attattaaga gcatttggga 120
aggtgtaata aaatcaatca cagaaaaata cttagaataa ttagatcata gacaataccc 180
atggctgtgt atagagttgt ttcatatgga aaggaagaaa ggaattgtag gattagagct 240
agagagagca atgcctttcc acttaggtag gggagcctag ctcctgatac acagatatgt 300
gcacagcaag gtaacatctc aacgctagtt tccttattta attgtggacc tgaagaacct 360
aaaaattata caaaactgat gtgaaatggc acccatctga aattcaagat gcacacaaat 420
gaatgattta ttcagtgaaa tttactatct gtatttctag ttgtaaaaca agattcattt 480
tttaaaaaaa atattgtata taggatgcca ctaactttca atattgtatc aattcttcag 540
tattctggaa taaggaaata ttttcaaatc aacatgccac caaacataaa ctctaaaagc 600

-continued

```
aaaggcattt tgtataactt ccacttttaa tacagtaaaa tattcaggaa ctcttaattt    660
cacattaaat gaaaaattaa ttttttacaa aatattattc aaagtattaa gagtacaata    720
ttcaaaacat agaaataggc tgtagcaatg ctgcatagat aacagtatac aagttccctg    780
atggtgtgac ttctttctaa ataaaatgtc agttttcaag tcattggtag aaaatggtag    840
atgcatccgt taccttccct ctctgggcat ggaaaaatgg cttcaacggt gagaagtcac    900
catggtaaca aagtctaatc tccactttaa ttatacctcc ctctttcaaa gatgaaaatc    960
tagaatgtaa ggataattgg aaggggacag gaagtgactt acctcttaag gagatatcct   1020
gatcagcgcc tactttactc caacaaaaca ctgaattaaa gtttacaaat tacaaccata   1080
ccattatgct tacctaaaac tgccaaaatg aatacttttt tacataatac aatacaggta   1140
tataacaaca acaacaacaa aatgatctgt tcccatcctt gaccttcagc agaaaaaagt   1200
tattacaata ggactgaaaa gcaactttca tggcagagta ctaactcctc ataaatacgt   1260
aagacaggaa gaatcggtca atgagaaact gatacattta tttttgtaag tgtgtacttt   1320
ttgaaaagaa tggcaattta cttgaaagga atttgtagct ggaaatacta ctcattaaga   1380
aaacaaaatt accctgagaa ggactcttaa atttaccagt attttcaaag tccctcacta   1440
accatgaagg aacactttgt agcatgtaag ctcttattgt tacctacatt aacaatgctt   1500
tcatctcaaa ggcagttggg gcttttctgc tgtactgtaa aggtcatagc caagacatct   1560
gggtgtggtg gtaaaagggc attttgcagt cattatgagc aggtctcttc ctgctccaag   1620
tatttatact tctgcaaaca gtcctggggc caaacctata tgaatcacac acatgaaaga   1680
atctcctact aagtaaactg gtagttctct taaaacacac ttgtctggtc tacattctct   1740
aacgggtgcc tagaaaataa ggcattagga attgtccatt ggccactcca gagcacagac   1800
aactgtgttt cttttcattg gagacaaatg gaaagttatt tgaaagtgca ctgttacttt   1860
taacatctct tacacattta cattcagcat tttcatgacc ctccatatac ttttagtata   1920
aaatcatgca tattcccaat atcttccaca tcccataatt acttaagaaa agacaaagtg   1980
agaacagcta caaatgtagc aagatacttt ccacaaataa aaatacagca tacaaaaaat   2040
ggcaagttac tgataaatgg taacatgaac tctcaataat agccttcctt gatgtccaca   2100
ttaagatttg acaagtttaa agccttgtcc tgtgtccagc actgtaggaa gaaaccaact   2160
catttttaac cttttcaagc acctaaaaca agctttgcag acccaaaaga ggttcaggcc   2220
acataaccag ttggccaagt gcactaacgg atacgtaacc cgagggaagt gtaacatcca   2280
gtgcttggcc acatcgcttc ctgtcggcag gtgcagcgtg tagtcgctcc agcgctttga   2340
cacgccatac acggccctca ctgtgcgccc cttctcagtc cagcagatgt tgtttgtgga   2400
gttacagttg tattctaccc agtctctagt aaagtcaccc agctgtggcg ggtcagcttc   2460
ttcaatatct actgtcttcg ccagctcagc tccctgaact gcaacatact ggtcattaat   2520
ctttctcact tctttcaccc atggggttga attctcgctg tctaagatga tgataagccg   2580
ggaacagaag gaaccgttct tctctctcca ccattctaaa agcgtatcaa ggcgaagtat   2640
gtctccacct gcgagggccc actctcctga gccatgggtg tgtccactgt aatataaaac   2700
atatgtatca tgtctaggtc catccactgt ccgaagttca aggaaagctt tcagtttgga   2760
atgcagagta tcaaaagaca gcccacttgt ggaatagtca catccatagg tctcaatcat   2820
atgatatgca aaaaatcttt ggatggcatt gagcatgcca gtagacctca aatttaactc   2880
ctgtacatgt tctggcggaa gcagtgttgg ctggccatca gggctgcaga agttggtagg   2940
```

-continued

```
gatcacaata gcgtatccaa cagaggttcc ccctaagcag ttgccaagtt catggaagag   3000

cccatgagcc atggactcca gcggcaagac aatgagaaac atgctcaaga agattccatt   3060

ggttggctgc caggagactg ctcccaaaat tgccgttgca agaagactaa aaaaaactaa   3120

ctgctctgaa attaagcaaa aatgacgcat ccctttggat gccatgattc tgtcaaggct   3180

attgttatct gccctgtggt tgatatacac tttatggcag tcattcaact tagtatgaaa   3240

tccccaaaga gttaaaagaa aaataatatg gcaaatcatc cagaaaaatc cgaaaatgga   3300

aaaacctggt atcacaaaat accagagatg agtgtctcta agtttaaatg ctgaaaggat   3360

gaagaatgta agctcaatca ttgcagtgaa aagcacagaa agtctcctgc aaattctccc   3420

acgatgcaga aaaggtttcc acctctcagt tactgaaagt ccactaaaat aaatgtcaag   3480

aaaaggatca gttaccaggc aaataaaaaa acatgcaaaa gcaattggat tttggggagt   3540

ttccaatgaa gagaaaaata acaatactga aaaaatgatt aagtttggaa tagctagaaa   3600

agacttcatt ctcaggtcga taatgagcat ggccaaagcc ataaccagca aaataacact   3660

cagagacttc tccaccaaca tagttgtgct ggcgatggca aacccaacaa gttccagaaa   3720

ctccactgtg gttagtaaag taggccgatg gcggacatat ccagaaattc tctccaccaa   3780

agcacacaat atccttaaaa ctatagatgt cagaagcaaa tatttggttg tttcttcttt   3840

cacatcactt ttaaaggatg aattatcaag aaaacacaga aggccaagca gaaatccaaa   3900

ccagagattg gagagactta aactggctgc ttccattgaa aagtaatagt agagtatgct   3960

ggcgatccca agaacaaaga ggccgaggat aaaaatcacc aaaattaagg aatttgctgt   4020

tttttcccat cttacataaa ggcctaaaca tatggccaca agtaagttga tcctggctag   4080

atagccgagg taccgcacgg aggaatgcat gttcacttct ctatttactt cttccagcct   4140

agtcattgct agatagagac aatgactaac acagtatcgc agtgatctgc acatgtaatc   4200

tggcactgga gggtcccaag aggcacaaaa attaacttcc tgtatttcat tcaataaagc   4260

caaggtgttg gtaatgccta ctccaacatt ctctcagaag ttttctttgt aatgacccga   4320

gtcagcggtc gccagcgagc ctcgctcttt ccgctgcgaa gctcgcagag ccaaagggcg   4380

cggagcctcc gagccagaac gcggaggtga tgtggggacg tgagcccgag gcctcccgca   4440

ctagcaccgc aaggcctcgg tagaaacttt cgctaggacc gacacgaccg ccatgtttcc   4500

gccgctgact cccagcgcta cggatcgccg tcagggacaa ggcgcgccgc c            4551


<210> SEQ ID NO 29
<211> LENGTH: 25
<212> TYPE: DNA
<213> ORGANISM: Artificial Sequence
<220> FEATURE:
<223> OTHER INFORMATION: Primer

<400> SEQUENCE: 29

gagcaatgcc tttccactta ggtag                                           25


<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30

tcagatgggt gccatttcac atca                                            24
```

-continued

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
ccttccctct ctgggcatgg a 21

<210> SEQ ID NO 32
<211> LENGTH: 27
<212> TYPE: DNA
<213> ORGANISM: Artificial Sequence
<220> FEATURE:
<223> OTHER INFORMATION: Primer

<400> SEQUENCE: 32
ggtaagtcac ttcctgtccc cttccaa 27

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
acccagctgt ggcgggtcag 20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
ggccctcgca ggtggagaca 20

<210> SEQ ID NO 35
<211> LENGTH: 25
<212> TYPE: DNA
<213> ORGANISM: Artificial Sequence
<220> FEATURE:
<223> OTHER INFORMATION: Primer

<400> SEQUENCE: 35
gagcaatgcc tttccactta ggtag 25

<210> SEQ ID NO 36
<211> LENGTH: 24
<212> TYPE: DNA
<213> ORGANISM: Artificial Sequence
<220> FEATURE:
<223> OTHER INFORMATION: Primer

<400> SEQUENCE: 36
tcagatgggt gccatttcac atca 24

<210> SEQ ID NO 37
<211> LENGTH: 21
<212> TYPE: DNA
<213> ORGANISM: Artificial Sequence
<220> FEATURE:
<223> OTHER INFORMATION: Primer -continued

```
<400> SEQUENCE: 37

ccttccctct ctgggcatgg a                                              21


<210> SEQ ID NO 38
<211> LENGTH: 27
<212> TYPE: DNA
<213> ORGANISM: Artificial Sequence
<220> FEATURE:
<223> OTHER INFORMATION: Primer

<400> SEQUENCE: 38

ggtaagtcac ttcctgtccc cttccaa                                        27


<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39

acccagctgt ggcgggtcag                                                20


<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40

ggccctcgca ggtggagaca                                                20
```